(12) United States Patent
Ozawa

(10) Patent No.: US 8,040,524 B2
(45) Date of Patent: Oct. 18, 2011

(54) OPTICAL TOMOGRAPHY IMAGING SYSTEM, CONTACT AREA DETECTING METHOD AND IMAGE PROCESSING METHOD USING THE SAME, AND OPTICAL TOMOGRAPHIC IMAGE OBTAINING METHOD

(75) Inventor: Satoshi Ozawa, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 601 days.

(21) Appl. No.: 12/233,983

(22) Filed: Sep. 19, 2008

(65) Prior Publication Data

US 2009/0073454 A1 Mar. 19, 2009

(30) Foreign Application Priority Data

Sep. 19, 2007 (JP) ................. 2007-242379
Sep. 19, 2007 (JP) ................. 2007-242457
Sep. 19, 2007 (JP) ................. 2007-242551

(51) Int. Cl.
*G01B 9/02* (2006.01)
(52) U.S. Cl. ...................................... 356/479
(58) Field of Classification Search .................. 356/479, 356/497
See application file for complete search history.

(56) References Cited

U.S. PATENT DOCUMENTS

| 5,956,355 | A * | 9/1999 | Swanson et al. ............ 372/20 |
| 6,309,370 | B1 * | 10/2001 | Haim et al. .................... 604/66 |
| 6,775,007 | B2 * | 8/2004 | Izatt et al. ..................... 356/497 |
| 6,796,943 | B2 * | 9/2004 | Mochizuki ................... 600/437 |
| 7,180,600 | B2 * | 2/2007 | Horii et al. .................... 356/479 |
| 7,310,150 | B2 * | 12/2007 | Guillermo et al. ............ 356/479 |
| 7,440,111 | B2 * | 10/2008 | Fujita ............................ 356/479 |
| 7,474,407 | B2 * | 1/2009 | Gutin ............................ 356/479 |
| 7,515,274 | B2 * | 4/2009 | Gelikonov et al. ............ 356/479 |
| 7,554,669 | B2 * | 6/2009 | Buckland et al. ............. 356/479 |
| 7,576,866 | B2 * | 8/2009 | Ohkubo ........................ 356/479 |
| 7,583,385 | B2 * | 9/2009 | Kato ............................. 356/479 |
| 7,627,208 | B2 * | 12/2009 | Kuroiwa ........................ 385/31 |
| 7,679,754 | B2 * | 3/2010 | Zuluaga ........................ 356/479 |
| 7,742,795 | B2 * | 6/2010 | Stone et al. ................... 600/381 |
| 7,768,652 | B2 * | 8/2010 | Everett ......................... 356/497 |
| 7,860,555 | B2 * | 12/2010 | Saadat .......................... 600/476 |
| 7,929,145 | B2 * | 4/2011 | Zuluaga ........................ 356/479 |
| 7,940,397 | B2 * | 5/2011 | Masuda ........................ 356/479 |

(Continued)

FOREIGN PATENT DOCUMENTS

JP    2000-131222 A    5/2000

(Continued)

*Primary Examiner* — Gregory J Toatley
*Assistant Examiner* — Scott Richey
(74) *Attorney, Agent, or Firm* — Sughrue Mion, PLLC

(57) ABSTRACT

The optical tomography imaging system includes a light source, a branching section which branches a light beam into a measuring light beam and a reference beam, an optical probe having an optical fiber, a measurement section which irradiates a measurement target with the measuring beam and picks up a reflected beam, and a sheath which encloses the optical fiber and the measurement section, a multiplexing section which combines the reflected beam with the reference beam to create an interference beam, an interference beam detecting section which detects the interference beam as interference signals, and a contact detecting section which detects a contact area in which the optical probe and the measurement target are in contact with each other. The contact detecting section calculates from the detected interference signals a distance between the optical probe and the measurement target, and uses the calculated distance to detect the contact area.

38 Claims, 23 Drawing Sheets

U.S. PATENT DOCUMENTS

| | | | |
|---|---|---|---|
| 7,944,568 B2 * | 5/2011 | Teramura et al. | 356/497 |
| 2003/0158477 A1 * | 8/2003 | Panescu | 600/424 |
| 2004/0239938 A1 * | 12/2004 | Izatt | 356/450 |
| 2005/0168751 A1 | 8/2005 | Horii et al. | |
| 2008/0009747 A1 * | 1/2008 | Saadat et al. | 600/471 |
| 2008/0058591 A1 * | 3/2008 | Saadat et al. | 600/109 |
| 2009/0079993 A1 * | 3/2009 | Yatagai et al. | 356/497 |
| 2009/0086213 A1 * | 4/2009 | Masuda | 356/479 |
| 2009/0251704 A1 * | 10/2009 | Masuda | 356/477 |
| 2010/0201991 A1 * | 8/2010 | Choma et al. | 356/511 |
| 2010/0220334 A1 * | 9/2010 | Condit et al. | 356/497 |

FOREIGN PATENT DOCUMENTS

| | | | |
|---|---|---|---|
| JP | 2007255785 A | * | 10/2007 |
| JP | 2007307553 A | * | 11/2007 |
| JP | 2008020398 A | * | 1/2008 |

* cited by examiner

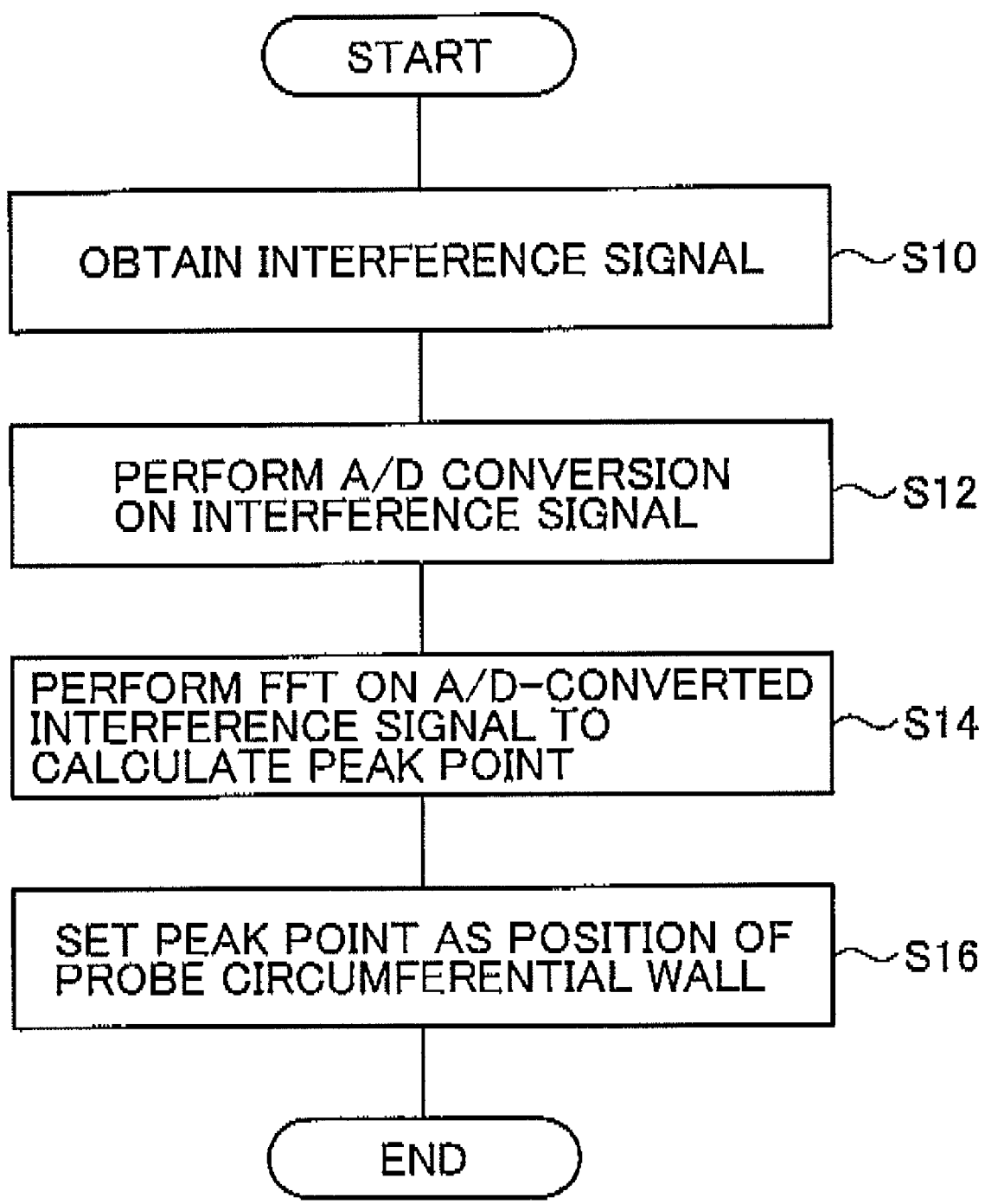

FIG. 17

OPTICAL TOMOGRAPHY IMAGING SYSTEM, CONTACT AREA DETECTING METHOD AND IMAGE PROCESSING METHOD USING THE SAME, AND OPTICAL TOMOGRAPHIC IMAGE OBTAINING METHOD

The entire contents of documents cited in this specification are incorporated herein by reference.

BACKGROUND OF THE INVENTION

The present invention relates to an optical tomography imaging system which irradiates a measurement target with a light beam to capture a tomographic image of the measurement target with a reflected light beam, a contact area detecting method and an image processing method using the contact area detecting method, and an optical tomographic image obtaining method.

Optical tomography imaging systems utilizing optical coherence tomography (OCT) are one way to obtain a sectional image without cutting into a measurement target such as living tissues.

OCT is a type of optical interferometry in which a light beam emitted from a light source is split into two beams, a measuring light beam and a reference light beam, to utilize the fact that optical interference is detected only when the light path length of the measuring light beam and the light path length of the reference light beam match within the coherence length of the light source.

An example of optical tomography imaging systems utilizing OCT is disclosed in JP 2000-131222 A. This optical tomography imaging system has a light source, a first optical coupler section, which splits a light beam emitted from the light source into a measuring light beam and a reference light beam, a measurement section, which irradiates a measurement target with the measuring light beam to detect a reflected light beam, a second optical coupler section, which causes the reflected light beam to interfere with the reference light beam which has been guided along the same light path length as the measuring light beam, and a computing section which detects a tomographic image from a result of the interference.

The optical tomography imaging system according to JP 2000-131222 A obtains a two-dimensional tomographic image by connecting an optical fiber of the measurement section rotatably with the use of a rotary joint and capturing tomographic images while rotating the optical fiber. That is, the two-dimensional image is obtained as capturing tomographic images at a plurality of points around a measurement point by rotating the optical fiber.

SUMMARY OF THE INVENTION

The optical tomography imaging system according to JP 2000-131222 A is a system that captures tomographic images at a plurality of points while rotating the measurement section which is placed at the tip of the optical fiber and thereby obtains a two-dimensional tomographic image of the surrounding area. This optical fiber is inserted into a bronchial tube, a urinary duct, a blood vessel, or the like to capture tomographic images from which a tomographic image of the inside of a living body can be obtained. Further, by rotating, the measurement section can capture 360° view tomographic images around itself.

An optical tomography imaging system of this type can obtain a high-precision, high-resolution, two-dimensional tomographic image by increasing measurement points. A high-resolution tomographic image of a human body, for example, enables doctors to make an accurate disease diagnosis with ease.

However, there arises a problem that increasing measurement points increases the amount of information to be processed and thus requires an expensive high-speed processor, which makes the optical tomography imaging system costly. Another problem caused by the increased amount of information is that displaying a measurement result takes long due to lowered processing speed.

It is an object of the present invention to provide an optical tomography imaging system that solves the above-mentioned problems inherent in the conventional technology and that is capable of producing a high-resolution tomographic image with efficiency and ease.

Another object of the present invention is to provide a contact area detecting method capable of detecting the state of an optical probe with ease and easily detecting an area where a high-precision tomographic image will be obtained.

Still another object of the present invention is to provide an image processing method capable of efficiently and easily obtaining a high-resolution tomographic image suitable for diagnostic and other uses.

Yet still another object of the present invention is to provide an optical tomographic image obtaining method and an optical tomography imaging system with which a high-resolution tomographic image suitable for diagnostic, testing, and other uses can be obtained with efficiency and ease.

As a result of extensive study for attaining the above objects, the inventors of the present invention have found that, while conventional optical tomography imaging systems detect 360° view tomographic images around the measurement section, an image of an area that is not in contact with the measurement section is low in precision and resolution. The inventors of the present invention have also found that the measurement section and a measurement target need to be in contact with each other, or almost in contact with each other, in order to obtain a high-precision, high-resolution image.

In order to attain the object described above, the present invention provides an optical tomography imaging system comprising: a light source; a branching section which branches a light beam emitted from the light source into a measuring light beam and a reference light beam; an optical probe having an optical fiber which propagates the measuring light beam, a measurement section which is placed at a tip of the optical fiber to irradiate a measurement target with the measuring light beam and to pick up a reflected light beam of the measuring light beam, and a sheath which encloses circumferential walls of the optical fiber and the measurement section and which is partially formed from a transparent material in an area where the measuring light beam exits the measurement section and the reflected light beam enter the measurement section; a driving section which rotates the measurement section and the optical fiber; a multiplexing section which combines the reflected light beam detected by the measurement section with the reference light beam to create an interference light beam; an interference light beam detecting section which detects the interference light beam as interference signals; a contact detecting section which detects a contact area in which the optical probe and the measurement target are in contact with each other; and a tomographic image obtaining section which obtains a tomographic image from the detected interference signals, wherein the contact detecting section calculates from the detected interference signals a distance between the optical probe and the measurement target, and uses the calculated distance to detect a contact area in which the optical probe and the measurement target are in contact with each other.

Preferably, the tomographic image obtaining section obtains a tomographic image of only the contact area detected by the contact detecting section.

Preferably, the tomographic image obtaining section obtains a first tomographic image by processing the interference signals of the contact area under a first processing condition, and obtains a second tomographic image by processing the interference signals of other areas than the contact area under a second processing condition, and wherein the first processing condition is a condition that makes processing accuracy higher than the second processing condition does.

Preferably, the first processing condition is a condition that makes a processing amount for one interference signal larger than the second processing condition does.

Preferably, the first processing condition is a condition that makes a count of the interference signals processed per unit area larger than the second processing condition does.

And, it is preferable that the optical tomography imaging system further comprises a condition setting section which sets the first processing condition and the second processing condition.

Preferably, the tomographic image obtaining section processes at least the interference signals of the contact area to obtain the tomographic image, and wherein the driving section rotates the measurement section at different rotation speeds in the contact area and in other areas than the contact area.

Preferably, the driving section rotates the measurement section so that, when picking up the reflected light beam of the measurement target in the contact area, the measurement section rotates at a lower rotation speed than when picking up the reflected light beam of the measurement target in the other areas than the contact area.

Preferably, the driving section varies a direction of rotation of the measurement section as well, and wherein the measurement section is turned in two opposite directions to pick up a reflected light beam of the measurement target in the contact area.

It is preferable that the optical tomography imaging system further comprises a drive control section which, based on an extent and location of the contact area detected by the contact detecting section, sets a rotation speed and a rotation position of the measurement section rotated by the driving section.

Preferably, the drive control section sets the rotation speed and the rotation position of the measurement section based also on a set resolution of the tomographic image.

Preferably, the tomographic image obtaining section obtains a tomographic image by processing only the interference signals of the contact area.

Preferably, the contact detecting section calculates from the interference signals the distance between the optical probe and the measurement target, and uses the calculated distance to detect the contact area in which the optical probe and the measurement target are in contact with each other.

Preferably, the contact detecting section detects an area in which the calculated distance between the optical probe and the measurement target is equal to or smaller than a given value as an area in a contact state and, from a result of the detection, detects the contact area.

Preferably, the contact detecting section executes contact state detection whenever the driving section finishes rotating the measurement section and the optical fiber a given number of times.

It is preferable that the optical tomography imaging system further comprises a display section which displays the tomographic image obtained by the tomographic image obtaining section.

It is preferable that the optical tomography imaging system further comprises an operation section which changes the contact area detected by the contact detecting section.

It is preferable that the optical tomography imaging system further comprises a light path length adjusting section which is placed in a light path of the reference light beam and adjusts a light path length of the reference light beam, wherein the light path length adjusting section varies the light path length of the reference light beam in order to create an interference light beam for each point in a depth direction of the measurement target.

Preferably, the interference light beam detecting section detects the interference signals for each light spectral component, the contact detecting section performs a frequency analysis on the interference signals and calculates from a result of the frequency analysis the distance between the optical probe and the measurement target, and the tomographic image obtaining section performs a frequency analysis on the interference signals and obtains the tomographic image from a result of the frequency analysis.

In order to attain the other object as described above, the present invention provides a contact area detecting method for detecting a state of contact between a measurement target and an optical probe of an optical tomography imaging system which obtains a tomographic image of the measurement target from an interference light beam created by combining a reference light beam with a reflected light beam which is reflected by the measurement target-irradiated with a measuring light beam and which is picked up by a measurement section placed at a tip of the optical probe, the measurement section being rotated while irradiating the measurement target with the measuring light beam, the method comprising: a probe position obtaining step of detecting a position of a circumferential wall of the optical probe from the reflected light beam of the measuring light beam which is picked up as a result of projecting the measuring light beam from the measurement section; a measurement target position detecting step of detecting a position of a surface of the measurement target from the reflected light beam which is picked up as a result of projecting the measuring light beam while rotating the measurement section at a measurement point of the measurement target; a distance detecting step of detecting a distance between the measurement target and the circumferential wall of the optical probe; a contact point judging step of judging an area in which the distance between the circumferential wall of the optical probe and the surface of the measurement target is equal to or smaller than a given value as an area where the optical probe is in contact with the measurement target; and a contact area detecting step of detecting a contact area in which the circumferential wall of the optical probe and the surface of the measurement target are in contact with each other from a result of the judging in the contact point judging step.

Preferably, in the measurement target position detecting step, a peak point where intensity of the reflected light beam exceeds a given threshold outside of the circumferential wall of the optical probe is detected as the surface of the measurement target.

It is preferable that the contact area detecting method further comprises a distance setting step of setting a distance for judging that the optical probe is in contact with the measurement target.

In order to attain yet the other object described above, the present invention provides an image processing method for obtaining a tomographic image of a measurement target, comprising: a contact area setting step of using the contact area detecting method described above to detect and set the contact area in which the optical probe and the measurement target are in contact with each other; an interference signal obtaining step of creating the interference light beam from a reflected light beam which is picked up while rotating the measurement section, and obtaining the interference light beam as interference signals; and a tomographic image obtaining step of obtaining the tomographic image by processing only the interference signals of the contact area detected in the contact area detecting step.

It is preferable that the image processing method further comprises a display step of performing one of rotation processing and enlarging processing on the obtained tomographic image and then displaying the processed tomographic image on a screen.

Further, in order to attain the other object described above, the present invention provides an optical tomographic image obtaining method for obtaining a tomographic image of a measurement target from an interference light beam created by combining a reference light beam with a reflected light beam which is reflected by the measurement target irradiated with a measuring light beam and which is picked up by a measurement section placed at a tip of an optical probe, the measurement section being rotated while irradiating the measurement target with the measuring light beam, the method comprising: a contact area detecting step of detecting a state of contact between a circumferential wall of the optical probe and the measurement target, and detecting a contact area from a result of the detection of the state of contact; an interference signal obtaining step of creating the interference light beam from the reflected light beam of the measuring light beam which is picked up while rotating the measurement section, and obtaining the interference light beam as interference signals; and a tomographic image obtaining step of obtaining the tomographic image by processing the interference signals under a first processing condition when the interference signals are created from a first reflected light beam that is reflected by the measurement target in the contact area, and under a second processing condition when the interference signals are created from a second reflected light beam that is reflected by the measurement target in other areas than the contact area, wherein the first processing condition is a condition that makes processing accuracy higher than the second processing condition does.

Preferably, the first processing condition is a condition that makes a processing amount for one interference signal larger than the second processing condition does.

Preferably, the first processing condition is a condition that makes a count of interference signals processed per unit area larger than the second processing condition does.

It is preferable that the optical tomographic image obtaining method further comprises a condition setting step of setting the first processing condition and the second processing condition based on input information.

In addition, the present invention provides an optical tomographic image obtaining method for obtaining a tomographic image of a measurement target from an interference light beam created by combining a reference light beam with a reflected light beam which is reflected by the measurement target irradiated with a measuring light beam and which is picked up by a measurement section placed at a tip of an optical probe, the measurement section being rotated while irradiating the measurement target with the measuring light beam, the method comprising: a contact area detecting step of detecting a state of contact between a circumferential wall of the optical probe and the measurement target, and detecting a contact area from a result of the detection of the state of contact; a rotation setting step of calculating and setting rotation speed of the measurement section based on the contact area detected in the contact area detecting step; an interference signal obtaining step of creating the interference light beam from the reflected light beam of the measuring light beam, which is picked up while rotating the measurement section in accordance with settings set in the rotation setting step, and obtaining the interference light beam as interference signals; and a tomographic image obtaining step of obtaining the tomographic image by processing at least interference signals created from a first reflected light beam that is reflected by the measurement target in the contact area, wherein, in the rotation setting step, the rotation speed of the measurement section is set at least such that, when picking up the first reflected light beam of the contact area, the measurement section rotates at a different speed than when picking up a second reflected light beam of other areas than the contact area.

Preferably, in the rotation setting step, the rotation speed of the measurement section is set such that, when picking up the first reflected light beam of the contact area, the measurement section rotates at a lower speed than when picking up the second reflected light beam of the other areas than the contact area.

Preferably, in the rotation setting step, a rotation direction of the measurement section is calculated and set in addition to the rotation speed of the measurement section, and hence the measurement section moves back and forth in the contact area.

Preferably, the calculating and setting in the rotation setting step is performed based on, in addition to the contact area detected in the contact area detecting step, a set resolution of the tomographic image.

Preferably, in the tomographic image obtaining step, the tomographic image is obtained by processing a plurality of interference signals separately to obtain image signals and then performing noise reduction processing on the image signals.

Preferably, in the tomographic image obtaining step, the tomographic image is obtained by processing only interference signals that are created from the first reflected light beam of the measurement target in the contact area.

Preferably, the contact area detecting step includes:

a probe position obtaining step of detecting a position of the circumferential wall of the optical probe from a reflected light beam which is picked up as a result of projecting a measuring light beam from the measurement section; a measurement target position detecting step of detecting a position of a surface of the measurement target from a reflected light beam which is picked up as a result of projecting a measuring light beam while rotating the measurement section at a measurement point of the measurement target; a distance detecting step of detecting a distance between the measurement target and the circumferential wall of the optical probe; a contact point judging step of judging an area in which the distance between the circumferential wall of the optical probe and the surface of the measurement target is equal to or smaller than a given value as an area where the optical probe is in contact with the measurement target; and a contact area detecting step of detecting a contact area in which the circumferential wall of the optical probe and the surface of the measurement target are in contact with each other from a result of the judging in the contact point judging step.

Preferably, in the measurement target position detecting step, a peak point where intensity of the reflected light beam exceeds a given threshold outside of the circumferential wall of the optical probe is detected as the surface of the measurement target.

It is preferable that the optical tomographic image obtaining method further comprises a distance setting step of setting a distance for judging that the optical probe is in contact with the measurement target.

It is preferable that the optical tomographic image obtaining method further comprises a display step of performing one of rotation processing and enlarging processing on the obtained tomographic image and then displaying the processed tomographic image on a screen.

According to the first to third aspects of the present invention, by detecting the state of contact between the measurement section and the measurement target, an effective area where a high-resolution image will be obtained can be detected. An effective area can thus be recognized and selectively processed.

Further, processing only a contact area where the measurement section and the measurement target are judged as being in contact with each other reduces the amount of information to be processed. The amount of information to be processed is reduced by detecting whether or not the measurement section and the measurement target are in contact with each other and selectively processing information of an area where a high-resolution tomographic image can be obtained, while skipping information of a low-priority area where the reliability of an obtained tomographic image will be low. In this way, a high-resolution, high-quality tomographic image can be read.

According to the fourth and fifth aspects of the present invention, the state of contact between the measurement section and the measurement target is detected, a contact area where the measurement section and the measurement target are judged as being in contact with each other is processed under a processing condition different from that of other areas, and the processing condition of the contact area is set such that a tomographic image of higher precision is obtained. A high-resolution tomographic image of an area to be diagnosed, tested, or the like can thus have high precision.

In addition, the overall structure of the surroundings of the measurement section can be grasped as well if low-precision tomographic images of other areas than the contact area are obtained.

Further, the amount of information to be processed can be reduced by setting a low-precision condition to other areas than the contact area. Reducing the amount of information to be processed can speed up the processing and cut the measurement time short.

A tomographic image suitable for diagnostic, testing, and other uses can thus be obtained while quickening the processing and shortening the measurement time.

According to the sixth and seventh aspects of the present invention, a high-resolution tomographic image of an area to be diagnosed, tested, or the like can be obtained by detecting the state of contact between the measurement section and the measurement target and capturing a sectional image of at least a contact area where the measurement section and the measurement target are judged as being in contact with each other.

In addition, by rotating the measurement section in the contact area at a speed different from the one in other areas, the number of interference signals to be obtained can be adjusted based on the location. The quality of a tomographic image to be obtained can thus be adjusted based on the location.

Further, the amount of information to be processed is reduced by detecting whether or not the measurement section and the measurement target are in contact with each other and selectively processing information of an area where a high-resolution tomographic image can be obtained, while skipping information of a low-priority area where the reliability of an obtained tomographic image will be low. In this way, a high-resolution, high-quality tomographic image suitable for diagnostic, testing, and other uses can be read.

Further, by rotating the measurement section at high speed in an area of which a tomographic image is not obtained, or by turning the measurement section with respect to an area of which a tomographic image is obtained, the scanning speed can be improved and a high-precision tomographic image can be obtained in a short period of time, or frequently.

BRIEF DESCRIPTION OF THE DRAWINGS

In the accompanying drawings:

FIG. 7 is a flow chart showing a method of detecting a position of a circumferential wall of the optical probe;

FIG. 17 is a block diagram showing a schematic structure of still another embodiment of the optical tomography imaging system according to the fifth aspect of the present invention;

DETAILED DESCRIPTION OF THE PREFERRED EMBODIMENTS

A detailed description is given through embodiments illustrated in the accompanying drawings on a contact area detecting method, an image processing method that uses the contact area detecting method, an optical tomography imaging system, and an optical tomographic image obtaining method according to the present invention.

Figure 1:
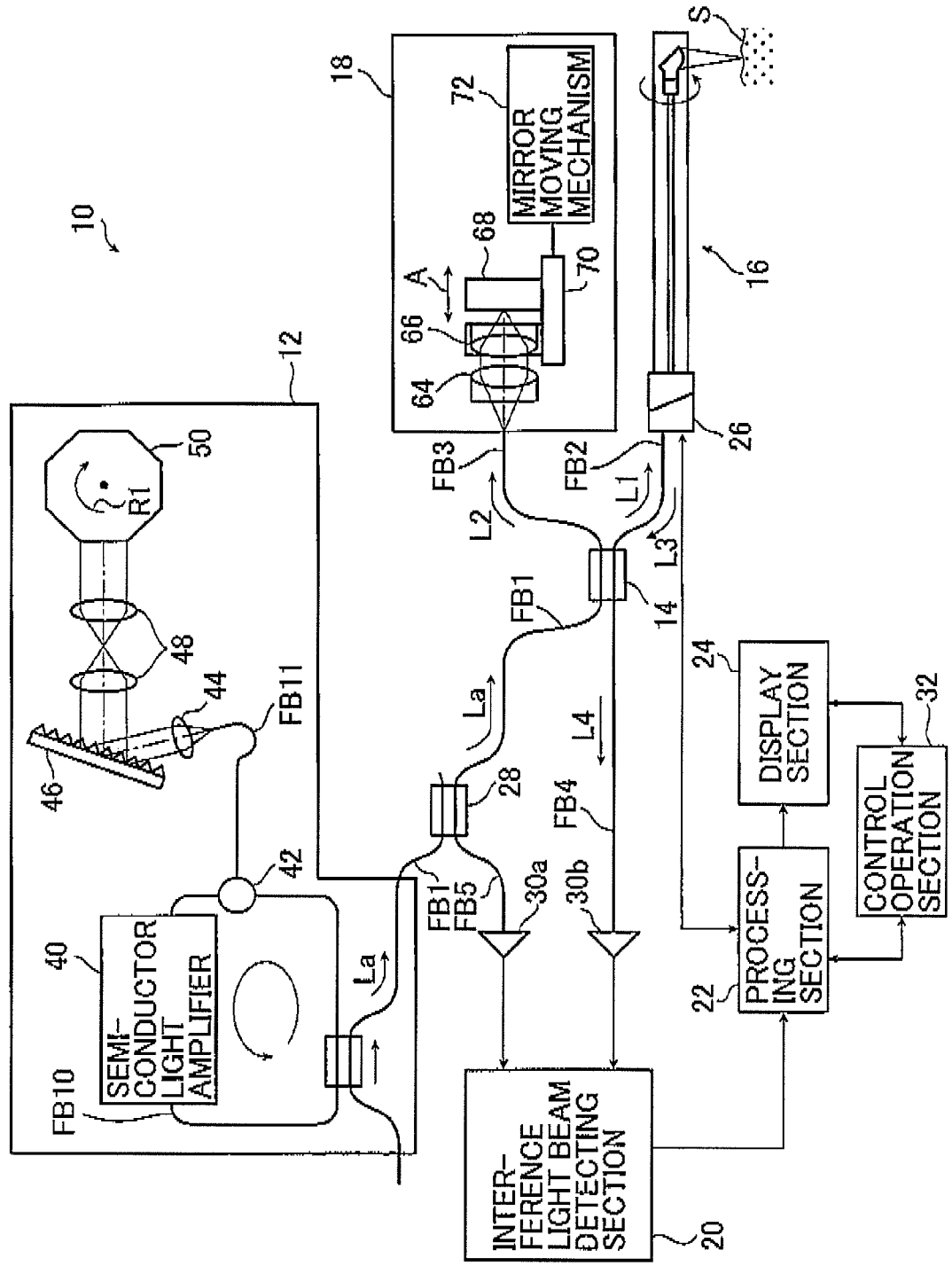
FIG. 1 is a block diagram showing a schematic structure of an embodiment of an optical tomography imaging system according to the first aspect of the present invention which employs a contact area detecting method according to the second aspect of the present invention and an image processing method according to the third aspect of the present invention.
Figure 2:
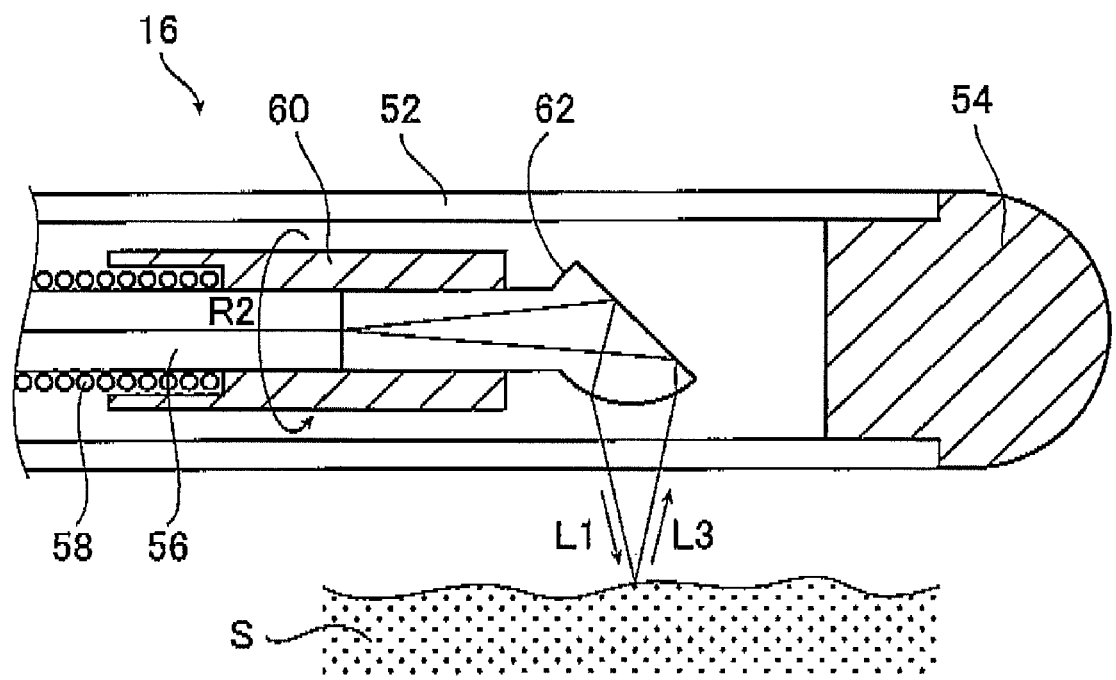
FIG. 2 is a partial sectional view showing an enlarged tip of an optical probe of the optical tomography imaging system shown in FIG. 1.
Figure 3:
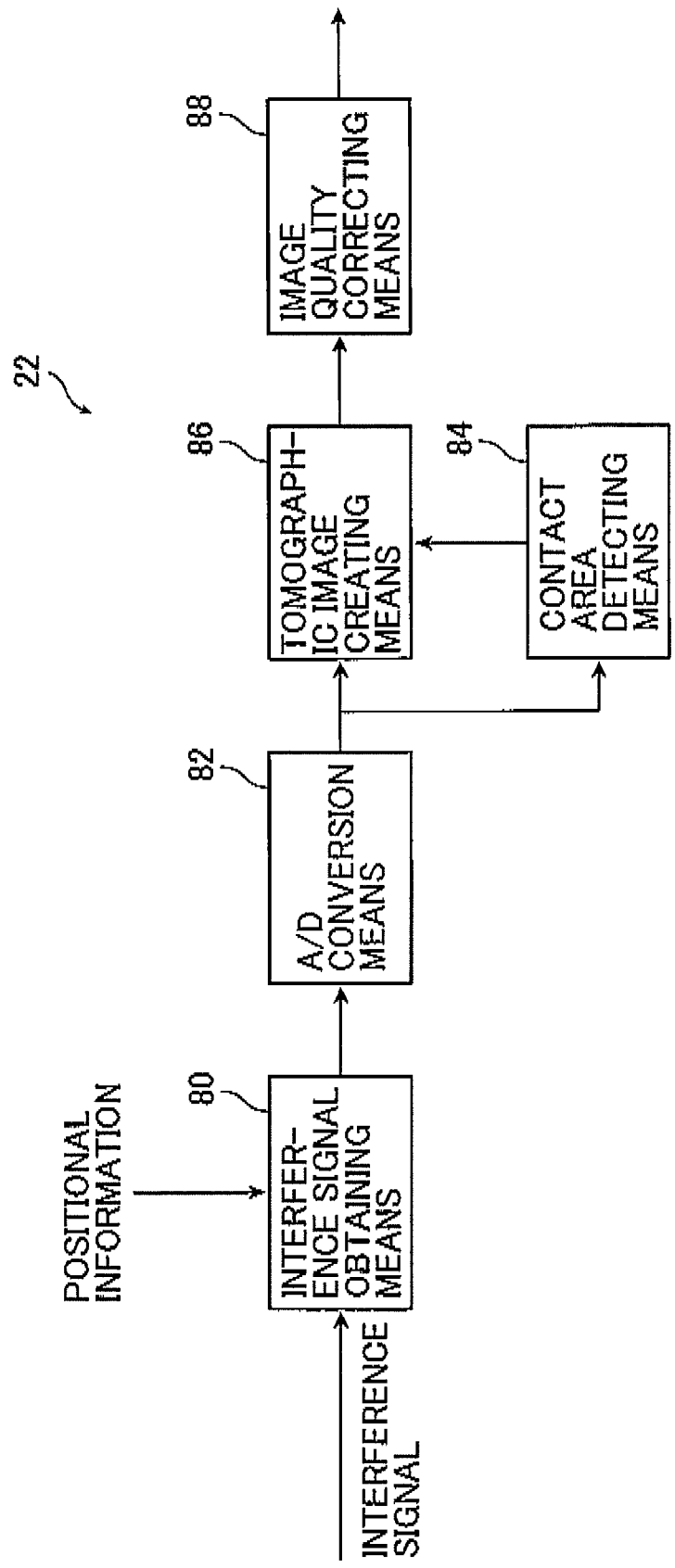
FIG. 3 is a block diagram showing a schematic structure of a processing section of the optical tomography imaging system shown in FIG. 1.

FIG. 1 is a block diagram showing a schematic structure of an embodiment of an optical tomography imaging system 10 according to the first aspect of the present invention which employs a contact area detecting method according to the second aspect of the present invention and an image processing method according to the third aspect of the present invention. FIG. 2 is a partial sectional view showing an enlarged tip of an optical probe 16 of the optical tomography imaging system 10 shown in FIG. 1. FIG. 3 is a block diagram showing a schematic structure of a processing section 22 of the optical tomography imaging system 10 shown in FIG. 1.

As shown in FIG. I, the optical tomography imaging system 10 has a light source unit 12, which emits a light beam, a branching/multiplexing section 14, which branches the light beam emitted from the light source unit 12 into a measuring light beam and a reference light beam and which combines a reflected light beam with the reference light beam to create an interference light beam, an optical probe 16, which guides the measuring light beam to irradiate a measurement target with the measuring light beam and obtain a light beam reflected by the measurement target, a light path length adjusting section 18, which adjusts the light path length of the reference light beam, an interference light beam detecting section 20, which detects the interference light beam created by the branching/multiplexing section 14 as an interference signal, a processing section 22, which processes the interference signal detected by the interference light beam detecting section 20, and a display section 24, which displays an optical tomographic image (hereinafter, also referred to as "tomographic image") obtained by the processing section 22. The optical tomography imaging system 10 also has a rotation driving section 26, which rotates a measurement section and others of the optical probe, an optical fiber coupler 28, which disperses a light beam emitted from the light source unit 12, a detector section 30a, which detects the reference light beam, a detector section 30b, which detects the reflected light beam, and a control operation section 32, which inputs various conditions to the processing section 22, the display section 24, and other components, changes settings, and performs other similar operations. An optical fiber is used as a path for light and guides light including the measuring light beam, the reference light beam, and the reflected light beam to relevant components.

The respective components are described below in detail.

The light source unit 12 has a semiconductor light amplifier 40, an optical brancher 42, a collimator lens 44, a diffraction grating element 46, an optical system 48, and a polygonal mirror 50, and emits a laser light beam La having frequency swept in a fixed cycle.

The semiconductor light amplifier (semiconductor gain medium) 40 emits weak emission light when a drive current is applied, and amplifies incident light. An optical fiber FB10 is connected to the semiconductor light amplifier 40. Specifically, one end of the optical fiber FB10 is connected to a part of the semiconductor light amplifier 40 from which light is emitted whereas the other end of the optical fiber FB10 is connected to a part of the semiconductor light amplifier 40 on which light is incident, with the result that light emitted from the semiconductor light amplifier 40 exits to the optical fiber FB10 and again enters the semiconductor light amplifier 40.

The semiconductor light amplifier 40 and the optical fiber FB10 thus form a light path loop and therefore act as an optical resonator. Accordingly, pulse-like laser light is generated when a drive current is applied to the semiconductor light amplifier 40.

The optical brancher 42 is put on a light path provided by the optical fiber FB10 and is connected to an optical fiber FB11 as well. The optical brancher 42 branches a light beam guided through the optical fiber FB10 so that part of the light beam enters the optical fiber FB11.

The collimator lens 44 is placed at the other end of the optical fiber FB11, namely, the end that is not connected to the optical fiber FB10, to make the light beam that exits the optical fiber FB11 into parallel beams.

The diffraction grating element 46 is placed at a given angle in the light path of the parallel beams created by the collimator lens 44. The diffraction grating element 46 disperses the parallel beams which exit the collimator lens 44.

The optical system 48 is placed in the light path of the light beam dispersed by the diffraction grating element 46. The optical system 48 includes a plurality of lenses to refract the light beam dispersed by the diffraction grating element 46 so as to make the refracted light beam into parallel beams.

The polygonal mirror 50 is placed in the light path of the parallel beams created by the optical system 48 to reflect the parallel beams. The polygonal mirror 50 is a revolving body that rotates at a constant speed in a direction indicated by an arrow R1 of FIG. 1. The polygonal mirror 50 has a shape of an equilateral octagon with respect to its rotation axis, and side faces irradiated with the parallel beams (faces that constitute the sides of the octagon) are reflective surfaces which reflect the irradiation light beam.

The polygonal mirror 50 rotates to change the angle of each reflective surface with respect to the optical axis of the optical system 48.

A light beam that exits the optical fiber FB11 travels through the collimator lens 44, the diffraction grating element 46, and the optical system 48, and is reflected by the polygonal mirror 50. The reflected light beam travels through the optical system 48, the diffraction grating element 46, and the collimator lens 44, and enters the optical fiber FB11.

Since the angle of the reflective surface of the polygonal mirror 50 changes with respect to the optical axis of the optical system 48 as described above, the angle at which the polygonal mirror 50 reflects the light beam at one time point differs from the angle at another time point. Therefore, of the light beam dispersed by the diffraction grating element 46, light in a specific frequency range alone reenters the optical fiber FB11. The light in a specific frequency range which reenters the optical fiber FB11 is determined by an angle formed between the optical axis of the optical system 48 and the reflective surface of the polygonal mirror 50. Accordingly, the frequency range of the light that reenters the optical fiber FB11 is varied depending on the angle between the optical axis of the optical system 48 and the reflective surface of the polygonal mirror 50.

The light in a specific frequency range incident on the optical fiber FB11 enters the optical fiber FB10 from the optical brancher 42 to be combined with light of the optical fiber FB10. The pulse-like laser light guided through the optical fiber FB10 thus becomes laser light in the specific frequency range, and this laser light beam La in the specific frequency range exits to an optical fiber FB1.

A wavelength λ of the light that reenters the optical fiber FB11 changes with time in a fixed cycle because the polygonal mirror 50 rotates at a constant speed in the direction indicated by the arrow R1. The frequency of the laser light beam La which exits to the optical fiber FB1 accordingly changes with time in a fixed cycle.

The light source unit 12 thus structured emits the frequency-swept laser light beam La to the optical fiber FB1.

The branching/multiplexing section 14 is constituted by, for example, a 2×2 optical fiber coupler, and is optically connected to the optical fiber FB1, an optical fiber FB2, an optical fiber FB3, and an optical fiber FB4.

The branching/multiplexing section 14 splits the incident laser light beam La which enters from the light source unit 12 through the optical fiber FB1 into a measuring light beam L1 and a reference light beam L2, and causes the measuring light beam L1 to enter the optical fiber FB2 while causing the reference light beam L2 to enter the optical fiber FB3.

The branching/multiplexing section 14 also combines the reference light beam L2 with a reflected light beam L3 reflected by a measurement target S after the reference light beam L2 is incident on the optical fiber FB3, then subjected to a frequency shift and a light path length change by the light path length adjusting section 18, which is described later, and travels back through the optical fiber FB3 to reenter the branching/multiplexing section 14, and after the reflected light beam L3 is picked up by the optical probe, which is described later, and enters the branching/multiplexing section 14 through the optical fiber FB2. The combined light exits the branching/multiplexing section 14 to the optical fiber FB4.

The optical probe 16 is connected to the optical fiber FB2 through the rotation driving section 26. The optical probe 16 irradiates the measurement target S with the incident measuring light beam L1 which enters the optical fiber FB2, picks up the reflected light beam L3 reflected by the measurement target S, and lets the picked-up a reflected light beam L3 exit to the optical fiber FB2.

The optical probe 16 has a probe sheath 52, a cap 54, an optical fiber 56, a spring 58, a fixing member 60, and an optical lens 62 as shown in FIG. 2.

The probe sheath 52 is a flexible tubular member and is formed from a material that is transmissive of the measuring light beam L1 and the reflected light beam L3. It is sufficient if part of the front end of the probe sheath 52 through which the measuring light beam L1 and the reflected light beam L3 travel (the opposite end to where the optical fiber FB2 is placed) is formed from a light-transmissive material (i.e., transparent material).

The cap 54 is provided at the front end of the probe sheath 52 (the opposite end to where the optical fiber FB2 is placed) to close the front end of the probe sheath 52.

The optical fiber 56 is a linear member housed inside the probe sheath 52 to run along the probe sheath 52. The optical fiber 56 guides the measuring light beam L1 upon exit from the optical fiber FB2 to the optical lens 62, and also guides the reflected light beam L3 to the optical fiber FB2 after the reflected light beam L3 is picked up by the optical lens 62 as a result of irradiating the measurement target S with the measuring light beam L1.

The optical fiber 56 and the optical fiber FB2 are connected to each other by a rotary joint or the like, and hence the two are optically connected so as not to transmit the rotation of the optical fiber 56 to the optical fiber FB2. The optical fiber 56 is disposed such that the probe sheath 52 does not prevent the optical fiber 56 from rotating freely.

The spring 58 is fixed to the circumferential wall of the optical fiber 56. The optical fiber 56 and the spring 58 are connected to the rotation driving section 26.

The optical lens 62 is placed at the tip of the optical fiber 56 (the opposite end to where the optical fiber FB2 is connected), and has a substantially ball-shaped front end in order to collect the measuring light beam L1 exiting the optical fiber 56 to the measurement target S.

The optical lens 62 irradiates the measurement target S with the measuring light beam L1 exiting the optical fiber 56, and collects the reflected light beam L3 reflected by the measurement target S to make the reflected light beam L3 incident on the optical fiber 56.

The fixing member 60 is placed around a junction between the optical fiber 56 and the optical lens 62 to fix the optical lens 62 to an end of the optical fiber 56. How the fixing member fixes the optical lens 62 to the optical fiber 56 is not particularly limited, and the fixing member may fix the two with the use of adhesive which bonds the fixing member, the optical fiber 56, and the optical lens 62 together, or with the use of a mechanical structure such as a bolt.

The rotation driving section 26, which is connected to the optical fiber 56 and the spring 58, rotates the optical fiber 56 and the spring 58, to thereby rotate the optical lens 62 in a direction indicated by an arrow R2 with respect to the probe sheath 52. The rotation driving section 26 also has a rotary encoder (not shown), and detects the irradiation point of the measuring light beam L1 from positional information (angle information) of the optical lens 62 based on a signal from the rotary encoder. In other words, the rotation driving section 26 detects a measurement point by detecting an angle in the rotation direction of the revolving optical lens 62 with respect to a reference point.

The optical probe 16 thus structured irradiates the measurement target S with the measuring light beam L1 which exits the optical lens 62 when the rotation driving section 26 rotates the optical fiber 56 and the spring 58 in the direction of the arrow R2 of FIG. 2, by running the measuring light beam L1 in the direction of the arrow R2 (the circumferential direction of the probe sheath 52), and picks up the resultant reflected light beam L3.

In this way, the reflected light beam L3 reflected by the measurement target S can be picked up in all 360° directions around the probe sheath 52.

The light path length adjusting section 18 is placed at an end of the optical fiber FB3 from which the reference light beam L2 exits (the opposite end of the optical fiber FB3 to the branching/multiplexing section 14).

The light path length adjusting section 18 has a first optical lens 64, which turns light that exits the optical fiber FB3 into parallel beams, a second optical lens 66, which collects the light turned into parallel beams by the first optical lens 64, a reflecting mirror 68, which reflects the light collected by the second optical lens 66, a base 70, which supports the second optical lens 66 and the reflecting mirror 68, and a mirror moving mechanism 72, which moves the base 70 in a direction parallel to the optical axis direction. The light path length adjusting section 18 adjusts the light path length of the reference light beam L2 by varying the distance between the first optical lens 64 and the second optical lens 66.

The first optical lens 64 turns the reference light beam L2 exiting (a core of) the optical fiber FB3 into parallel beams, and also collects the reference light beam L2 reflected by the reflecting mirror 68 to the optical fiber FB3.

The second optical lens 66 collects the reference light beam L2 turned into parallel beams by the first optical lens 64 to the reflecting mirror 68, and also turns the reference light beam L2 reflected by the reflecting mirror 68 into parallel beams. The first optical lens 64 and the second optical lens 66 thus constitute a confocal optical system.

The reflecting mirror 68 is placed at the focal point of light collected by the second optical lens 66 and reflects the reference light beam L2 collected by the second optical lens 66.

In this way, the reference light beam L2 exiting the optical fiber FB3 is turned into parallel beams by the first optical lens 64 and collected by the second optical lens 66 to the reflecting mirror 68. The reference light beam L2 is then reflected by the reflecting mirror 68, turned into parallel beams by the second optical lens 66, and collected to the optical fiber FB3 by the first optical lens 64.

The base 70 fixes the second optical lens 66 and the reflecting mirror 68. The mirror moving mechanism 72 moves the base 70 in the direction of the optical axis of the first optical lens 64 (a direction indicated by an arrow A of FIG. 1).

By moving the base 70 in the direction of the arrow A with the mirror moving mechanism 72, the distance between the first optical lens 64 and the second optical lens 66 can be varied and the light path length of the reference light beam L2 can thus be adjusted.

The interference light beam detecting section 20 is connected to the optical fiber FB4 and detects, as an interference signal, an interference light beam L4 which is created in the branching/multiplexing section 14 by combining the reference light beam L2 with the reflected light beam L3.

The optical tomography imaging system 10 has the optical fiber coupler 28, which branches the laser light beam La so that part of the laser light beam La enters an optical fiber FB5 from the optical fiber FB1, the detector section 30a, which is provided to the optical fiber FB5 branched from the optical fiber coupler 28 and detects the light intensity of the branched laser light beam La, and the detector section 30b, which detects the light intensity of the interference light beam L4 on a light path provided by the optical fiber FB4.

Based on detection results of the detector section 30a and the detector section 30b, the interference light beam detecting section 20 adjusts the balance of the light intensity of the interference light beam L4 detected in the optical fiber FB4.

The processing section 22 detects, from an interference signal detected by the interference light beam detecting section 20, an area where the optical probe 16 and the measurement target S are in contact with each other at a measurement point, more strictly, an area that is deemed as where the surface of the probe sheath 52 of the optical probe 16 is in contact with the surface of the measurement target S. The processing section 22 also obtains a tomographic image from an interference signal detected by the interference light beam detecting section 20.

As shown in FIG. 3, the processing section 22 has interference signal obtaining means 80, A/D conversion means 82, contact area detecting means 84, tomographic image creating means 86, and image correcting means 88.

The interference signal obtaining means 80 obtains an interference signal detected by the interference light beam detecting section 20 and also obtains information on a measurement point detected by the rotation driving section 26, specifically, positional information of a measurement point detected from information on the position in the rotation direction of the optical lens 62, to associate the interference signal and the positional information of the measurement point with each other.

Figure 4:
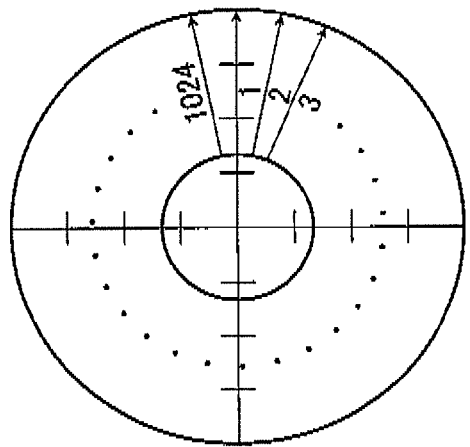
FIG. 4 is an explanatory diagram illustrating positional information about points of measurement by the optical probe.

FIG. 4 is an explanatory diagram illustrating positional information of an optical probe measurement point.

In this embodiment, the measurement count per rotation of the optical lens 62 is determined from the rotation speed of the optical lens 62 and the sweeping cycle in which the frequency of the measuring light beam L1 is swept. The number of times interference signals are obtained per rotation of the optical lens 62 is 1024 in this embodiment. The optical lens 62 rotates at a constant speed and interference signals are obtained regularly (the frequency of the measuring light beam L1 is swept in a fixed cycle).

The position of the measuring light beam L1, namely, the measurement point, therefore moves about the center of rotation by a given angle from n=1 as shown in FIG. 4. Since the point at which interference signals are obtained thus moves by a given angle, each interference signal measurement point can be assigned a line number n. A measurement point assigned with a line number n=1024 and a measurement point assigned with a line number n=1 are adjacent to each other because the optical lens 62 revolves.

The interference signal associated with the positional information of a measurement point is sent to the A/D conversion means 82.

The A/D conversion means 82 converts the interference signal associated with the positional information of a measurement point and output as an analog signal by the interference signal obtaining means 80 into a digital signal.

The interference signal associated with the positional information of a measurement point and converted into a digital signal is sent to the contact area detecting means 84 and the tomographic image creating means 86.

The contact area detecting means 84 performs fast Fourier transform (FFT) on the interference signal converted into a digital signal by the A/D conversion means 82 to obtain a relation between the frequency component and intensity of the interference signal. The frequency component in the detected frequency component-intensity relation is associated with the depth direction (a direction away from the center of rotation) to obtain information on a relation between the depth direction and the intensity. From the information on the depth direction-intensity relation, the contact area detecting means 84 detects the position of the surface of the probe sheath 52 at a point where the measuring light beam L1 passes through the probe sheath 52 (hereinafter, referred to as "position of the circumferential wall of the probe"), and an area of contact between the probe sheath 52 and the measurement target S at the point where the measuring light beam L1 passes through the wall of the probe sheath 52.

Detection of the position of the circumferential wall of the probe is described.

Figure 5:
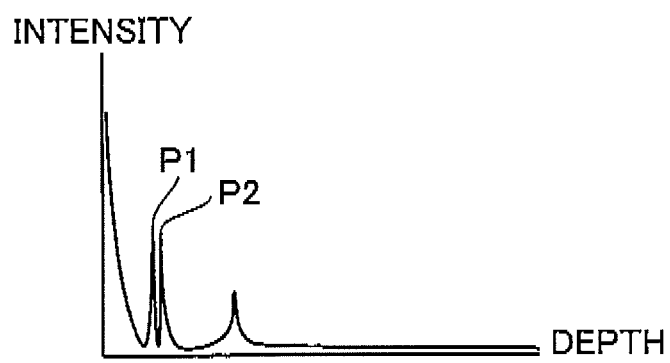
FIG. 5 is a graph showing a schematic example of a calculation result of fast Fourier transform (FFT) of interference signals.

First, FFT is performed on arbitrarily chosen one line of interference signals to obtain information on a frequency component-intensity relation, which is processed to obtain information on a depth direction-intensity relation. FIG. 5 is a graph showing a schematic example of a calculation result of FFT of interference signals. In FIG. 5, the axis of abscissa represents depth direction and the axis of ordinate represents intensity.

As shown in FIG. 5, a point at which the intensity is high and a point at which a peak of the intensity (hereinafter, simply referred to as "peak") is detected are where a change in physical properties occurs, in other words, a boundary between the air and a material or between materials having properties different from each other. The peak is not limited to a particular definition and can be set in various ways. For example, the peak may be detected when the intensity is equal to or larger than a certain value, or when the amount of change in intensity reaches a certain level or higher.

What first reflects the measuring light beam L1 after the measuring light beam L1 exits the optical lens 62 is the probe sheath 52. Therefore, the first peak point, namely, a peak detected at a point closest to the optical lens 62 (a peak P1 of FIG. 5) represents the position of the circumferential wall of the probe.

The optical lens 62 and the probe sheath 52 are arranged concentrically about the center of rotation, which makes the distance between the center of rotation of the optical lens 62 and the position of the circumferential wall of the probe constant wherever the measurement point is located. Accordingly, the position of the circumferential wall of the probe that is detected on one line of interference signals can be treated as the position of the circumferential wall of the probe at any point along the entire circumferential length of the probe.

The contact area detecting means 84 detects the position of the circumferential wall of the probe in this manner.

Described next is about detection of an area of contact in which a part of the probe sheath 52 where the measuring light beam L1 passes through and the measurement target S are in contact with each other (hereinafter, simply referred to as "contact area in which the probe sheath 52 and the measurement target S are in contact with each other").

First, as in the detection of the position of the circumferential wall of the probe, FFT is performed on one line of interference signals to obtain information on the depth direction.

As a result, a plurality of peaks are detected in the depth direction as in the graph of FIG. 5.

Among the plurality of peaks detected, the first peak (the peak P1 of FIG. 5) is a peak where the probe sheath is detected, and a peak closest to this peak where the probe sheath is detected (a peak P2 of FIG. 5) corresponds to the surface of the measurement target. In short, a peak point second closest to the center of rotation (second shallowest) represents the position of the surface of the measurement target S.

The distance between the detected surface of the measurement target S and the circumferential wall of the probe is detected next. When the detected distance is equal to or smaller than a threshold, it is judged that the measurement target S and the circumferential wall of the probe are in contact with each other. When the detected distance is larger than the threshold, it is judged that the measurement target S and the circumferential wall of the probe are not in contact with each other.

The next line is processed in the same manner. FFT is performed on the interference signals, a peak closest to a peak where the probe sheath is detected is detected as the position of the surface of the measurement target S, and the distance between the surface of the measurement target S and the circumferential wall of the probe is detected to judge whether or not the two are in contact with each other.

This judging is conducted for each line, and hence the state of contact between the measurement target S and the circumferential wall of the probe is judged along the entire circumferential length of the measurement area.

Next, a contact area in which the probe sheath 52 and the measurement target S are in contact with each other is detected based on results of judging of the state of contact between the measurement target S and the circumferential wall of the probe along the entire circumferential length.

Figure 6A:
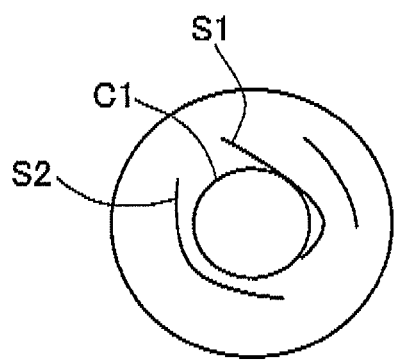
FIGS. 6A and 6B are explanatory diagrams illustrating a method of detecting a contact area.
Figure 6B:
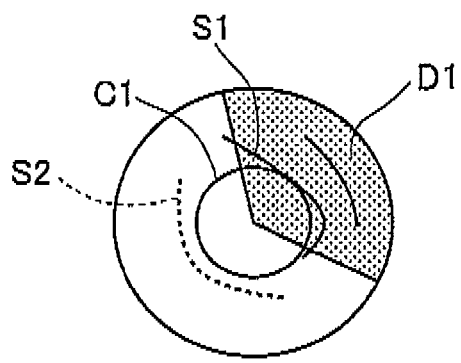

A specific description is given with reference to FIGS. 6A and 6B. FIGS. 6A and 6B are explanatory diagrams illustrating a contact area detecting method. A circle C1 of FIGS. 6A and 6B represents the circumferential wall of the probe.

As shown in FIG. 6A, surfaces S1 and S2 of the measurement target S are detected by detecting peaks along the entire circumferential length. The surface S1 contains a portion in which the probe sheath 52 and the measurement target S are in contact with each other, whereas the rest of the measurement area including the surface S2 is apart from the probe sheath 52.

In this case, as shown in FIG. 6B, the contact area detecting means 84 detects an area D1 which is a given extent of area centered around the contact portion of the surface S1 as a contact area in which the probe sheath 52 and the measurement target S are in contact with each other.

Information on the detected contact area in which the probe sheath 52 and the measurement target S are in contact with each other is sent to the tomographic image creating means 86.

The tomographic image creating means 86 obtains a tomographic image in the depth direction by processing the information on the frequency component-intensity relation which is obtained through fast Fourier transform (FFT) of interference signals converted into digital signals by the A/D conversion means 82.

The tomographic image creating means 86 uses the contact area information sent from the contact area detecting means 84 to obtain a tomographic image for only interference signals of positional information of an area judged as the contact area, and does not obtain a tomographic image for interference signals of positional information of other areas than the contact area. In short, the tomographic image creating means 86 performs mask processing instead of processing of obtaining an image through FFT or from results of FFT.

A brief description is given on image creation in the tomographic image creating means 86. Details thereof are described in an article titled "optical frequency scanning spectrum interference microscope" and written by Mitsuo Takeda in Optical and Electro-Optical Engineering Contact, 2003, Vol. 41, No. 7, p 426-p 432.

When the measurement target S is irradiated with the measuring light beam L1, the reflected light beam L3 from each depth point in the measurement target S interferes with the reference light beam L2 with a varying light path length difference 1. When the light intensity of interference fringes at the light path length difference 1 is given as S(l), a light intensity I(k) of an interference signal detected by the interference light beam detecting section 20 is expressed as follows.

$$I(k)=\int_0^\infty s(l)[1+\cos(kl)]dl$$

where k represents the wave number and l represents the light path length difference. The above expression can be deemed as an interferogram of an optical frequency region in which the wave number k=ω/c is a variable. Accordingly, by performing FFT on spectral interference fringes detected by the interference light beam detecting section 20 and determining the light intensity S(l) of the interference light beam L4, the tomographic image creating means 86 can obtain information on the distance from the measurement start point of the measurement target S and reflection intensity information, and create a tomographic image.

The image correcting means 88 performs logarithmic transformation and radial transformation on tomographic images created by the tomographic image creating means 86, and arranges the images in order by line number to obtain a circular image with the center of rotation of the optical lens as the center of the circle.

The image correcting means 88 also performs sharpening processing, smoothing processing, and the like on a tomographic image to correct the image quality.

The image correcting means 88 sends the tomographic image that has been subjected to the image quality correction to the display section 24.

When to send the tomographic image is not particularly limited, and the image correcting means 88 may send a corrected tomographic image to the display section each time processing of one line is finished, and hence a displayed image of one line is overwritten with an image of another line. Alternatively, the image correcting means 88 may send one whole circular tomographic image to the display section after finishing processing all lines (after finishing processing of images that are obtained by rotating the optical lens by 360° once).

The display section 24 is a CRT, a liquid crystal display, or the like, and displays a tomographic image sent from the image correcting means 88.

The control operation section 32 has input means such as a keyboard and/or a mouse and control means which manages various conditions based on input information. The control operation section 32 is connected to the processing section 22 and the display section 24. The control operation section 32 responds to an instruction input by an operator through the input means by, for example, inputting the above-mentioned threshold and various processing conditions to the processing section 22, or setting or changing the threshold and the conditions, or changing the display settings of the display section 24. An operation window of the control operation section 32 may be displayed by the display section 24 or by a different display section. Further, the control operation section 32 may control the operation of and set various conditions of the light source unit 12, the light path length adjusting section 18, the interference light beam detecting section 20, the rotation driving section 26, and the detector sections 30a and 30b.

The optical tomography imaging system 10 basically has the above-mentioned structure.

Given next is a description on the operation of the optical tomography imaging system 10, which describes a contact area detecting method and an image processing method of the present invention in addition to an optical tomography imaging system of the present invention.

A method of obtaining an interference light beam and interference signals in measurement of the measurement target S is described first.

First, the mirror moving mechanism 72 moves the base 70 in the direction of the arrow A to adjust and set the light path length such that the measurement target S falls within the measurable area.

The light source unit 12 thereafter emits the laser light beam La. The emitted laser light beam La is split by the branching/multiplexing section 14 into the measuring light beam L1 and the reference light beam L2. The measuring light beam L1 is guided through the optical fiber FB2 and the optical probe 16 to irradiate the measurement target S.

Light reflected at each depth point in the measurement target S enters the optical probe 16 as the reflected light beam L3. The reflected light beam L3 enters the branching/multiplexing section 14 through the optical probe 16 and the optical fiber FB2.

The reference light beam L2, on the other hand, enters the light path length adjusting section 18 through the optical fiber FB3. After being adjusted in light path length by the light path length adjusting section 18, the reference light beam L2 is guided through the optical fiber FB3 to enter the branching/multiplexing section 14 again.

The branching/multiplexing section 14 combines the reflected light beam L3 reflected by the measurement target S with the reference light beam L2 with the light path length being adjusted by the light path length adjusting section 18. The interference light beam L4 is created between the reflected light beam L3 and the reference light beam L2, and is detected by the interference light beam detecting section 20 as an interference signal.

An interference light beam and interference signals are thus detected.

The following is a description on how an interference light beam detected by the above-mentioned method is processed.

Figure 8:
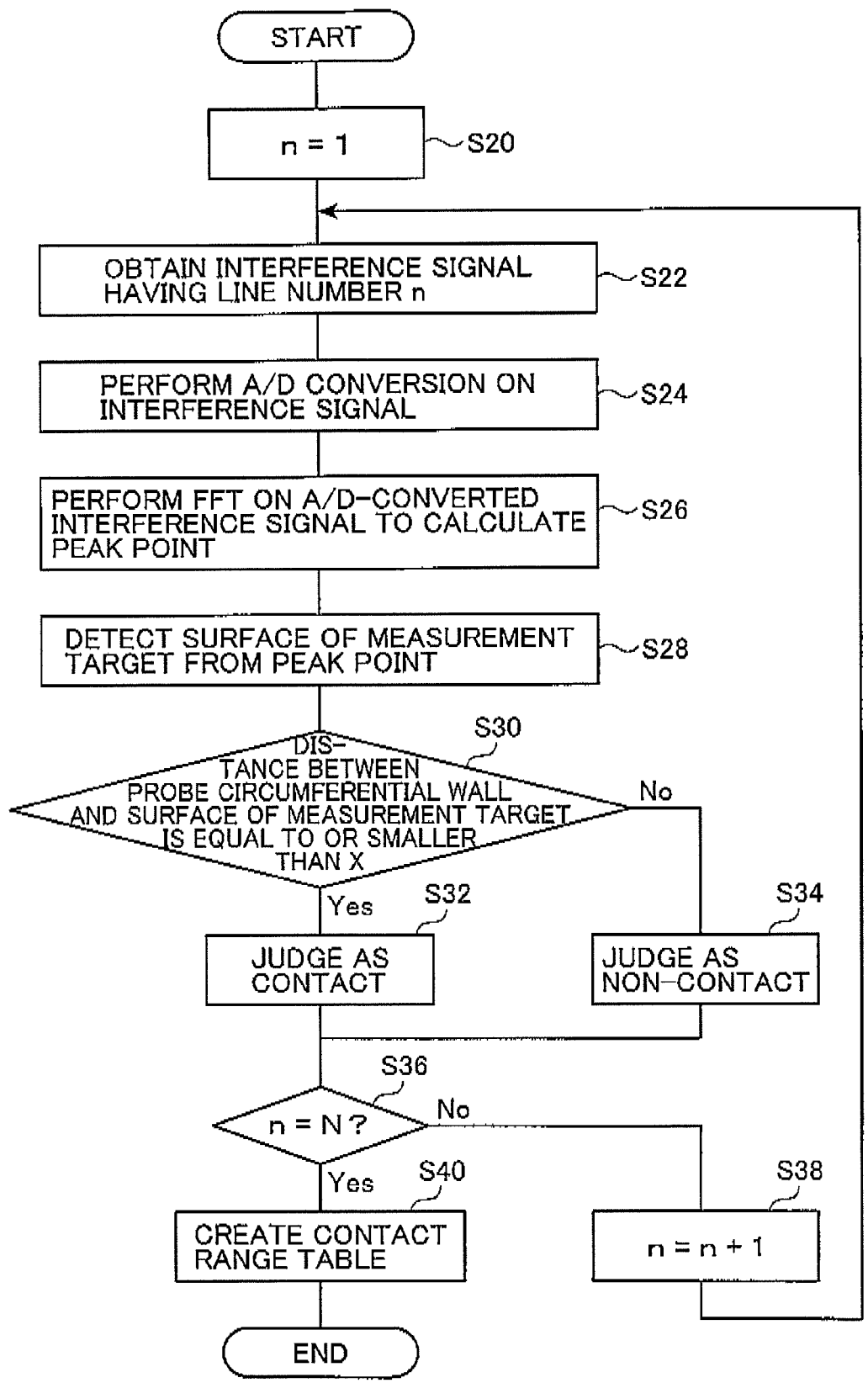
FIG. 8 is a flow chart showing the contact area detecting method.
Figure 9:
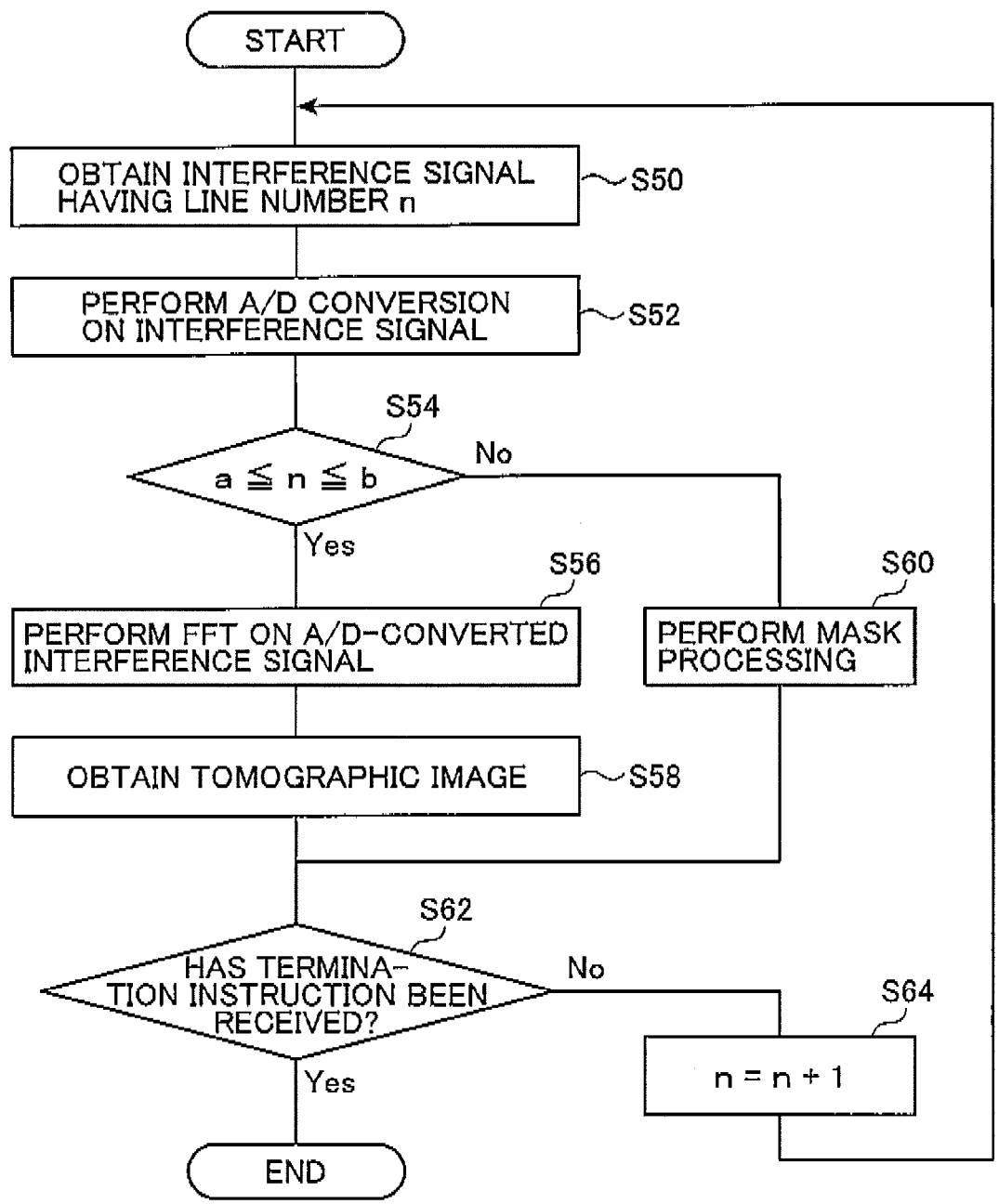
FIG. 9 is a flow chart showing the image processing method in which a tomographic image is calculated based on a detected contact area.

FIG. 7 is a flow chart showing a method of detecting the position of the circumferential wall of the probe. FIG. 8 is a flow chart showing a contact area detecting method. FIG. 9 is a flow chart showing an image processing method in which a tomographic image is calculated based on a detected contact area.

The method of detecting the position of the circumferential wall of the probe is described with reference to FIG. 7.

First, interference signals of arbitrarily chosen one line are obtained (Step S10). Specifically, the interference light beam detecting section 20 detects, as an interference signal, the interference light beam L4 which is created by combining the reference light beam L2 and the reflected light beam L3 in the manner described above.

Next, A/D conversion is performed on the detected interference signals (Step S12). Specifically, the A/D conversion means 82 converts the interference signals which are analog signals into digital signals.

FFT ifs next performed on the interference signals converted by A/D conversion to obtain information on the frequency component-intensity relation. The information is further processed to obtain a relation between the depth direction and the intensity, which is used to detect peak points (Step S14). A peak point is a point at which light is reflected and, basically, an interface between materials as described above.

The position of the circumferential wall of the probe is detected from a detected peak point (Step S16).

Specifically, out of detected peak points, a peak detected at a point closest to the optical lens 62 is detected as the position of the circumferential wall of the probe.

The position of the circumferential wall of the probe is detected in this manner.

The method of detecting a contact area in which the probe sheath 52 and the measurement target S are in contact with each other is described next with reference to FIG. S.

First, the line number n is set to 1 (Step S20). The line number is a number assigned to each interference signal measurement point in positional order with respect to arbitrarily chosen one line as the reference. Accordingly, in this embodiment where interference signals are detected 1024 times during one rotation of the optical lens 62, lines numbered from 1 to 1024 are arranged at regular intervals (see FIG. 4 described above).

Next, interference signals having the line number n are obtained (Step S22). Specifically, the interference light beam detecting section 20 detects, as an interference signal, the interference light beam L4 which is created by combining the reference light beam L2 and the reflected light beam L3 in the manner described above. The line number of an interference signal can be known from the positional information associated with the interference signal by the interference signal obtaining means 80.

When the line number of the obtained interference signals is not n, the processing of obtaining interference signals is repeated until the interference signals having the line number n are obtained.

Next, A/D conversion is performed on the detected interference signals (Step S24). Specifically, the A/D conversion means 82 converts the interference signals which are analog signals into digital signals.

FFT is next performed on the interference signals converted by A/D conversion to detect peak points (Step S26). As described above, a peak point is a point at which light is reflected and, basically, an interface between materials.

The position of the surface of the measurement target S is detected from a detected peak point (Step S28).

Since other objects are not interposed between the measurement target S and the optical probe 16 in principle, a peak point closest to a point where the probe sheath is detected in Step S16, in other words, a peak point second closest to the center of rotation (the second shallowest point) is detected as the position of the surface of the measurement target S.

Next, the distance between the detected surface of the measurement target S and the circumferential wall of the probe is detected, and whether or not the detected distance is equal to or smaller than a threshold X is judged (Step S30).

When the detected distance is equal to or smaller than the threshold X, it is judged that the measurement target S and the circumferential wall of the probe are in contact with each other (Step S32), and the processing proceeds to Step S36. When the detected distance is larger than the threshold X, it is judged that the measurement target S and the circumferential wall of the probe are not in contact with each other (Step S34), and the processing proceeds to Step 536.

Whether or not the line number n is N is judged next (Step S36).

N represents the total line count (the count of all lines) and, in this embodiment, N=1024.

When the line number n is not N, n is set to n+1 (Step S38) and the processing moves to Step S22. By executing Step S22 after increasing n by 1, whether or not the circumferential wall of the probe and the measurement target are in contact with each other is judged for an adjacent line having one larger line number.

When the line number n is N, on the other hand, it means that the contact judging has been finished for every line, and a contact range table is created (Step S40).

In the contact range table, a contact area is detected as a given extent of area centered around an area in which the measurement target S and the circumferential wall of the probe are judged as being in contact with each other. For example, when it is judged that the measurement target S and the circumferential wall of the probe are in contact with each other from a line number (a+10) to a line number (b−30), an area from the line number a to the line number b is detected as a contact area. How the contact range table is set is determined in accordance with setting conditions input in advance.

After the contact range table is created in this manner, the processing is ended.

A contact area in which the circumferential wall of the probe and the measurement target are in contact with each other is thus detected.

An image processing method for creating a tomographic image is described next with reference to FIG. 9.

First, interference signals having the line number n which is an arbitrary line number are obtained (Step S50). Specifically, the interference light beam detecting section 20 detects, as an interference signal, the interference light beam L4 which is created by combining the reference light beam L2 and the reflected light beam L3 in the manner described above.

Next, A/D conversion is performed on the detected interference signals (Step S52). Specifically, the A/D conversion means 82 converts the interference signals which are analog signals into digital signals.

Whether or not the line number n is included in the contact range table created in Step S40, specifically, whether or not the line number n is between the line number a and the line number b which define the contact area, is judged next (Step S54). In short, whether or not $a \leq n \leq b$ is satisfied is judged, When the line number n satisfies $a \leq n \leq b$, FFT is performed on the interference signals converted by A/D conversion (Step S56).

From results of the FFT, a tomographic image for the line number n is obtained (Step S58).

The tomographic image is obtained from the results of the FFT by performing given processing as described above.

After the tomographic image is obtained, the processing proceeds to Step S62.

When the line number n does not satisfy $a \leq n \leq b$, in other words, when n is smaller than a or larger than b ($n \leq a$ or $b \leq n$), mask processing is performed (Step S60).

Through the mask processing, an all-black image or an invariable predetermined image is given as an image for the line number n, instead of performing FFT and the processing of obtaining a tomographic image.

After the mask processing is finished, the processing proceeds to Step S62.

Whether or not a termination instruction has been received is then judged (Step S62).

In the case where a termination instruction has not been received, n is set to n+1 (Step S64) and the processing moves to Step S50. By executing Step S50 after increasing n by 1, the tomographic image obtaining processing is performed for an adjacent line having one larger line number. When Step S64 makes n into N+1, n is set to 1 and the processing of obtaining a tomographic image is continued until a termination instruction is received (not shown).

When a termination instruction is received, the processing is ended.

A tomographic image of a measurement target is obtained in the manner described above.

The image information of the mask-processed area and tomographic images thus obtained are sent to the image correcting means to be subjected to image processing for preparation for display, such as radial transformation and sharpening processing. The processed image is sent to the display section 24, which then displays the image.

According to the present invention, by detecting a contact area in which a measurement target and the optical probe are in contact with each other with the contact area detecting means, an area where a high-resolution tomographic image will be detected can be detected and recognized. Processing only an area where a reliable, high-resolution image will be obtained is thus made possible as in this embodiment.

While mask processing is performed on other areas than a contact area in this embodiment, the present invention is not limited thereto and different image processing methods may be employed for a contact area and other areas. For example, tomographic images of all lines are obtained for a contact area whereas only tomographic images of given lines are obtained for an area that is not a contact area, skipping the rest of the line numbers. The rotation driving section 26 may vary the rotation speed and rotation direction of the optical fiber 56 and the optical lens 62 depending on the result of contact area detection. For example, the rotation speed and rotation direction may be controlled such that the optical fiber 56 and the optical lens 62 are moved back and forth in obtaining a tomographic image of a contact area while being moved at high speed for an area that is not a contact area.

Further, the present invention is not limited to using a contact area detection result to obtain a tomographic image. For example, a contact area may be displayed while being superimposed on a displayed tomographic image, or a tomographic image may be displayed along with the reliability of the tomographic image and the distance from the measurement target which are calculated from information on the contact state and detected contact area. Detecting a contact area and displaying the detection result enable an operator to readily recognize an area where a high-resolution image will be obtained.

The contact area detection makes it easier to judge the effectiveness of a specific part of a tomographic image.

The present invention also lessens the load on the processing section and shortens the processing time by obtaining only a tomographic image of a contact area and omitting image processing for an area that is not a contact area. In this way, video images can be displayed at high speed even with an inexpensive processor. A high-resolution tomographic image can thus be displayed while keeping the cost of the system low.

Information on a detected contact area is used to obtain a tomographic image of the contact area which is high in resolution and actually needed, while omitting image processing for an area of the measurement target that is apart from the optical probe and will provide a low-resolution, unclear image which is not very useful as a tomographic image. A tomographic image of the present invention can therefore be used effectively. Limiting the execution of image processing to a contact area also makes more sophisticated image processing of a tomographic image possible without increasing the overall information processing amount.

The optical tomography imaging system 10 employs swept source-OCT (SS-OCT) to obtain a tomographic image of a measurement target and detect an area of contact with the measurement target, but the present invention is not limited thereto.

Figure 10:
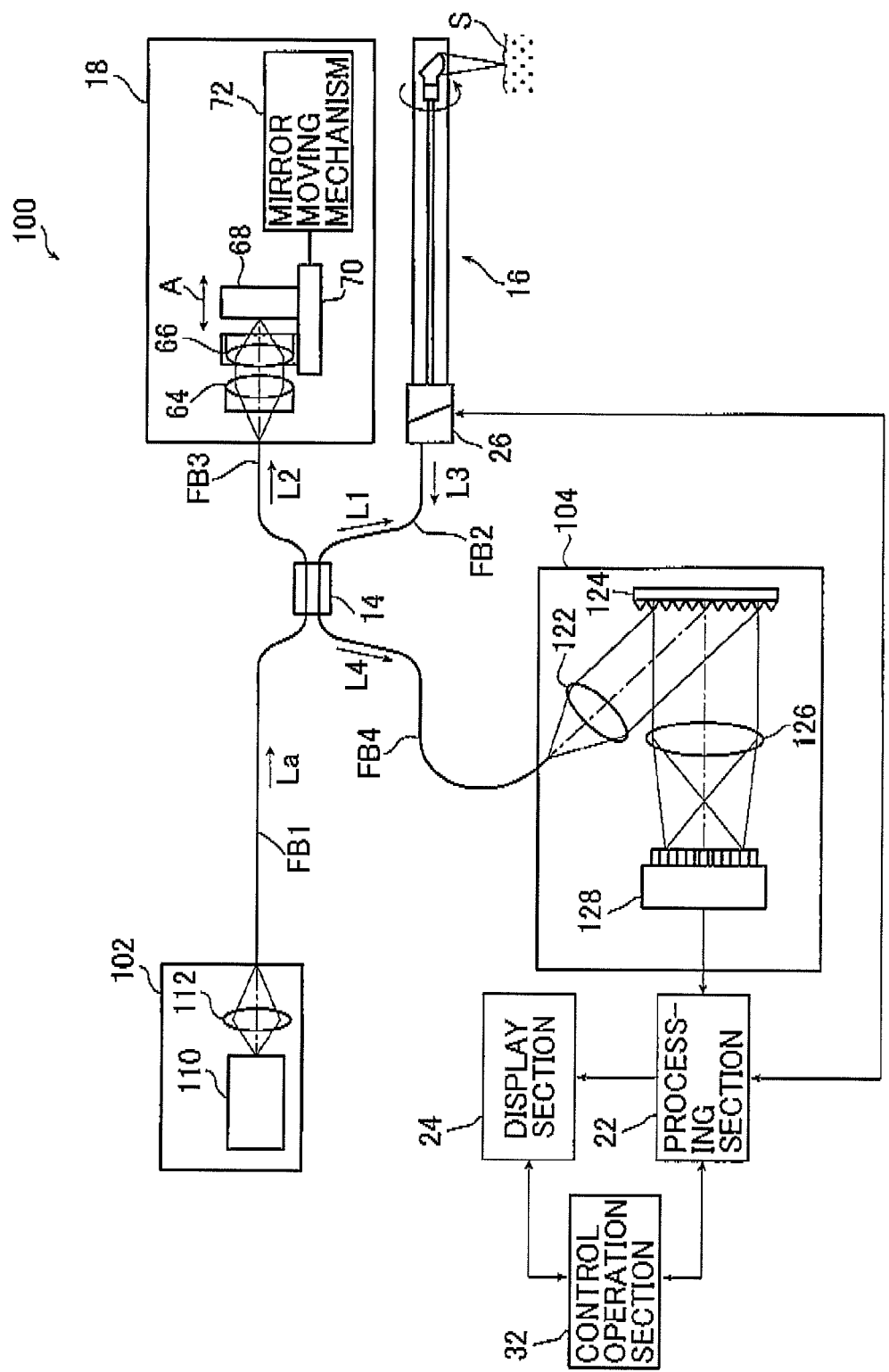
FIG. 10 is a block diagram showing a schematic structure of another embodiment of the optical tomography imaging system according to the first aspect of the present invention.

FIG. 10 is a block diagram schematically showing a schematic structure of another embodiment of the optical tomography imaging system.

The optical tomography imaging system shown in FIG. 10 is denoted by 100, and is the same as the optical tomography imaging system 10 except that spectral domain-OCT (SD-OCT) is employed to obtain a tomographic image of a measurement target and detect an area of contact with the measurement target. Components common to the optical tomography imaging system 100 and the optical tomography imaging system 10 are denoted by the same reference symbols and their detailed descriptions are omitted here. The following description focuses on features specific to the optical tomography imaging system 100.

The optical tomography imaging system 100 has a light source unit 102, which emits a light beam, the branching/multiplexing section 14, which branches the light beam emitted from the light source unit 102 into a measuring light beam and a reference light beam and which combines a reflected light beam with the reference light beam to create an interference light beam, the optical probe 16, which guides the measuring light beam to irradiate a measurement target with the measuring light beam and collect light reflected by the measurement target, the light path length adjusting section 18, which adjusts the light path length of the reference light beam, an interference light beam detecting section 104, which detects the interference light beam created by the branching/multiplexing section 14, the processing section 22, which processes results of detection obtained by the interference light beam detecting section 104, and the display section 24, which displays a tomographic image obtained by the processing section 22. The optical tomography imaging system 100 also has the rotation driving section 26, which rotates the measurement section and others of the optical probe, and the control operation section 32, which inputs various conditions to the processing section 22, the display section 24, and other components, changes settings, and performs other similar operations. An optical fiber is used as a path for light and guides light including the measuring light beam, the reference light beam, and the reflected light beam to relevant components.

The light source unit 102 has a light source 110 and an optical system 112 to emit the laser light beam La, which is incident on the optical fiber FB1.

The light source 110 is a light emitting device that emits a low coherence light beam, for example, a super luminescent diode (SLD), an amplified spontaneous emission (ASE), or a supercontinuum source which obtains broadband light by irradiating a non-linear medium with ultra-short pulse laser light.

The optical system 112 is placed in the light path of the light beam emitted from the light source 110 and collects the light beam emitted from the light source 110 to make the light beam incident on the optical fiber FB1.

The interference light beam detecting section 104 has a collimator lens 122, which turns the interference light beam L4 exiting the optical fiber FB4 into parallel beams, dispersing means 124, which disperses the interference light beam L4 having a plurality of wavelength ranges to disperse by wavelength range, a lens 126, which collects beams of the interference light beam L4 of different wavelength ranges generated as a result of dispersion by the dispersing means 124, and light detecting means 128, which detects the interference light beam L4 collected by the lens 126. The interference light beam detecting section 104 detects, as an interference signal, the interference light beam L4 which is created in the branching/multiplexing section 14 by combining the reflected light beam L3 and the reference light beam L2.

The dispersing means 124 is constituted by, for example, a diffraction grating element, and disperses the incident interference light beam L4, which then exits to the light detecting means 128.

The light detecting means 128 is constituted by a CCD in which photosensors are aligned one-dimensionally or two-dimensionally, or a similar element. The photosensors detect, as interference signals, beams of the interference light beam L4 dispersed in the above-mentioned manner on a wavelength range basis.

The interference light beam detecting section 104 sends the detected interference signals to the processing section 22.

The contact area detecting means 84 and tomographic image creating means 86 of the processing section 22 perform FFT on each beam of the dispersed interference light beam L4, thereby capable of calculating for each line a relation between the frequency component and the intensity. The frequency component-intensity relation is further processed to obtain a relation between the depth direction and the intensity, which is used to obtain peak points in the depth direction and the intensity distribution as in the optical tomography imaging system 10.

The contact area detecting means 84 detects a contact area in which the circumferential wall of the probe and the measurement target are in contact with each other from the detected peak points in the depth direction and intensity distribution, and the tomographic image creating means 86 obtains a tomographic image.

In this way, the optical tomography imaging system 100 employs a different method to obtain interference signals, but the same effects as in the optical tomography imaging system 10 are obtained in the optical tomography imaging system 100 by detecting a contact area in which the circumferential wall of the probe and a measurement target are in contact with each other with the contact area detecting means.

Figure 11:
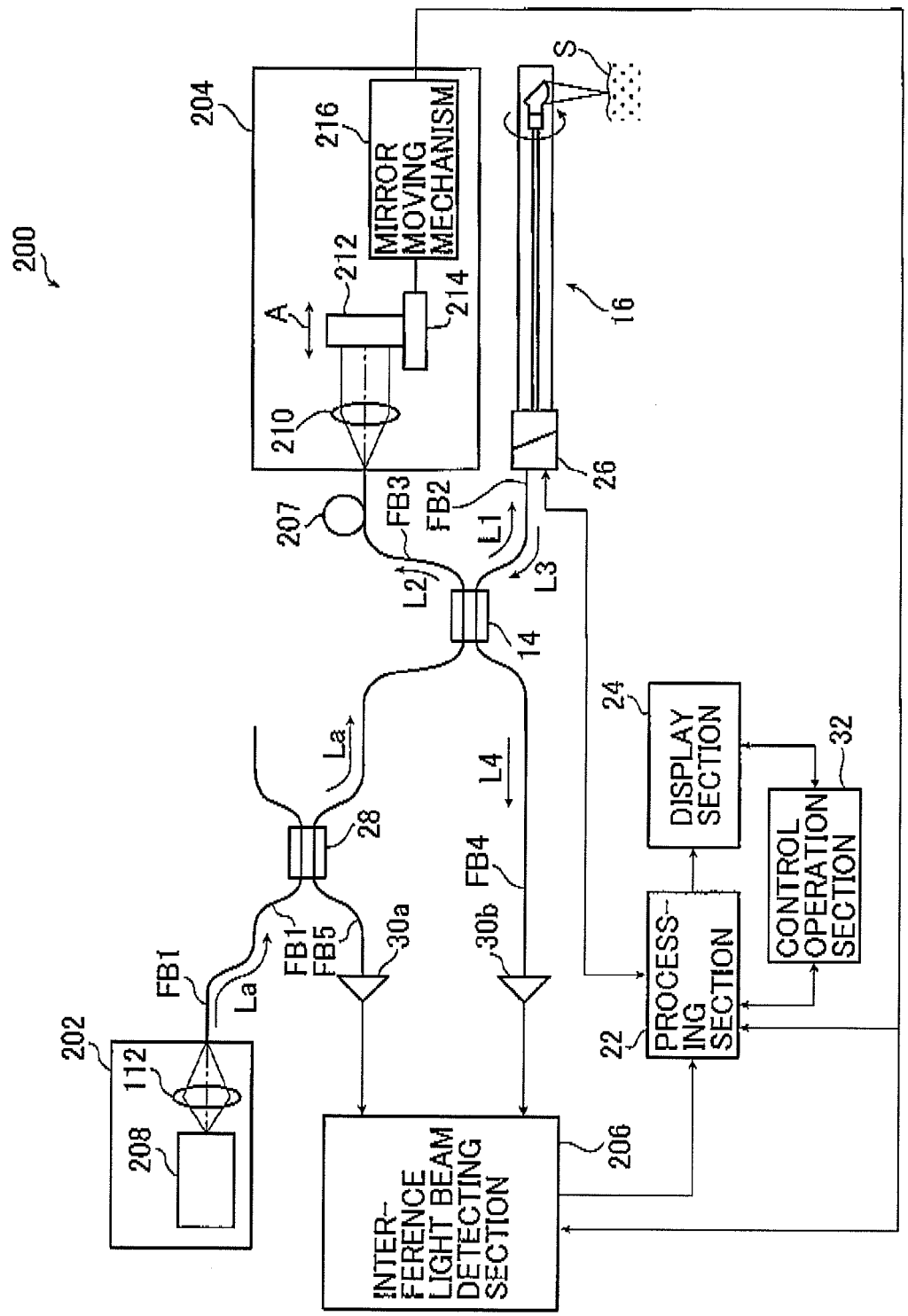
FIG. 11 is a block diagram showing a schematic structure of still another embodiment of the optical tomography imaging system according to the first aspect of the present invention.

FIG. 11 is a block diagram schematically showing a schematic structure of still another embodiment of the optical tomography imaging system.

An optical tomography imaging system shown in FIG. 11 is denoted by 200, and is the same as the optical tomography imaging system 10 except that time domain-OCT (TD-OCT) is employed to obtain a tomographic image of a measurement target and detect an area of contact with the measurement target. Components common to the optical tomography imaging system 200 and the optical tomography imaging system 10 are denoted by the same reference symbols and their detailed descriptions are omitted here. The following description focuses on features specific to the optical tomography imaging system 200, The optical tomography imaging system 200 has a light source unit 202, which emits a light beam, the branching/multiplexing section 14, which branches the light beam emitted from the light source unit 202 into a measuring light beam and a reference light beam and which combines a reflected light beam with the reference light beam to create an interference light beam, the optical probe 16, which guides the measuring light beam to irradiate a measurement target with the measuring light beam and collect light reflected by the measurement target, a light path length adjusting section 204, which adjusts the light path length of the reference light beam and changes the light path length periodically, an interference light beam detecting section 206, which detects the interference light beam created by the branching/multiplexing section 14, the processing section 22, which processes results of detection obtained by the interference light beam detecting section 206, and the display section 24, which displays a tomographic image obtained by the processing section 22. The optical tomography imaging system 200 also has the rotation driving section 26, which rotates the measurement section and others of the optical probe, the optical fiber coupler 28, which disperses a light beam emitted from the light source unit 202, the detector section 30a, which detects the reference light beam, the detector section 30b, which detects the reflected light beam, and the control operation section 32, which inputs various conditions to the processing section 22, the display section 24, and other components, changes settings, and performs other similar operations. An optical fiber is used as a path for light and guides light including the measuring light beam, the reference light beam, and the reflected light beam to relevant components.

The light source unit 202 has a light source 208 and the optical system 112 to make the laser light beam La incident on the optical fiber FB1.

The light source 208 is a light emitting device that emits the laser light beam La having a given wavelength.

The optical system 112 is placed in the light path of a light beam emitted from the light source 208 and collects the laser light beam La emitted from the light source 208 to make the laser light beam La incident on the optical fiber FB1.

The light path length adjusting section 204 has a collimator lens 210, which turns the reference light beam L2 exiting the optical fiber FB3 into parallel beams, a mirror 212, which is placed in the light path of the collimator lens 210 and which is movable in a direction indicated by the arrow A of FIG. 11, a base 214, which supports the mirror 212, and a mirror moving mechanism 216, which moves the base 214 in the direction of the arrow A of FIG. 11.

The light path length adjusting section 204 changes the light path length of the reference light beam L2 by moving the mirror 212 with the mirror moving mechanism 216 and thus varying the distance between the mirror 212 and the collimator lens 210. By moving the mirror 212 and changing the light path length of the reference light beam L2, the light path length adjusting section 204 changes the measurement point in the measurement target S in the depth direction.

A phase modulator 207 is placed in the light path of the reference light beam L2 (the optical fiber FB3), and gives a slight frequency shift to the reference light beam L2.

After being subjected to the light path length change and frequency shift in the light path length adjusting section 204, the reference light beam L2 is guided to the branching/multiplexing section 14.

The branching/multiplexing section 14 combines the reference light beam L2 with the reflected light beam L3 to create the interference light beam L4 as described above.

The interference light beam detecting section 206 employs, for example, heterodyne detection to detect the light intensity of the interference light beam L4 propagated through the optical fiber FB4 from the branching/multiplexing section 14. Specifically, when the sum of the total light path length of the measuring light beam L1 and the total light path length of the reflected light beam L3 is equal to the total light path length of the reference light beam L2, a beat signal that intensifies and weakens repetitively at a difference frequency between the reference light beam L2 and the reflected light beam L3 is generated. The beat signal acts as an interference signal in this embodiment.

The interference light beam detecting section 206 therefore detects beat signals, namely, interference signals, for each measurement point from the interference light beam L4, with the measurement point (depth) in the measurement target S varied by changes in light path length which are made by the light path length adjusting section 204. The measurement point is determined by the light path length of the reference light beam, and can accordingly be calculated from the position of the mirror. The light path length adjusting section 204 has a calculating section which calculates the measurement point from the mirror position, and outputs the calculated measurement point to the interference light beam detecting section 206 and the processing section 22.

The contact area detecting means 84 and tomographic image creating means 86 of the processing section 22 processes the beat signals detected for each measurement point, thereby calculating a relation between the measurement point (i.e., depth direction) and the intensity. From the calculated depth direction-intensity relation, peak points in the depth direction and the intensity distribution can be obtained as in the optical tomography imaging system 10.

The contact area detecting means 84 detects a contact area in which the-circumferential wall of the probe and the measurement target are in contact with each other from the detected peak points in the depth direction and intensity distribution, and the tomographic image creating means 86 obtains a tomographic image.

In this way, the optical tomography imaging system 200 employs a different method to obtain interference signals, but the same effects as in the optical tomography imaging system 10 can be obtained in the optical tomography imaging system 200 by detecting a contact area in which the circumferential wall of the probe and a measurement target are in contact with each other with the contact area detecting means.

An optical tomographic image obtaining method according to the fourth aspect of the present invention and an optical tomography imaging system according to the fifth aspect of the present invention are described in detail through embodiments illustrated in the accompanying drawings.

Figure 12:
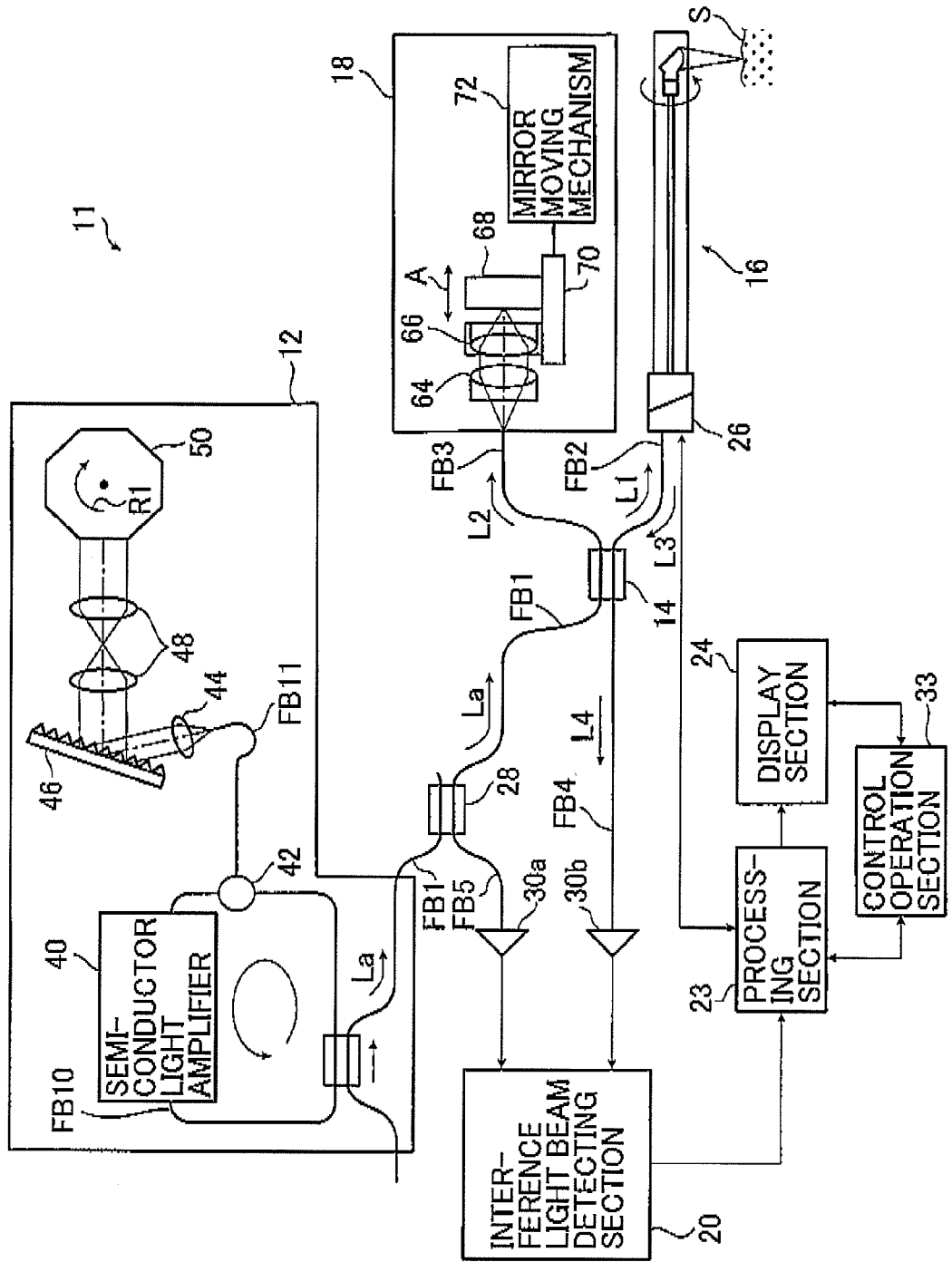
FIG. 12 is a block diagram showing a schematic structure of an embodiment of an optical tomography imaging system according to the fifth aspect of the present invention which employs an optical tomographic image obtaining method according to the fourth aspect of the present invention.
Figure 13:
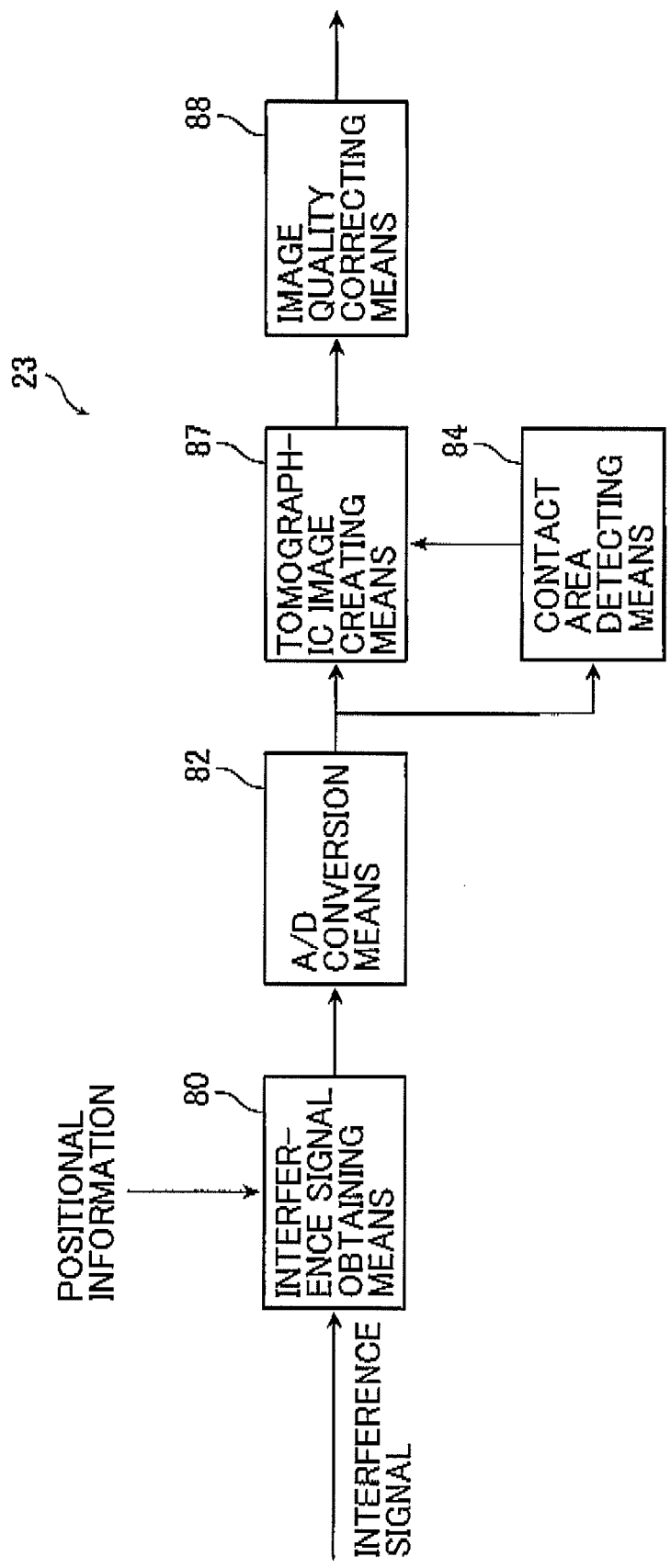
FIG. 13 is a block diagram showing a schematic structure of a processing section of the optical tomography imaging system shown in FIG. 12.

FIG. 12 is a block diagram showing a schematic structure of an embodiment of an optical tomography imaging system 11 according to the fifth aspect of the present invention which employs the optical tomographic image obtaining method according to the fourth aspect of the present invention. FIG. 13 is a block diagram showing a schematic structure of a processing section 23 of the optical tomography imaging system 11 shown in FIG. 12.

The optical tomography imaging system 11 is the same as the optical tomography imaging system 10 except for a processing section 23, a control operation section 33, and tomographic image creating means 87 of the processing section 23. Components common to the optical tomography imaging system 11 and the optical tomography imaging system 10 are denoted by the same reference symbols and their detailed descriptions are omitted here. The following description focuses on features specific to the optical tomography imaging system 11.

As shown in FIG. 12, the optical tomography imaging system 11 has-the light source unit 12, which emits a light beam, the branching/multiplexing section 14, which branches the light beam emitted from the light source unit 12 into a measuring light beam and a reference light beam and which combines a reflected light beam with the reference light beam to create an interference light beam, the optical probe 16, which guides the measuring light beam to irradiate a measurement target with the measuring light beam and obtain light reflected by the measurement target, the light path length adjusting section 18, which adjusts the light path length of the reference light beam, the interference light beam detecting section 20, which detects the interference light beam created by the branching/multiplexing section 14 as an interference signal, the processing section 23, which processes the interference signal detected by the interference light beam detecting section 20, and the display section 24, which displays a tomographic image obtained by the processing section 23. The optical tomography imaging system 11 also has the rotation driving section 26, which rotates the measurement section and others of the optical probe, the optical fiber coupler 28, which disperses the light beam emitted from the light source unit 12, the detector section 30a, which detects the reference light beam, the detector section 30b, which detects the reflected light beam, and the control operation section 33, which inputs various conditions to the processing section 23, the display section 24, and other components, changes settings, and performs other similar operations. An optical fiber is used as a path for light and guides light including the measuring light beam, the reference light beam, and the reflected light beam to relevant components.

The processing section 23 detects, from an interference signal detected by the interference light beam detecting section 20, an area where the optical probe 16 and the measurement target S are in contact with each other at a measurement point, more strictly, an area that is deemed as where the surface of the probe sheath 52 of the optical probe 16 is in contact with the surface of the measurement target S. The processing section 23 also obtains a tomographic image from an interference signal detected by the interference light beam detecting section 20.

As shown in FIG. 13, the processing section 23 has the interference signal obtaining means 80, the A/D conversion means 82, the contact area detecting means 84, the tomographic image creating means 87, and the image correcting means 88.

The interference signal obtaining means 80, the A/D conversion means 82, the contact area detecting means 84, the image correcting means 88, and a method of detecting the position of the circumferential wall of the probe and a method of detecting a contact area in which the probe sheath 52 and the measurement target S are in contact with each other performed by the contact area detecting means 84 are the same as in the optical tomography imaging system 10, and their detailed descriptions are therefore omitted here.

The interference signal obtaining means 80 obtains an interference signal detected by the interference light beam detecting section 20 and also obtains information on a measurement point detected by the rotation driving section 26, specifically, positional information of a measurement point detected from information on the position of the optical lens 62 in the rotation direction, to associate the interference signal and the positional information of the measurement point with each other. The interference signal associated with the positional information of a measurement point is sent to the A/D conversion means 82.

The A/D conversion means 82 converts the interference signal associated with the positional information of a measurement point and output as an analog signal by the interference signal obtaining means 80 into a digital signal.

The interference signal associated with the positional information of a measurement point and converted into a digital signal is sent to the contact area detecting means 84 and the tomographic image creating means 87.

The contact area detecting means 84 detects the position of the circumferential wall of the probe at a point where the measuring light beam L1 passes through the wall of the probe sheath 52, and an area of contact between the probe sheath 52 and the measurement target S at the point where the measuring light beam L1 passes through the wall of the probe sheath 52.

The detected area of contact between the probe sheath 52 and the measurement target S is sent to the tomographic image creating means 87.

The tomographic image creating means 87 performs fast Fourier transform (FFT) on the interference signals converted by the A/D conversion means 82 into digital signals to obtain information on a relation between the frequency component and the intensity. The tomographic image creating means 87 processes the frequency component-intensity relation information, thereby obtaining a tomographic image in the depth direction.

The tomographic image creating means 87 sets different processing conditions to a contact area and an area that is not the contact area based on the contact area information sent from the contact area detecting means 84 and processing conditions sent from the control operation section 33, which is described later. In obtaining a tomographic image, the tomographic image creating means 87 uses a first processing condition to process interference signals that are associated with positional information of an area judged as a contact area, while processing interference signals that are associated with positional information of other areas than a contact area under a second processing condition.

The first processing condition is a condition that yields a higher processing accuracy than the second processing condition does. Examples of the processing conditions include the processing amount for one interference signal and the count of interference signals processed per unit area.

More specifically, in the case where the difference in processing accuracy is measured by the processing amount fox one interference signal, the first processing condition is a condition that yields more processing amount for one interference signal than the second processing condition does and, in the case where the difference in processing accuracy is measured by the count of interference signals processed per unit area, the first processing condition is a condition that causes more interference signals to be processed per unit area than the second processing condition does.

The tomographic image creating means 87 creates an image in the same way as the tomographic image creating means 86 of the optical tomography imaging system 10, and its description is therefore omitted here.

The image correcting means 88 performs logarithmic transformation and radial transformation on tomographic images created by the tomographic image creating means 87, and arranges the images in order by line number to obtain a circular image with the center of rotation of the optical lens as the center of the circle.

The image correcting means 88 also performs sharpening processing, smoothing processing; and the like on a tomographic image to correct the image quality.

The image correcting means 88 sends the tomographic image that has been subjected to the image quality correction to the display section 24.

The control operation section 33 has input means such as a keyboard and/or a mouse and control means which manages various conditions based on input information. The control operation section 33 is connected to the processing section 23 and the display section 24. The control operation section 33 responds to an instruction input by an operator through the input means by, for example, inputting the above-mentioned threshold and various processing conditions to the processing section 23, or setting or changing the threshold and the conditions, or changing the display settings of the display section 24. An operation window of the control operation section 33 may be displayed by the display section 24 or by a different display section. Further, the control operation section 33 may control the operation of and set various conditions of the light source unit 12, the light path length adjusting section 18, the interference light beam detecting section 20, the rotation driving section 26, and the detector sections 30a and 30b.

The optical tomography imaging system 11 basically has the above-mentioned structure.

Given next is a description on the operation of the optical tomography imaging system 11, which describes in more detail the optical tomographic image obtaining method according to the fourth aspect of the present invention and the optical tomography imaging system according to the fifth aspect of the present invention.

In the optical tomography imaging system 11, an interference light beam and interference signals are obtained in measurement of the measurement target S in the same way as the interference light beam and interference signal obtaining method in the optical tomography imaging system 10. A detailed description thereof is therefore omitted.

The following description is about how an interference light beam detected in the manner described above is processed.

Figure 14:
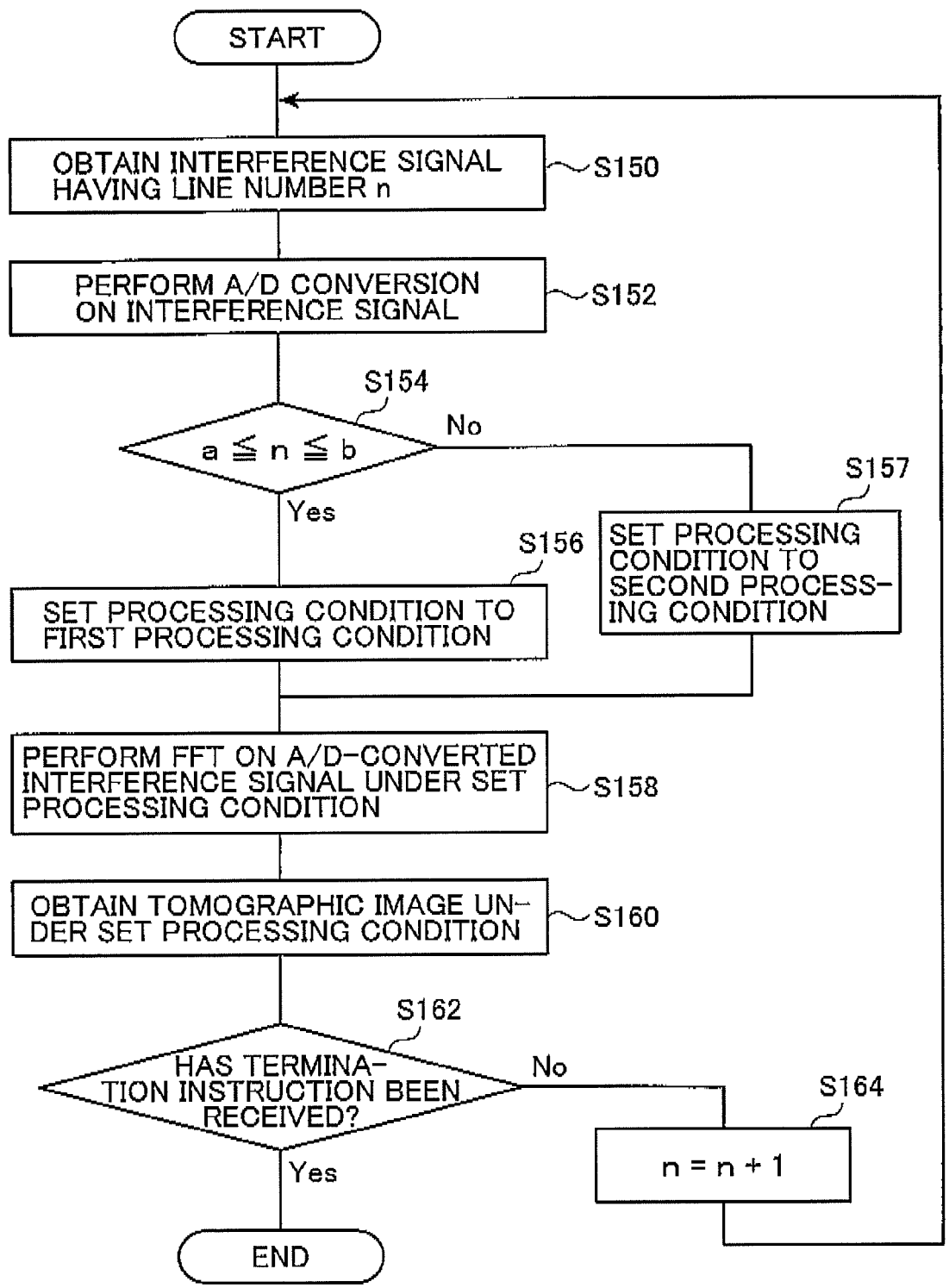
FIG. 14 is a flow chart showing an example of a method of obtaining a tomographic image based on a detected contact area.

FIG. 14 is a flow chart showing the method of obtaining a tomographic image based on a detected contact area.

A method of detecting the position of the circumferential wall of the probe is described A detailed description on the method of detecting the position of the circumferential wall of the probe is omitted here because, in the optical tomography imaging system 11, the position of the circumferential wall of the probe is detected by the same method as the one employed in the optical tomography imaging system 10 and described in detail with reference to FIG. 7.

First, arbitrarily chosen one line of interference signals are obtained (Step S10).

Next, the detected interference signals are converted by A/D conversion (Step S12).

FFT is performed next on the interference signals converted by A/D conversion, to thereby obtain information on a relation between the frequency component and the intensity. The frequency component-intensity relation information is further processed to obtain a relation between the depth direction and the intensity, which is used to detect peak points (Step S14).

From a detected peak point, the position of the circumferential wall of the probe is detected (Step S16).

The position of the circumferential wall of the probe is thus detected.

A method of detecting a contact area in which the probe sheath 52 and the measurement target S are in contact with each other is described next.

A detailed description on the method of detecting a contact area in which the probe sheath 52 and the measurement target S are in contact with each other is omitted here because, in the optical tomography imaging system 11, a contact area in which the probe sheath 52 and the measurement target S are in contact with each other is detected by the same method as the one employed in the optical tomography imaging system 10 and described in detail with reference to FIG. 8.

First, the line number n is set to 1 (Step S20).

Next, interference signals having the line number n are obtained (Step S22).

When the line number of obtained interference signals is not n, the processing of obtaining interference signals is repeated until the interference signals having the line number n are obtained.

Next, A/D conversion is performed on the detected interference signals (Step S24).

FFT is next performed on the interference signals converted by A/D conversion to detect peak points (Step S26).

The position of the surface of the measurement target S is detected from a detected peak point (Step S28).

Next, the distance between the detected surface of the measurement target S and the circumferential wall of the probe is detected, and whether or not the detected distance is equal to or smaller than the threshold X is judged (Step S30).

When the detected distance is equal to or smaller than the threshold X, it is judged that the measurement target S and the circumferential wall of the probe are in contact with each other (Step S32), and the processing proceeds to Step S36. When the detected distance is larger than the threshold X, it is judged that the measurement target S and the circumferential wall of the probe are not in contact with each other (Step S34), and the processing proceeds to Step S36.

Whether or not the line number n is N is judged next (Step S36).

When the line number n is not N, n is set to n+1 (Step S38) and the processing moves to Step S22. By executing Step S22 after increasing n by 1, whether or not the circumferential wall of the probe and the measurement target are in contact with each other is judged for an adjacent line having one larger line number.

When the line number n is N, it means that the contact judging has been finished for every line, and a contact range table is created (Step S40).

After the contact range table is created in this manner, the processing is ended.

A contact area in which the circumferential wall of the probe and the measurement target are in contact with each other is thus detected.

The control operation section 33 associates the created contact range table with a processing condition input or set. Specifically, a contact area is associated with the first processing condition and an area that is not a contact area is associated with the second processing condition.

A method for obtaining a tomographic image is described next with reference to FIG. 14.

First, interference signals having the line number n which is an arbitrary line number are obtained (Step S150). Specifically, the interference light beam detecting section 20 detects, as an interference signal, the interference light beam L4 which is created by combining the reference light beam L2 and the reflected light beam L3 in the manner described above.

Next, A/D conversion is performed on the detected interference signals (Step S152). Specifically, the A/D conversion means 82 converts the interference signals which are analog signals into digital signals.

Whether or not the line number n is included in the contact range table created in Step S40, specifically, whether or not the line number n is between the line number a and the line number b which define the contact area, is judged next (Step S154). In short, whether a≦n≦b is satisfied or not is judged.

When the line number n satisfies a≦n≦b, the processing condition is set to the first processing condition (Step S156), and the processing then moves to Step S158.

When the line number n does not satisfy a≦n≦b, in other words, when n is smaller than a or larger than b (n≦a or b≦n), the processing condition is set to the second processing condition (Step S157), and the processing then moves to Step S158.

Under the set processing condition, FFT is performed on the interference signals converted by A/D conversion (Step S158). The first processing condition is set in the case where the line number associated with the interference signals corresponds to a portion of the contact area, and the second processing condition is set in the case where the line number associated with the interference signals does not correspond to a portion of the contact area.

Next, results of the FFT calculation are processed under the set processing condition to obtain a tomographic image for the line number n (Step S160).

The tomographic image is obtained from results of FFT by performing given processing as described above.

In this embodiment, the count of processing items in one interference signal differs between the first processing condition and the second processing condition. Specifically, the first and second processing conditions are set such that the data bit count of an interference signal and the count of data items used to process one interference signal are larger in the first processing condition than in the second processing condition.

After a tomographic image is obtained by processing interference signals of a contact area under the first processing condition and interference signals of an area that is not a contact area under the second processing condition in this manner, the processing proceeds to Step S162.

Whether or not a termination instruction has been received is then judged (Step S162).

In the case where a termination instruction has not been received, n is set to n+1 and the processing moves to Step S150. By executing Step S150 after increasing n by 1, the tomographic image obtaining processing is performed for an adjacent line having one larger line number. Though omitted from the drawing, when Step S164 makes n into N+1, n is set to 1 and the processing of obtaining a tomographic image is continued until a termination instruction is received.

When a termination instruction is received, the processing is ended.

A tomographic image of a measurement target is obtained in the manner described above.

The thus obtained tomographic image is sent to the image correcting means to receive image processing for preparation for display, such as radial transformation and sharpening. The processed image is sent to the display section 24, which then displays the image.

According to the fourth and fifth aspects of the present invention, by detecting a contact area in which a measurement target and the optical probe are in contact with each other with the contact area detecting means, an area where a high-resolution tomographic image will be detected can be detected and recognized. Processing only an area where a reliable, high-resolution image will be obtained is thus made possible as in this embodiment.

The present invention also lessens the load on the processing section and shortens the processing time by processing information that is associated with a contact area under the first processing condition, which sets the precision high, and processing information that is associated with other areas than a contact area under the second processing condition, which sets the precision lower than the first processing condition does. In this way, video images can be displayed at high speed even with an inexpensive processor. A high-resolution tomographic image can thus be displayed while keeping the cost of the system low.

Information on a detected contact area is used to obtain a fine image as a tomographic image of the contact area where a high-resolution, actually needed image will be obtained, while a coarse image is produced by image processing for an area of the measurement target that is apart from the optical probe and will provide a low-resolution, unclear image which is not very useful as a tomographic image. A tomographic image of the present invention can therefore be used effectively.

Specifically, in an area that is not a contact area, the detected signals have low resolution in the first place and performing sophisticated image processing on the low-resolution signals does not yield a high-resolution image. Add to the fact that performing normal image processing on signals of an area that is not a contact area produces an image not very useful for diagnosis, testing, or the like, obtaining a coarse image for an area that is not a contact area essentially has no adverse effects on the accuracy of diagnosis, testing, or the like. Therefore, by obtaining a fine image for a contact area, a tomographic image of the present invention can be used effectively.

Varying the image processing condition depending on the type of the measured area also makes more sophisticated image processing of a tomographic image possible without increasing the overall information processing amount.

Further, the overall structure of the surroundings of the measurement section can be grasped by obtaining tomographic images in 360° directions, although images of other areas than a contact area are coarse. The knowledge of the overall structure makes the insertion and other operation of the optical probe easier.

In this embodiment, the count of processing items in one interference signal differs between the first processing condition and the second processing condition. Alternatively, the count of interference signals processed per unit area may differ between the first processing condition and the second processing condition. In other words, in obtaining a tomographic image of an area that is not a contact area, interference signals to be processed may be thinned out.

Figure 15:
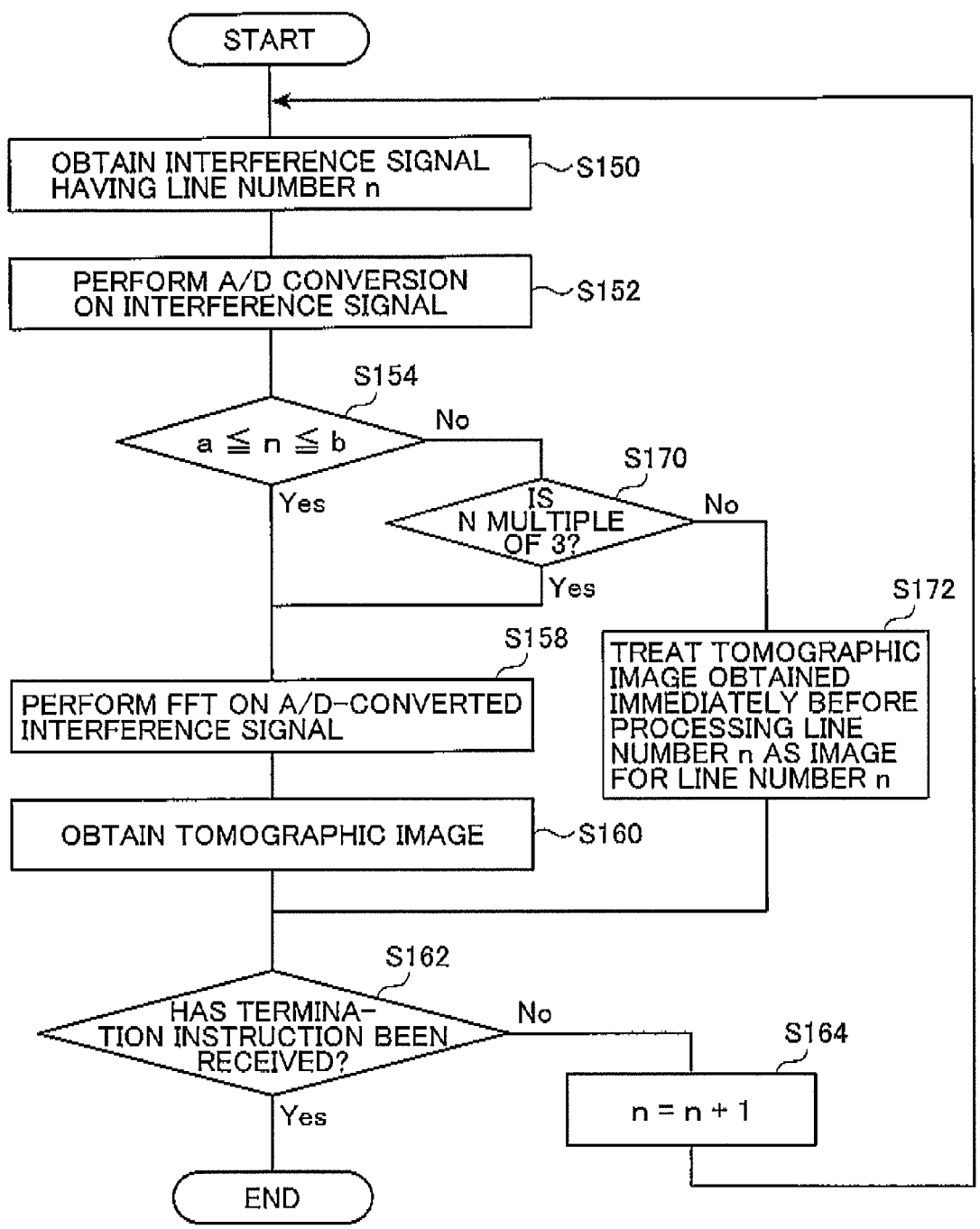
FIG. 15 is a flow chart showing another example of the method of obtaining a tomographic image based on a detected contact area.

FIG. 15 is a flow chart showing another example of the method of calculating a tomographic image based on a detected contact area.

Referring to FIG. 15, a description is given on another example of the method for obtaining a tomographic image, specifically, a case where the count of interference signals processed per unit area differs between the first processing condition and the second processing condition. In this embodiment, the first processing condition is set such that all interference signals are processed and the second processing condition is set such that one interference signal out of three interference signals is processed. The processing of one interference signal itself is the same in the first processing condition and the second processing condition.

Steps identical to those in the tomographic image obtaining method of FIG. 14 described above are denoted by the same reference numbers, and their detailed descriptions are omitted here.

First, interference signals having the line number n which is an arbitrary line number are obtained (Step S50).

Next, A/D conversion is performed on the detected interference signals (Step S152).

Whether or not the line number n is included in the contact range table created in Step S40 is judged next (Step S154).

When the line number n satisfies $a \leq n \leq b$, the first processing condition fits and the processing proceeds directly to Step S158.

When the line number n does not satisfy $a \leq n \leq b$, the second processing condition fits and the processing proceeds to Step S170.

In Step S170, whether or not the line number n is a multiple of 3 is judged.

When the line number n is a multiple of 3, the processing moves to Step S158. When the line number n is not a multiple of 3, a tomographic image that has been obtained immediately before processing this line number n is treated as an image for the line number n (Step S172). In other words, an already calculated tomographic image of the adjacent line is used as a tomographic image for the line number n instead of processing interference signals.

Next, FFT is performed on the interference signals converted by A/D conversion (Step S158). Results of the FFT calculation are processed to obtain a tomographic image for the line number n (Step S160).

In this embodiment, the same processing is performed on interference signals of Step S154 and interference signals of Step S170.

After a tomographic image is obtained in this manner, the processing proceeds to Step S162.

Whether or not a termination instruction has been received is then judged (Step S162).

In the case where a termination instruction has not been received, n is set to n+1 and the processing moves to Step S150. When a termination instruction is received, the processing is ended.

Thus, the information processing amount can be reduced also by processing all interference signals in a contact area whereas processing only ⅓ of all interference signals in an area that is not a contact area. Further, the same effects as in the above example are obtained since interference signals of a contact area are processed with high precision and the overall structure can be grasped.

While one interference signal out of three interference signals is processed in this embodiment, the interference signal thinning ratio (how frequently the processing is executed) is not particularly limited. For example, one out of two interference signals or one out of four interference signals may be processed. It may also be set such that a given count of interference signals picked out at random from lines within a unit area are processed.

The above-mentioned two processing conditions may be added to the processing condition of this embodiment, so that, under the second processing condition, the count of interference signals processed per unit area and the processing amount for one interference signal are smaller than when the first processing condition is employed. In other words, the first processing condition may be set such that the count of interference signals processed per unit area and the processing amount for one interference signal are larger than those of the second processing condition.

This reduces the amount of information to be processed even more, and the above-mentioned effects are obtained in a more favorable manner.

The optical tomography imaging system 11 employs swept source-OCT (SS-OCT) to obtain a tomographic image of a measurement target and detect an area of contact with the measurement target, but the present invention is not limited thereto.

Figure 16:
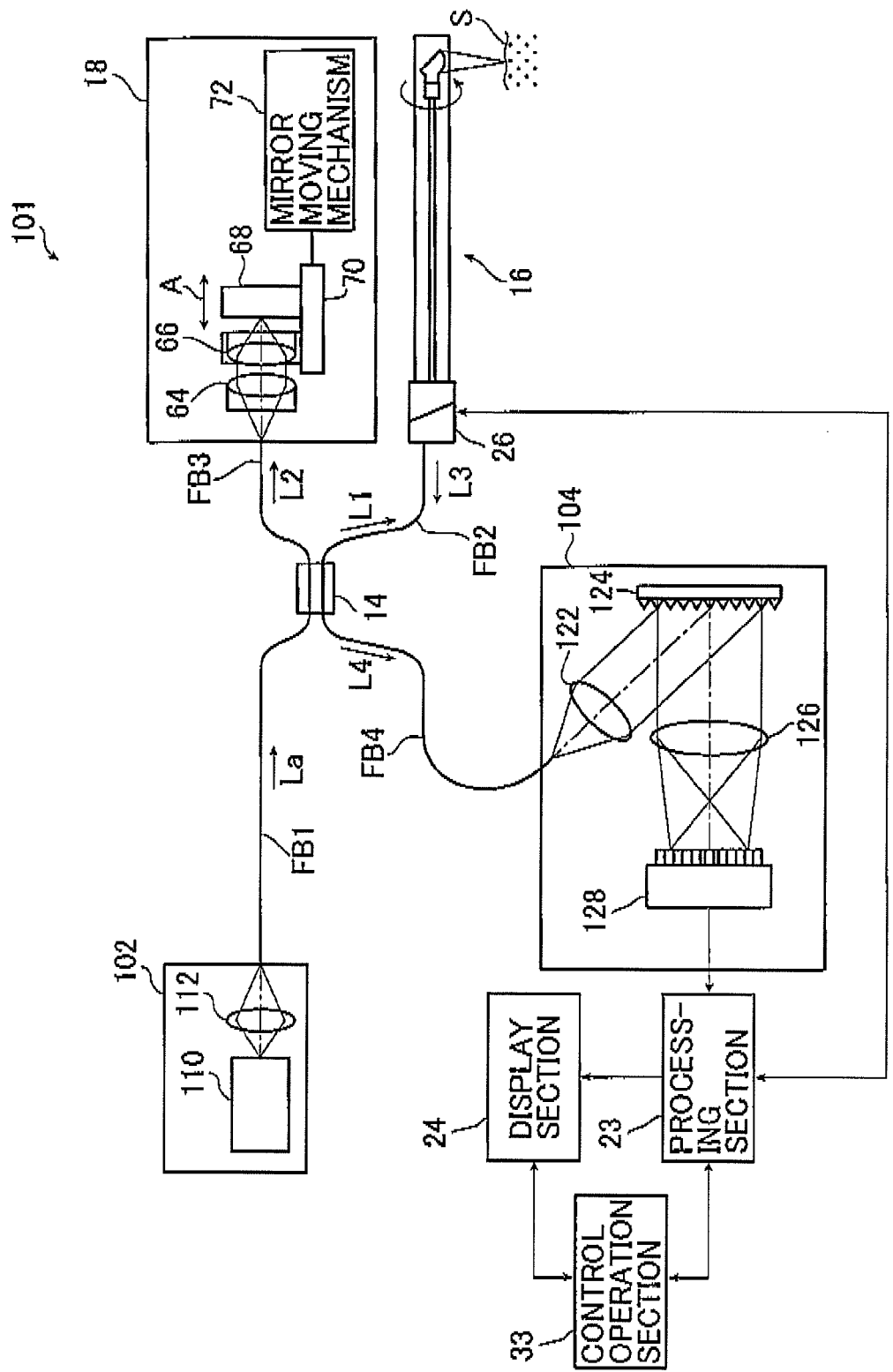
FIG. 16 is a block diagram showing a schematic structure of another embodiment of the optical tomography imaging system according to the fifth aspect of the present invention.

FIG. 16 is a block diagram schematically showing a schematic structure of another embodiment of the optical tomography imaging system.

The optical tomography imaging system shown in FIG. 16 is denoted by 101, and is the same as the optical tomography imaging system 11 except that spectral domain-OCT (SD-OCT) is employed to obtain a tomographic image of a measurement target and detect an area of contact with the measurement target. Components common to the optical tomography imaging system 101 and the optical tomography imaging system 11 are denoted by the same reference symbols and their detailed descriptions are omitted here. Further, the optical tomography imaging system 101 is the same as the optical tomography imaging system 100 except for the processing section 23 and the control operation section 33. Components common to the optical tomography imaging system 101 and the optical tomography imaging system 100 are denoted by the same reference symbols and their detailed descriptions are omitted here. The following description is about the optical tomography imaging system 101.

The optical tomography imaging system 101 has the light source unit 102, which emits a light beam, the branching/multiplexing section 14, which branches the light beam emitted from the light source unit 102 into a measuring light beam and a reference light beam and combines a reflected light beam with the reference light beam to create an interference light beam, the optical probe 16, which guides the measuring light beam to irradiate a measurement target with the measuring light beam and collects light reflected by the measurement target, the light path length adjusting section 18, which adjusts the light path length of the reference light beam, the interference light beam detecting section 104, which detects the interference light beam created by the branching/multiplexing section 14, the processing section 23, which processes results of detection by the interference light beam detecting section 104, and the display section 24, which displays a tomographic image obtained by the processing section 23. The optical tomography imaging system 101 also has the rotation driving section 26, which rotates the measurement section and others of the optical probe, and the control operation section 33, which inputs various conditions to the processing section 23, the display section 24, and other components, changes settings, and performs other similar operations. An optical fiber is used as a path for light and guides light including the measuring light beam, the reference light beam, and the reflected light beam to relevant components.

The light source unit 102 has the light source 110 and the optical system 112 to make the laser light beam La incident on the optical fiber FB1.

The interference light beam detecting section 104 has the collimator lens 122, the dispersing means 124, the lens 126, and the light detecting means 128. The interference light beam detecting section 104 detects, as an interference signal, the interference light beam L4 which is created in the branching/multiplexing section 14 by combining the reflected light beam L3 and the reference light beam L2. The dispersing means 124 disperses the incident interference light beam L4, which then exits toward the light detecting means 128. The light detecting means 128 detects, as interference signals, beams of the dispersed interference light beam L4 on a wavelength range basis.

The interference light beam detecting section 104 sends the detected interference signals to the processing section 23.

The contact area detecting means 84 of the processing section 23 detects a contact area in which the circumferential wall of the probe and the measurement target are in contact with each other-from detected peak points in the depth direction and intensity distribution, and the tomographic image creating means 86 obtains a tomographic image.

In this way, although the optical tomography imaging system 101 employs a different method to obtain interference signals from the optical tomography imaging system 11, the same effects as in the optical tomography imaging system 11 can be obtained in the optical tomography imaging system 101 by detecting a contact area in which the circumferential wall of the probe and a measurement target are in contact with each other with the contact area detecting means, and by processing the contact area and other areas than the contact area under different processing conditions so that a tomographic image of the contact area is obtained with higher precision.

Figure 17:
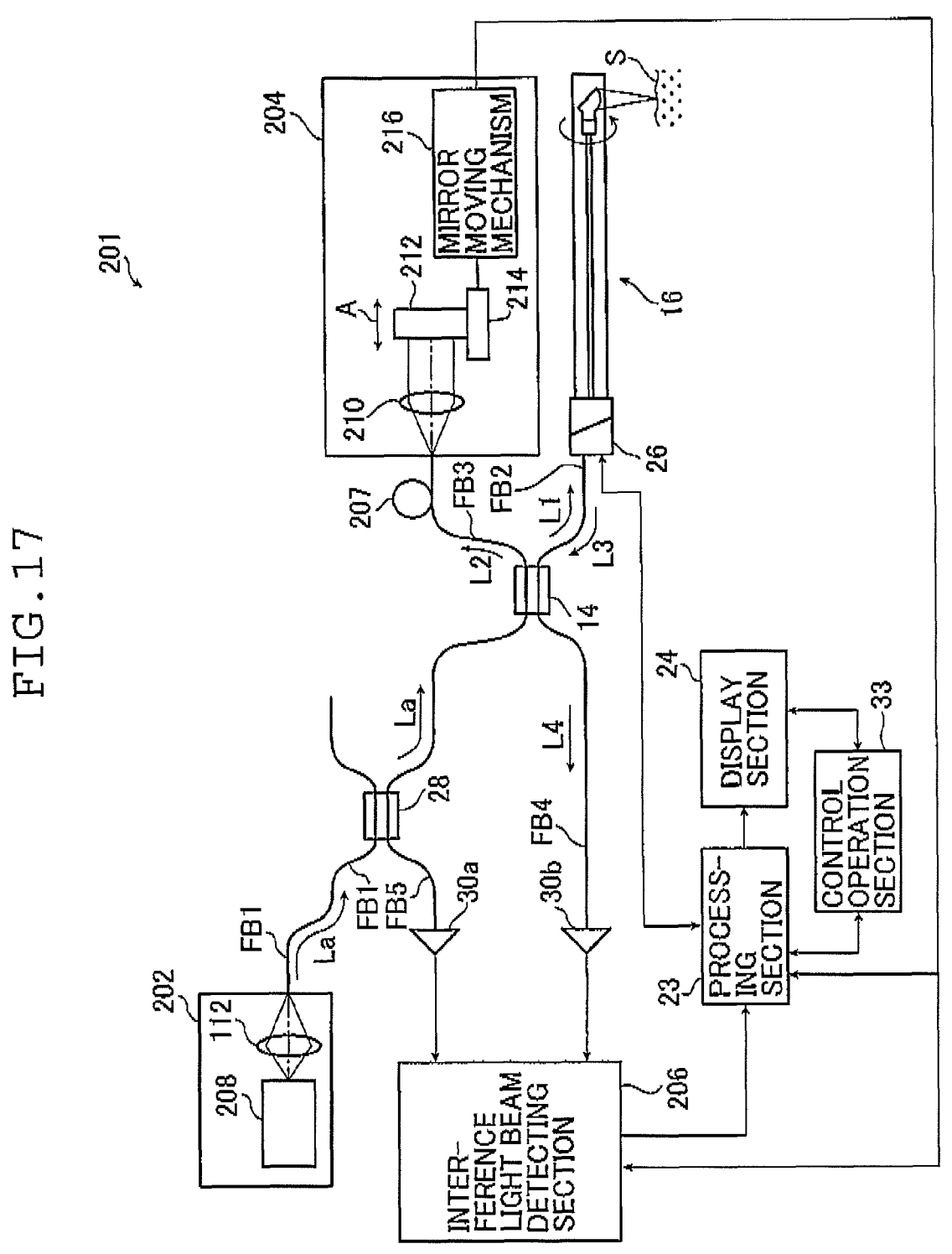

FIG. 17 is a block diagram schematically showing a schematic structure of still another embodiment of the optical tomography imaging system.

The optical tomography imaging system shown in FIG. 17 is denoted by 201, and is the same as the optical tomography imaging system 11 except that time domain-OCT (TD-OCT) is employed to obtain a tomographic image of a measurement target and detect an area of contact with the measurement target. Components common to the optical tomography imaging system 201 and the optical tomography imaging system 11 are denoted by the same reference symbols and their detailed descriptions are omitted here. Further, the optical tomography imaging system 201 is the same as the optical tomography imaging system 200 except for the processing section 23 and the control operation section 33. Components common to the optical tomography imaging system 201 and the optical tomography imaging system 200 are denoted by the same reference symbols and their detailed descriptions are omitted here. The following description is about the optical tomography imaging system 201.

The optical tomography imaging system 201 has the light source unit 202, which emits a light beam, the branching/multiplexing section 14, which branches the light beam emitted from the light source unit 202 into a measuring light beam and a reference light beam and combines a reflected light beam with the reference light beam to create an interference light beam, the optical probe 16, which guides the measuring light beam to irradiate a measurement target with the measuring light beam and collects light reflected by the measurement target, the light path length adjusting section 204, which adjusts the light path length of the reference light beam and changes the light path length periodically, the interference light beam detecting section 206, which detects the interference light beam created by the branching/multiplexing section 14, the processing section 23, which processes results of detection by the interference light beam detecting section 206, and the display section 24, which displays a tomographic image obtained by the processing section 23. The optical tomography imaging system 201 also has the rotation driving section 26, which rotates the measurement section and others of the optical probe, the optical fiber coupler 28, which disperses the light beam emitted from the light source unit 202, the detector section 30a, which detects the reference light beam, the detector section 30b, which detects the reflected light beam, and the control operation section 33, which inputs various conditions to the processing section 23, the display section 24, and other components, changes settings, and performs other similar operations. An optical fiber is used as a path for light and guides light including the measuring light beam, the reference light beam, and the reflected light beam to relevant components.

The light source unit 202 has the light source 208 and the optical system 112 to make the laser light beam La incident on the optical fiber FB1. The optical system 112 collects the laser light beam La emitted from the light source 208 to make the light incident on the optical fiber FB1.

The light path length adjusting section 204 has the collimator lens 210, the mirror 212, the base 214, and the mirror moving mechanism 216. By moving the mirror 212 and varying the light path length of the reference light beam L2, the light path length adjusting section 204 changes the measurement point in the measurement target S in the depth direction.

The phase modulator 207 gives a slight frequency shift to the reference light beam L2.

After receiving the light path length change and frequency shift in the light path length adjusting section 204, the reference light beam L2 is guided to the branching/multiplexing section 14.

The branching/multiplexing section 14 combines the reference light beam L2 with the reflected light beam L3 to create the interference light beam L4 as described above.

The interference light beam detecting section 206 employs, for example, heterodyne detection to detect the light intensity of the interference light beam L4 propagated through the optical fiber FB4 from the branching/multiplexing section 14.

The interference light beam detecting section 206 therefore detects beat signals, namely, interference signals, for each measurement point. The light path length adjusting section 204 has a calculating section which calculates the measurement point from the mirror position, and outputs the calculated measurement point to the interference light beam detecting section 206 and the processing section 23.

The contact area detecting means 84 and the tomographic image creating means 87 of the processing section 23 calculate a relation between the measurement point (i.e., depth direction) and the intensity. From the calculated depth direction-intensity relation, peak points in the depth direction and the intensity distribution can be obtained as in the optical tomography imaging system 11.

The contact area detecting means 84 detects a contact area in which the circumferential wall of the probe and the measurement target are in contact with each other from the detected peak points in the depth direction and intensity distribution, and the tomographic image creating means 87 obtains a tomographic image.

In this way, although the optical tomography imaging system 201 employs a different method to obtain interference signals from the optical tomography imaging system 11, the same effects as in the optical tomography imaging system 11 can be obtained in the optical tomography imaging system 201 by detecting a contact area in which the circumferential wall of the probe and a measurement target are in contact with each other with the contact area detecting means, and by processing the contact area and other areas than the contact area under different processing conditions so that a tomographic image of the contact area is obtained with higher precision.

An optical tomographic image obtaining method and optical tomography imaging system according to the present invention is described in detail through embodiments illustrated in the accompanying drawings.

Figure 18:
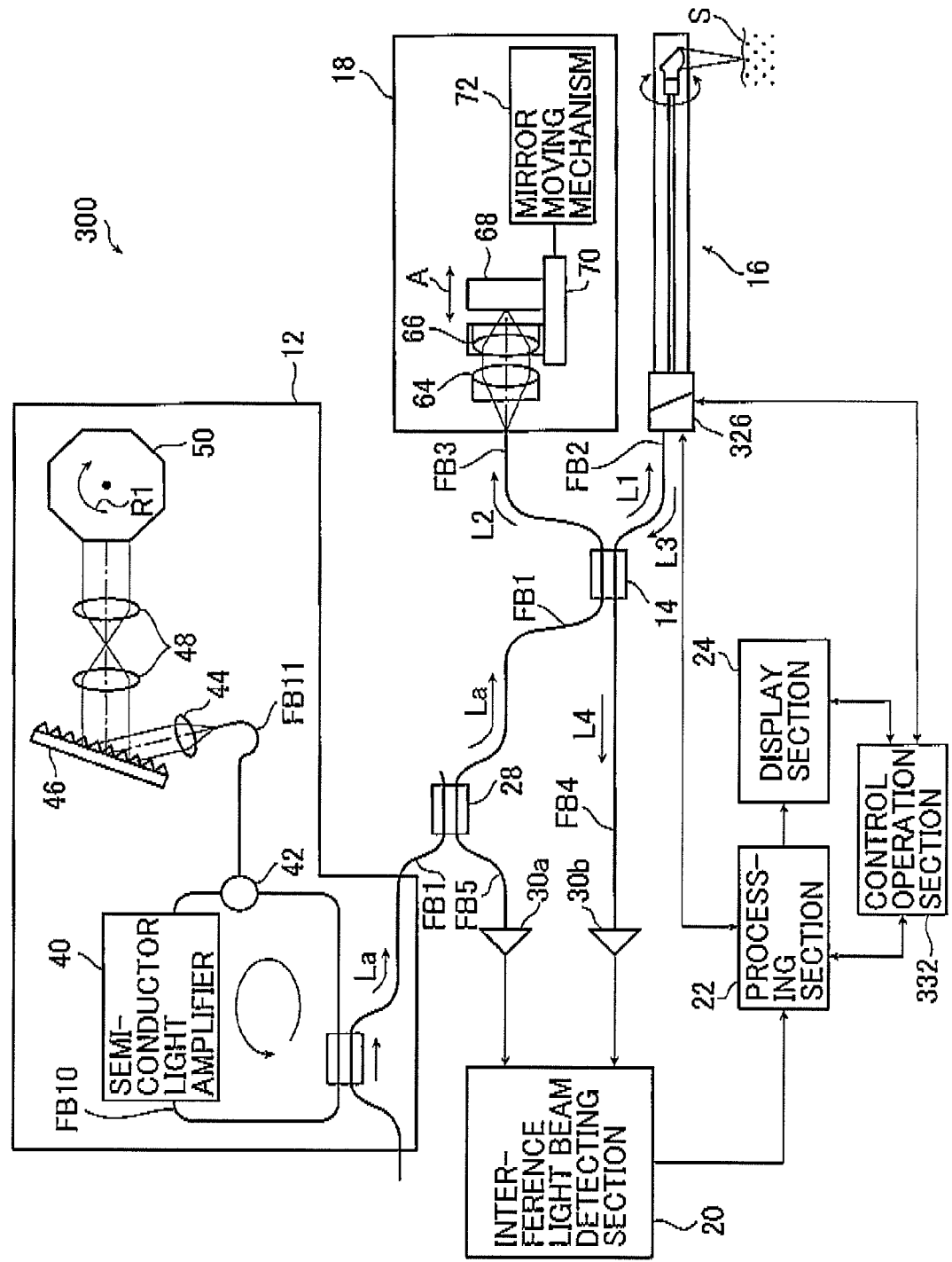
FIG. 18 is a block diagram showing a schematic structure of an embodiment of an optical tomography imaging system according to the seventh aspect of the present invention which employs an optical tomographic image obtaining method according to the sixth embodiment of the present invention.
Figure 19:
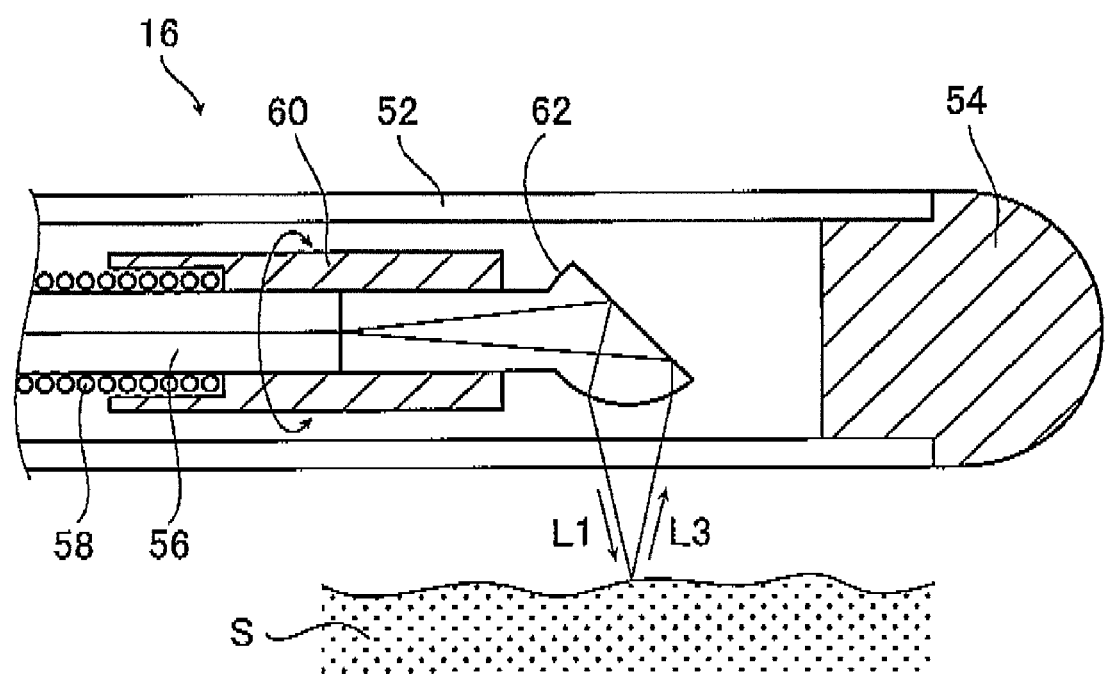
FIG. 19 is a partial sectional view showing an enlarged tip of an optical probe of the optical tomography imaging system shown in FIG. 18.

FIG. 18 is a block diagram showing a schematic structure of an embodiment of an optical tomography imaging system 300 according to the present invention which employs an optical tomographic image obtaining method according to the present invention, FIG. 19 is a partial sectional view showing an enlarged tip of the optical probe 16 of the optical tomography imaging system 300 shown in FIG. 18. FIG. 3 is a block diagram showing the schematic structure of the processing section 22 of the optical tomography imaging system 300 shown in FIG. 18.

The optical tomography imaging system 300 has basically the same structure as that of the optical tomography imaging system 10 shown in FIG. 1 except for a rotation driving section 326 and a control operation section 332. Components common to the optical tomography imaging system 300 and the optical tomography imaging system 10 are denoted by the same reference symbols and their detailed descriptions are omitted here. The following description focuses on features specific to the optical tomography imaging system 300.

As shown in FIG. 18, the optical tomography imaging system 300 has the light source unit 12, which emits a light beam, the branching/multiplexing section 14, which branches the light beam emitted from the light source unit 12 into a measuring light beam and a reference light beam and combines a reflected light beam with the reference light beam to create an interference light beam, the optical probe 16, which guides the measuring light beam to irradiate a measurement target with the measuring light beam and obtains light reflected by the measurement target, the light path length adjusting section 18, which adjusts the light path length of the reference light beam, the interference light beam detecting section 20, which detects the interference light beam created by the branching/multiplexing section 14 as an interference signal, the processing section 22, which processes the interference signal detected by the interference light beam detecting section 20, and the display section 24, which displays a tomographic image obtained by the processing section 22. The optical tomography imaging system 300 also has the rotation driving section 326, which rotates a measurement section and others of the optical probe, the optical fiber coupler 28, which disperses the light beam emitted from the light source unit 12, the detector section 30a, which detects the reference light beam, the detector section 30b, which detects the reflected light beam, and the control operation section 332, which inputs various conditions to the processing section 22, the display section 24, and other components, changes settings, calculates and controls the rotation count and rotation angle of the rotation driving section 326, and performs other similar operations. An optical fiber is used as a path for light and guides light including the measuring light beam, the reference light beam, and the reflected light beam to relevant components.

The optical probe 16 is connected to the optical fiber FB2 through the rotation driving section 326. The optical probe 16 irradiates the measurement target S with the incident measuring light beam L1 which enters through the optical fiber FB2, picks up the reflected light beam L3 reflected by the measurement target S, and lets the picked up a reflected light beam L3 exit to the optical fiber FB2.

The optical probe 16 has the probe sheath 52, the cap 54, the optical fiber 56, the spring 58, the fixing member 60, and the optical lens 62 as shown in FIG. 19.

The rotation driving section 326 is connected to the optical fiber 56 and the spring 58, and rotates the optical fiber 56 and the spring 58 to thereby rotate the optical lens 62 with respect to the probe sheath 52. The rotation driving section 326 is a driving mechanism that can vary the rotation speed and the rotation direction, and rotates the optical fiber 56 and the spring 58 in a given direction at a given speed in accordance with an instruction from the control operation section 332, which is described later.

The rotation driving section 326 also has a rotary encoder (not shown), and detects the irradiation point of the measuring light beam L1 from positional information (angle information) of the optical lens 62 based on a signal from the rotary encoder. In other words, the rotation driving section 326 detects a measurement point by detecting an angle in the rotation direction of the rotating optical lens 62 with respect to a reference point.

The thus structured optical probe 16 irradiates the measurement target S with the measuring light beam L1 which exits the optical lens 62 as the rotation driving section 326 rotates the optical fiber 56 and the spring 58 in a given direction, by running the measuring light beam L1 in a given direction (the circumferential direction of the probe sheath 52), and picks up the resultant reflected light beam L3.

In this way, the reflected light beam L3 reflected by the measurement target S can be picked up at any point in the circumferential direction of the probe sheath 52.

FIG. 4, which is an explanatory diagram illustrating positional information of an optical probe measurement point in the optical tomography imaging system 10, applies to this embodiment, too, and the measurement count per rotation of the optical lens 62 is determined from the rotation speed of the optical lens 62 and the sweeping cycle in which the frequency of the measuring light beam L1 is swept. In this embodiment, the number of times interference signals are obtained per rotation of the optical lens 62 is 1024 at the time of detecting a contact area described later. In contact area detection, the optical lens 62 rotates at a constant speed and interference signals are obtained at regular intervals (the frequency of the measuring light beam L1 is swept in a fixed cycle).

The control operation section 332 has input means such as a keyboard and/or a mouse and control means which manages various conditions based on input information. The control operation section 332 is connected to the processing section 22, the display section 24, and the rotation driving section 326. The control operation section 332 responds to an instruction input by an operator through the input means by, for example, inputting the above-mentioned threshold and various processing conditions to the processing section 22, or setting or changing the threshold and the conditions, or changing the display settings of the display section 24. Upon instruction from the operator, the control operation section 332 also calculates and sets the rotation speed and, if necessary, rotation direction, of the optical lens 62 of the optical probe 16 which is rotated by the rotation driving section 326. An operation window of the control operation section 332 may be displayed by the display section 24 or by a different display section. Further, the control operation section 332 may control the operation of and set various conditions of the light source unit 12, the light path length adjusting section 18, the interference light beam detecting section 20, and the detector sections 30a and 30b.

The optical tomography imaging system 300 basically has the above-mentioned structure.

Given next is a description on the operation of the optical tomography imaging system 300, which will describe in more detail the optical tomographic image obtaining method and optical tomography imaging system according to the present invention.

In the optical tomography imaging system 300, an interference light beam and interference signals are obtained in measurement of the measurement target S in the same way as the interference light beam and interference signal obtaining method in the optical tomography imaging system 10 of FIG. 1. A detailed description thereof is therefore omitted.

The following description is about how an interference light beam detected in the manner described above is processed.

Figure 20:
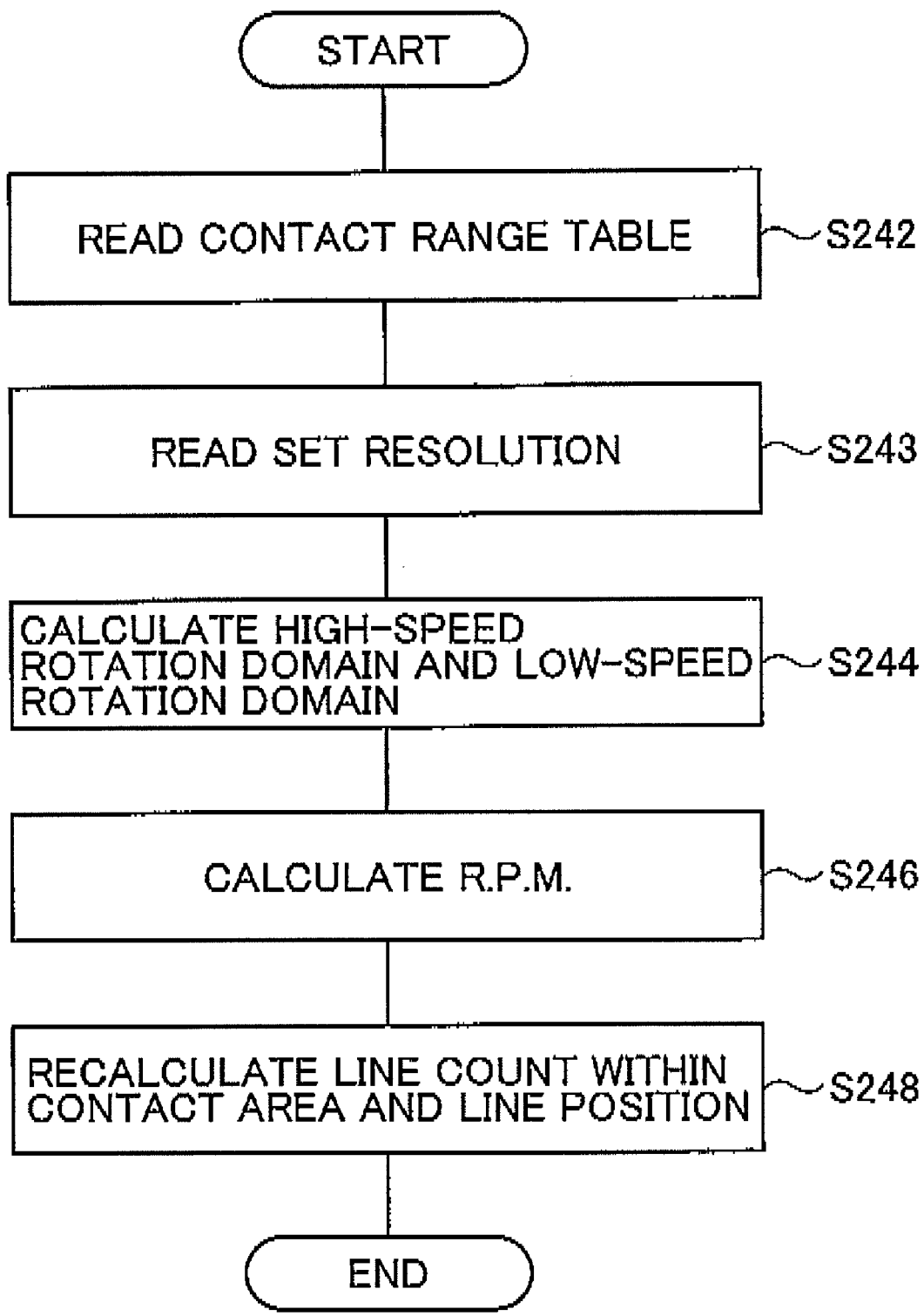
FIG. 20 is a flow chart showing an example of a method of calculating the rotation speed and a rotation direction of an optical lens and a relation between an interference signal and a measurement point.

FIG. 20 is a flow chart showing a method of obtaining a tomographic image based on a detected contact area.

A method of detecting the position of the circumferential wall of the probe is described.

A detailed description on the method of detecting the position of the circumferential wall of the probe is omitted here since, in the optical tomography imaging system 300, the position of the circumferential wall of the probe is detected by the same method as the one employed in the optical tomography imaging system 10 and described in detail with reference to FIG. 7.

First, arbitrarily chosen one line of interference signals are obtained (Step S10).

Next, the detected interference signals are converted by A/D conversion (Step S12).

FFT is performed next on the interference signals converted by A/D conversion, thereby obtaining information on a relation between the frequency component and the intensity. The frequency component-intensity relation information is further processed to obtain a relation between the depth direction and the intensity, which is used to detect peak points (Step S14).

From a detected peak point, the position of the circumferential wall of the probe is detected (Step S16).

The position of the circumferential wall of the probe is thus detected.

A method of detecting a contact area in which the probe sheath 52 and the measurement target S are in contact with each other is described next.

A detailed description on the method of detecting a contact area in which the probe sheath 52 and the measurement target S are in contact with each other is omitted here since, in the optical tomography imaging system 300, a contact area in which the probe sheath 52 and the measurement target S are in contact with each other is detected by the same method as the one employed in the optical tomography imaging system 10 and described in detail with reference to FIG. 8.

First, the line number n is set to 1 (Step S20).

Next, interference signals having the line number n are obtained (Step S22).

When the line number of obtained interference signals is not n, the processing of obtaining interference signals is repeated until interference signals having the line number n are detected.

Next, A/D conversion is performed on the detected interference signals (Step S24). Specifically, the A/D conversion means 82 converts the interference signals which are analog signals into digital signals.

FFT is next performed on the interference signals converted by A/D conversion to detect peak points (Step S26). As described above, a peak point is a point at which light is reflected and, basically, an interface between materials.

The position of the surface of the measurement target S is detected from a detected peak point (Step S28).

Since other objects are not interposed between the measurement target S and the optical probe 16 in principle, a peak point closest to a point where the probe sheath is detected in Step S16, in other words, a peak point second closest to the center of rotation (second shallowest point) is detected as the position of the surface of the measurement target S.

Next, the distance between the detected surface of the measurement target S and the circumferential wall of the probe is detected, and whether or not the detected distance is equal to or smaller than the threshold X is judged (Step S30).

When the detected distance is equal to or smaller than the threshold X, it is judged that the measurement target S and the circumferential wall of the probe are in contact with each other (Step S32), and the processing proceeds to Step S36. When the detected distance is larger than the threshold X, it is judged that the measurement target S and the circumferential wall of the probe are not in contact with each other (Step S34), and the processing proceeds to Step S36.

Whether or not the line number n is N is judged next (Step S36).

When the line number n is not N, n is set to n+1 (Step S38), and the processing moves to Step S22. By executing Step S22 after increasing n by 1, whether or not the circumferential wall of the probe and the measurement target are in contact with each other is judged for an adjacent line having one larger line number.

When the line number n is N, it means that the contact judging has been finished for every line, and a contact range table is created (Step S40).

After the contact range table is created, the processing is ended.

A contact area in which the circumferential wall of the probe and the measurement target are in contact with each other is thus detected.

The control operation section 332 calculates and sets the rotation speed and rotation direction of the optical lens 62 rotated by the rotation driving section 326, based on the created contact range table and input or set information such as the resolution of a tomographic image and the display speed. The control operation section 332 also calculates a relation between an interference signal and a measurement point during measurement based on the rotation speed and the rotation direction. A specific description is given below with reference to FIGS. 20 and 21.

Figure 21:
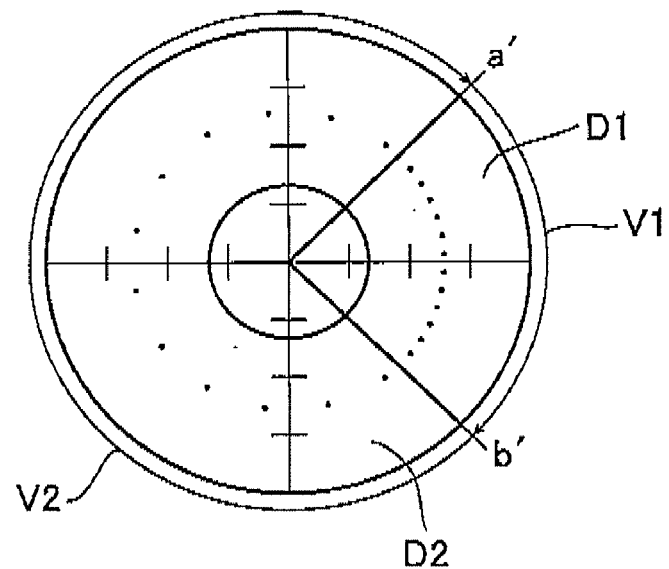
FIG. 21 is an explanatory diagram illustrating a relation between the rotation action of the optical lens which is calculated in FIG. 20 and a contact area.

FIG. 20 is a flow chart showing an example of a method of calculating the rotation speed and rotation direction of the optical lens 62 and a relation between an interference signal and a measurement point, FIG. 21 is an explanatory diagram illustrating a relation between the rotation action of the optical lens 62 which is calculated in FIG. 20 and a contact area.

The control operation section 332 first reads the contact range table created in Step S40 (Step S242), and also reads the input or set resolution of a tomographic image (Step S243). The resolution of a tomographic image is the degree of accuracy with which a tomographic image of a contact area to be obtained is calculated, for example, the count of interference signals detected per unit area.

From the read contact range table and tomographic image resolution, the control operation section 332 calculates an extent of area in which the optical lens 62 is rotated at high speed and an extent of area in which the optical lens 62 is rotated at low speed (Step S244).

Specifically, the contact area D1 is set as a low-speed rotation domain and the rest (non-contact area D2) is set as a high-speed rotation domain as shown in FIG. 21.

The rotation speed of the optical lens 62 is calculated next (Step S246).

Specifically, when the measuring light beam L1 travels over the contact area D1, the rotation speed of the optical lens 62 is set to a low speed V1 at which enough interference signals to accomplish the set resolution can be obtained and, when the measuring light beam L1 travels over the non-contact area D2, the rotation speed is set to a speed V2 (high speed V2) which makes the measuring light beam L1 travel faster than in the contact area D1.

Based on the calculated rotation speed and rotation domain, the control operation section 332 recalculates the count of lines within the contact area and the positions of the lines (Step S248).

Specifically, the association relation between an interference signal created from the reflected light beam that the optical lens 62 picks up and a measurement point is calculated based on the rotation speed and rotation domain (and rotation position) of the optical lens 62, to thereby associate a line number that is assigned to the interference signal with the measurement point.

In this way, the relation between the rotation action of the optical lens 62 rotated by the rotation driving section 326 and each interference signal detection point is calculated, and hence the detection point of an interference signal can be identified in obtaining a tomographic image. Also calculated is the range of the line number n (in this embodiment, a'≦n≦b') of interference signals created from the reflected light beam that the measurement target S reflects in the contact area.

The rotation driving section 326 rotates the optical lens 62 at the low speed V1 in the contact area D1 and at the high speed V2 in the non-contact area D2 in accordance with the results of the calculations made by the control operation section 332.

Figure 22:
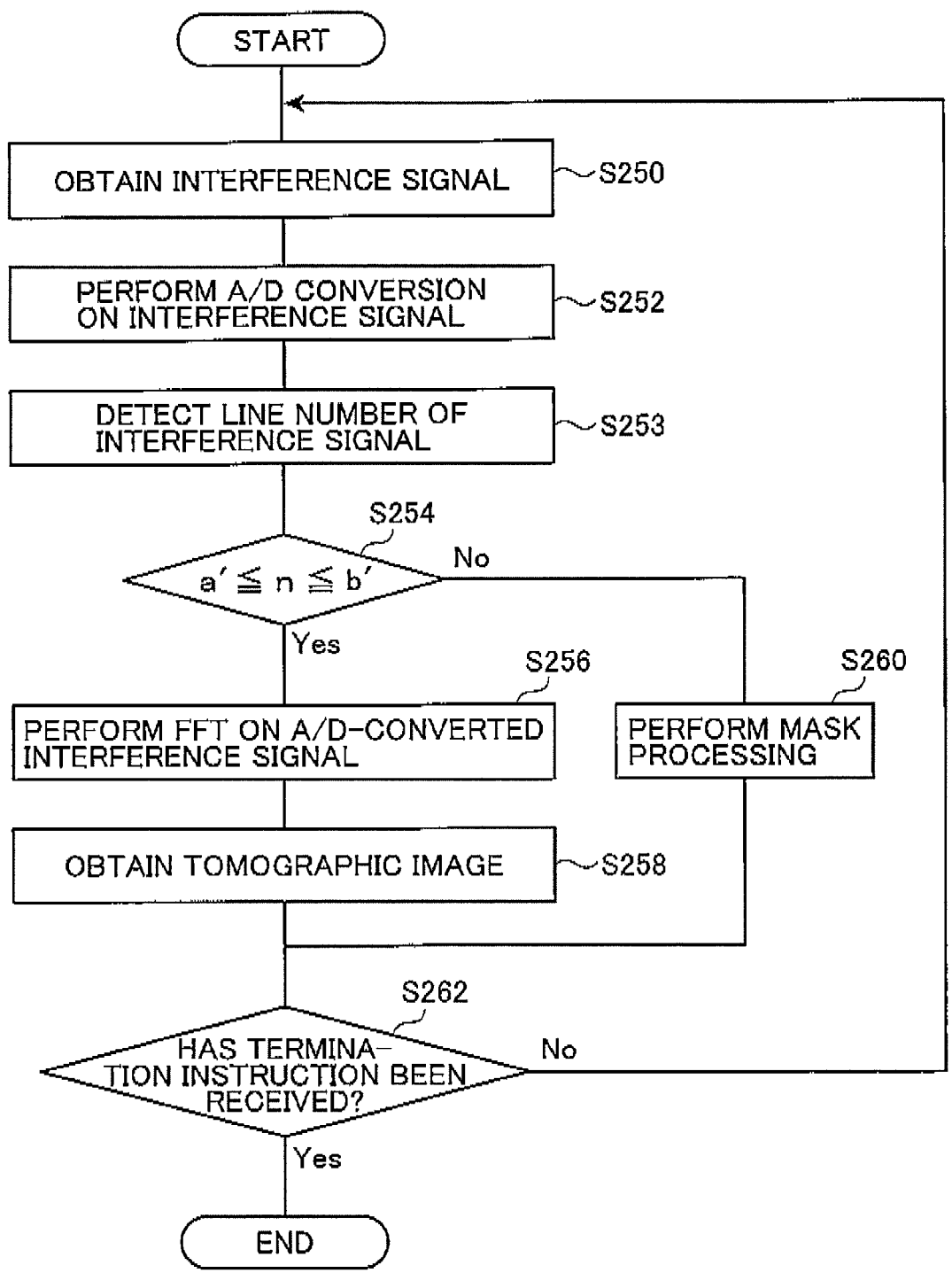
FIG. 22 is a flow chart showing an example of a method of obtaining a tomographic image based on a detected contact area.

A method for obtaining a tomographic image is described next with reference to FIG. 22.

First, interference signals having an arbitrary line number are obtained (Step S250). Specifically, the interference light beam detecting section 20 detects, as an interference signal, the interference light beam L4 which is created by combining the reference light beam L2 and the reflected light beam L3 in the manner described above.

Next, A/D conversion is performed on the detected interference signals (Step S252). Specifically, the A/D conversion means 82 converts the interference signals which are analog signals into digital signals.

The line number n of the interference signals is detected next (Step S253). Specifically, the line number n of the interference signals is identified by reading the line number n that is associated with the interference signals by the interference signal obtaining means 80.

Whether or not the line number n is included in the contact range table created in Step S40, specifically, whether or not the line number n is between the line number a' and the line number b' which define the contact area, is judged next (Step S254). In short, whether a'≦n≦b' is satisfied or not is judged.

When the line number n satisfies a'≦n≦b', FFT is performed on the interference signals converted by A/D conversion (Step S256).

From results of the FFT calculation, a tomographic image for the line number n is obtained (Step S258).

The tomographic image is obtained from results of FFT by performing given processing as described above, After the tomographic image is obtained, the processing proceeds to Step S262.

When the line number n does not satisfy a'≦n≦b', in other words, when n is smaller than a' or larger than b' (n<a' or b'<n), mask processing is performed (Step S260).

Through the mask processing, an all-black image or an invariable predetermined image is given as an image for the line number n, instead of performing FFT and the processing of obtaining a tomographic image.

After the mask processing is finished, the processing proceeds to Step S262.

Whether or not a termination instruction has been received is then judged (Step S262).

In the case where a termination instruction has not been received, the processing moves to Step S250, where interference signals in the next line are processed.

When a termination instruction is received, the processing is ended.

A tomographic image of a measurement target is obtained in the manner described above.

The thus obtained tomographic image is sent to the image correcting means to receive image processing for preparation for display, such as radial transformation and sharpening. The processed image is sent to the display section 24, which then displays the image.

According to the sixth and seventh aspects of the present invention, by detecting a contact area in which a measurement target and the optical probe are in contact with each other with the contact area detecting means, an area where a high-resolution tomographic image will be detected can be detected and recognized. Selective processing of an area where a reliable, high-resolution image will be obtained is thus made possible as in this embodiment.

The present invention also lessens the load on the processing section and shortens the processing time by obtaining only a tomographic image of a contact area and omitting image processing for an area that is not a contact area. In this way, video images can be displayed at high speed even with an inexpensive processor. A high-resolution tomographic image can thus be displayed while keeping the cost of the system low.

Information on a detected contact area is used to obtain a tomographic image of the contact area which is high in resolution and actually needed, while omitting image processing for an area of the measurement target that is apart from the optical probe and will provide a low-resolution, unclear image which is not very useful as a tomographic image. A tomographic image of the present invention can therefore be used effectively. Limiting the execution of image processing to a contact area also makes more sophisticated image processing of a tomographic image possible without increasing the overall information processing amount.

Further, rotating the optical probe at low speed in a contact area of which a tomographic image is obtained and at high speed in an area that is not a contact area improves the scanning speed. A high-precision tomographic image can therefore be obtained in a short period of time or frequently.

In addition, the adjustable rotation speed makes it possible to adjust the count of interference signals obtained per unit area to suit the required resolution.

While the rotation speed of the optical lens 62 alone is varied between a contact area and a non-contact area in this embodiment, the rotation direction of the optical lens 62 may be switched as well in obtaining a tomographic image of the contact area. Specifically, the optical lens 62 may be turned in an area containing a contact area to obtain a tomographic image of the contact area alone.

Figure 24:
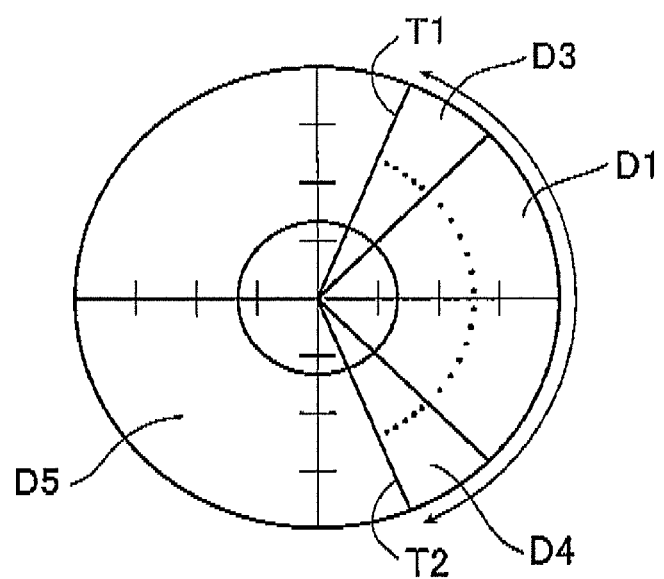
FIG. 24 is an explanatory diagram illustrating a relation between the rotation action of the optical lens which is calculated in FIG. 23 and a contact area.
Figure 23:
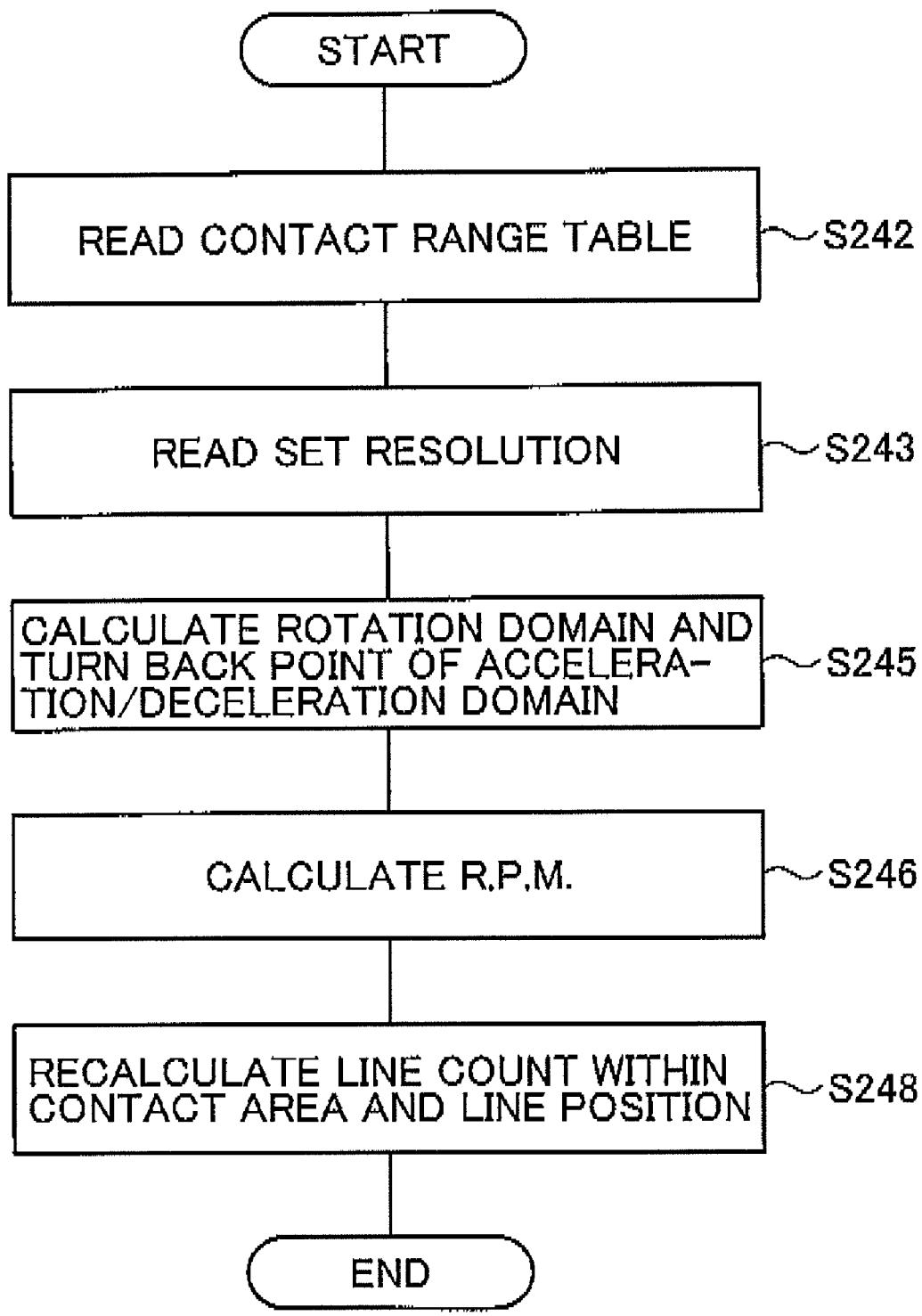
FIG. 23 is a flow chart showing another example of the method of calculating a rotation speed and a rotation direction of the optical lens and a relation between an interference signal and a measurement point.

Described below with reference to FIGS. 23 and 24 is another example of how the control operation section 332 controls the rotation driving section 326 and how the rotation direction and rotation speed of the optical lens are calculated in order to obtain a tomographic image.

FIG. 23 is a flow chart showing another example of the method of calculating the rotation speed and rotation direction of the optical lens 62 and a relation between an interference signal and a measurement point. FIG. 24 is an explanatory diagram illustrating a relation between the rotation action of the optical lens 62 which is calculated in FIG. 23 and a contact area.

In the flow chart of FIG. 23, steps identical to those in the flow chart of FIG. 20 described above are denoted by the same reference numbers and their detailed descriptions are omitted here.

The control operation section 332 first reads the contact range table created in Step S40 (Step S242), and also reads the input or set resolution of a tomographic image (Step S243).

From the read contact range table and tomographic image resolution, the control operation section 332 calculates an extent of area in which the optical lens 62 is rotated at a constant speed in order to obtain a tomographic image in the rotation direction of the optical lens 62 (the circumferential direction of the probe), an extent of area in which the rotation speed of the optical lens 62 is changed in order to switch the rotation direction of the optical lens 62, and a turn back point of the rotation (Step S245).

Specifically, as shown in FIG. 24, the contact area D1 is set as a constant speed domain and, out of the non-contact area, areas D3 and D4 which border the edges of the contact area D1 and which have a given angle with respect to the center of rotation (hereinafter, referred to as "acceleration/deceleration area") are set as acceleration/deceleration domains. An edge of the acceleration/deceleration area D3 that does not adjoin the contact area D1 is set as a turn back point T1. An edge of the acceleration/deceleration area D4 that does not adjoin the contact area D1 is set as a turn back point T2.

The rotation direction of the optical lens 62 is reversed at the turn back points T1 and T2. Therefore, the optical lens 62 does not rotate in an area D5 and the area D5 is not irradiated with the measuring light beam L1.

The rotation speed of the optical lens 62 is calculated next (Step S246).

Specifically, when the measuring light beam L1 travels over the contact area D1, the rotation speed of the optical lens 62 is set to a constant low speed at which a sufficient number of interference signals to accomplish the set resolution can be obtained. In the acceleration/deceleration areas D3 and D4, the rotation direction of the optical lens 62 is switched, and the rotation is decelerated before being stopped at the turn back point T1 or T2, and then accelerated in the reverse direction until the constant speed is reached upon arrival at the contact area D1.

Based on the calculated rotation speed, rotation direction, and rotation domain, the control operation section 332 recalculates the count of lines within the contact area and the positions of the lines (Step S248).

Specifically, the association relation between an interference signal created from the reflected light beam that the optical lens 62 picks up and a measurement point is calculated based on the rotation speed, rotation direction, and rotation domain (and rotation position) of the optical lens 62, to thereby associate a line number that is assigned to the interference signal with the measurement point.

In this way, the relation between the rotation action of the optical lens 62 rotated by the rotation driving section 326 and each interference signal detection point is calculated so that the detection point of an interference signal can be identified in obtaining a tomographic image. Also calculated is the range of the line number n of an interference signal created from the reflected light beam that the measurement target S reflects in the contact area.

The rotation driving section 326 rotates the optical lens 62 at the calculated constant speed in the contact area D1 in accordance with the results of the calculations made by the control operation section 332. The rotation driving section 326 reverses, or switches, the rotation direction of the optical lens 62 resulting from decelerating and stopping the rotation of the optical lens 62 and then accelerating the rotation in the reverse direction in the acceleration/deceleration areas D3 and D4.

The optical lens 62 thus rotates in the contact area D1, the acceleration/deceleration area D3, again the contact area D1, and the acceleration/deceleration area D4 in this order.

Interference signals are created from the reflected light beam which has been obtained while rotating (pivoting, to be exact) the optical lens 62, and processed in the same manner as in FIG. 20, thereby obtaining a tomographic image of the contact area.

Thus, moving the optical lens back and forth in a contact area, too, makes it possible to obtain a high-precision, high-resolution tomographic image of the contact area alone and reduce the information processing amount. Further, by preventing the optical lens from rotating in (the direction of) an area that is not a contact area, a tomographic image of the contact area can be obtained efficiently and the scanning speed can be improved.

The same effects as the ones described above can thus be obtained.

When a tomographic image is obtained from two opposite directions as in this embodiment, associating a line number with positional information enables the display section to display a tomographic image in which images obtained from respective interference signals are positioned correctly.

Preferably, the image correcting means reduces noise in a tomographic image through averaging of a plurality of images respectively obtained from signals of a plurality of adjoining lines.

By reducing noise through averaging of a plurality of adjoining images, a tomographic image higher in image quality and precision can be obtained.

A tomographic image of an area that is not a contact area may be obtained from interference signals, though it increases the information processing amount and the precision of the obtained tomographic image is low because, in the non-contact area, the rotation speed is high and the count of interference signals processed per unit area is small, or the rotation speed is varied and the processing is accordingly complicated.

In the case of obtaining a tomographic image of a non-contact area, too, the count of interference signals processed can be reduced and therefore the information processing amount can be smaller than the case where the rotation speed is constant throughout the entire 360° rotation, while obtaining a high-quality, high-resolution image of a contact area.

The optical tomography imaging system 300 employs swept source-OCT (SS-OCT) to obtain a tomographic image of a measurement target and detect an area of contact with the measurement target, but the present invention is not limited thereto.

Figure 25:
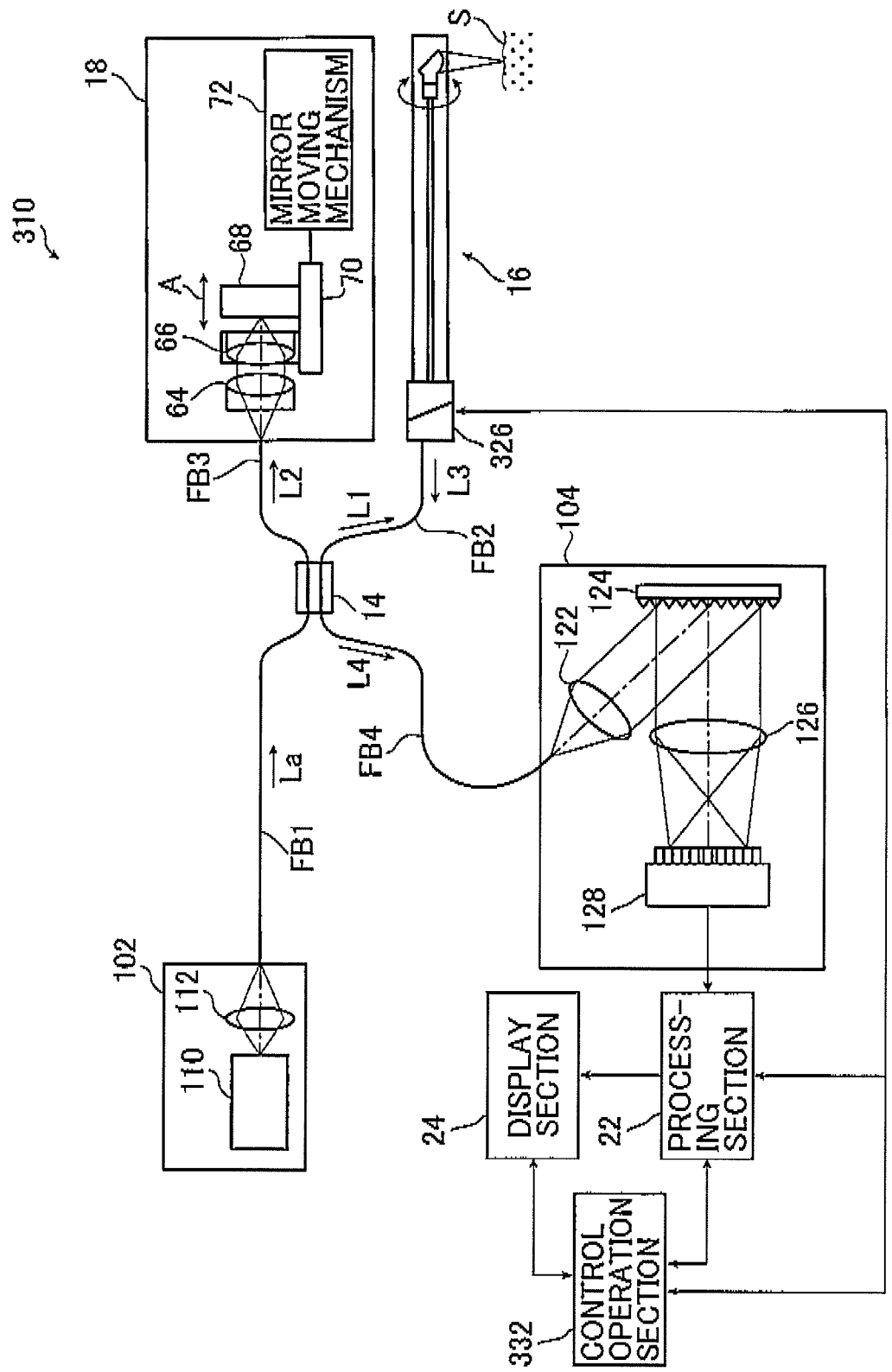
FIG. 25 is a block diagram showing a schematic structure of another embodiment of the optical tomography imaging system according to the seventh aspect of the present invention.

FIG. 25 is a block diagram schematically showing a schematic structure of another embodiment of the optical tomography imaging system.

The optical tomography imaging system shown in FIG. 25 is denoted by 310, and is the same as the optical tomography imaging system 300 except that spectral domain-OCT (SD-OCT) is employed to obtain a tomographic image of a measurement target and detect an area of contact with the measurement target. Components common to the optical tomography imaging system 310 and the optical tomography imaging system 300 are denoted by the same reference symbols and their detailed descriptions are omitted here. Further, the optical tomography imaging system 310 is the same as the optical tomography imaging system 100 except for the rotation driving section 326 and the control operation section 332. Components common to the optical tomography imaging system 310 and the optical tomography imaging system 100 are denoted by the same reference symbols and their detailed descriptions are omitted here. The following description is about the optical tomography imaging system 310.

The optical tomography imaging system 310 has the light source unit 102, which emits a light beam, the branching/multiplexing section 14, which branches the light beam emitted from the light source unit 102 into a measuring light beam and a reference light beam and which combines a reflected light beam with the reference light beam to create an interference light beam, the optical probe 16, which guides the measuring light beam to irradiate a measurement target with the measuring light beam and collect light reflected by the measurement target, the light path length adjusting section 18, which adjusts the light path length of the reference light beam, the interference light beam detecting section 104, which detects the interference light beam created by the branching/multiplexing section 14, the processing section 22, which processes results of detection obtained by the interference light beam detecting section 104, and the display section 24, which displays a tomographic image obtained by the processing section 22. The optical tomography imaging system 310 also has the rotation driving section 326, which rotates the measurement section and others of the optical probe, and the control operation section 332, which inputs various conditions to the processing section 22, the display section 24, and other components, changes settings, and performs other similar operations. An optical fiber is used as a path for light and guides light including the measuring light beam, the reference light beam, and the reflected light beam to relevant components.

The light source unit 102 has the light source 110 and the optical system 112 to make the laser light beam La incident on the optical fiber FB1.

The interference light beam detecting section 104 has the collimator lens 122, the dispersing means 124, the lens 126, and the light detecting means 128. The interference light beam detecting section 104 detects, as an interference signal, the interference light beam L4 which is created in the branching/multiplexing section 14 by combining the reflected light beam L3 and the reference light beam L2. The dispersing means 124 disperses the incident interference light beam L4, which then exits toward the light detecting means 128.

The interference light beam detecting section 104 sends the detected interference signals to the processing section 22.

The contact area detecting means 84 of the processing section 22 detects a contact area in which the circumferential wall of the probe and the measurement target are in contact with each other from detected peak points in the depth direction and intensity distribution, and the tomographic image creating means 86 obtains a tomographic image.

In this way, the optical tomography imaging system 310 employs a different method to obtain interference signals from the optical tomography imaging system 300, but the same effects as in the optical tomography imaging system 300 can be obtained in the optical tomography imaging system 310 by detecting a contact area in which the circumferential wall of the probe and a measurement target are in contact with each other with the contact area detecting means, and by adjusting the rotation speed and rotation direction of the optical probe based on results of the detection so that a tomographic image of the contact area is obtained with higher precision.

Figure 26:
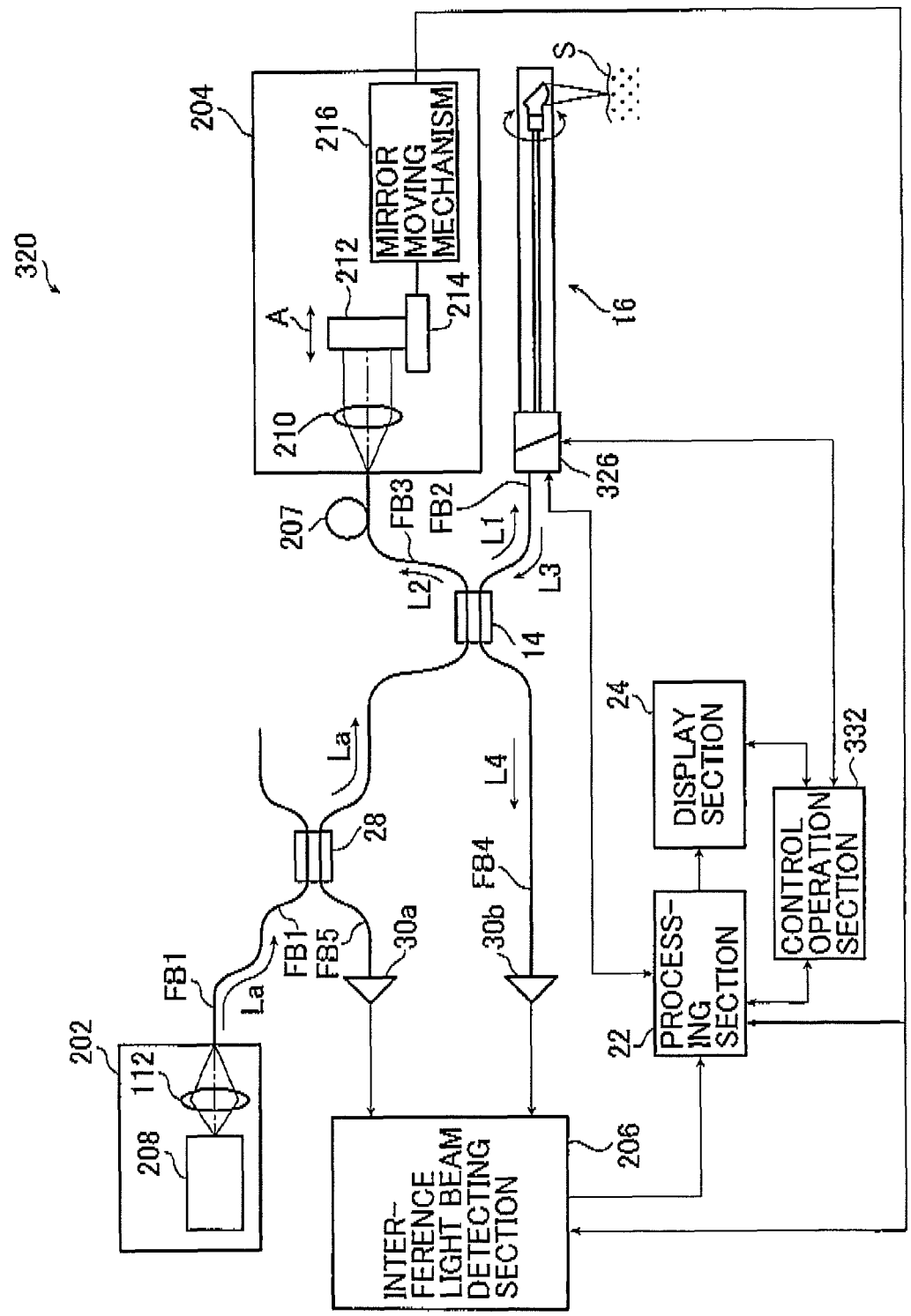
FIG. 26 is a block diagram showing a schematic structure of still another embodiment of the optical tomography imaging system according to the seventh aspect of the present invention.

FIG. 26 is a block diagram schematically showing a schematic structure of still another embodiment of the optical tomography imaging system.

The optical tomography imaging system shown in FIG. 26 is denoted by 320, and is the same as the optical tomography imaging system 300 except that time domain-OCT (TD- OCT) is employed to obtain a tomographic image of a measurement target and detect an area of contact with the measurement target. Components common to the optical tomography imaging system 320 and the optical tomography imaging system 300 are denoted by the same reference symbols and their detailed descriptions are omitted here. Further, the optical tomography imaging system 320 is the same as the optical tomography imaging system 310 except for the light path length adjusting section 204 and the interference light beam detecting section 206. Components common to the optical tomography imaging system 320 and the optical tomography imaging system 310 are denoted by the same reference symbols and their detailed descriptions are omitted here. The following description is about the optical tomography imaging system 320.

The optical tomography imaging system 320 has the light source unit 202, which emits a light beam, the branching/multiplexing section 14, which branches the light beam emitted from the light source unit 202 into a measuring light beam and a reference light beam and which combines a reflected light beam with the reference light beam to create an interference light beam, the optical probe 16, which guides the measuring light beam to irradiate a measurement target with the measuring light beam and collect light reflected by the measurement target, the light path length adjusting section 204, which adjusts the light path length of the reference light beam and changes the light path length periodically, the interference light beam detecting section 206, which detects the interference light beam created by the branching/multiplexing section 14, the processing section 22, which processes results of detection obtained by the interference light beam detecting section 206, and the display section 24, which displays a tomographic image obtained by the processing section 22. The optical tomography imaging system 320 also has the rotation driving section 326, which rotates the measurement section and others of the optical probe, the optical fiber coupler 28, which disperses the light beam emitted from the light source unit 202, the detector section 30a, which detects the reference light beam, the detector section 30b, which detects the reflected light beam, and the control operation section 332, which inputs various conditions to the processing section 22, the display section 24, and other components, changes settings, and performs other similar operations. An optical fiber is used as a path for light and guides light including the measuring light beam, the reference light beam, and the reflected light beam to relevant components.

The light source unit 202 has the light source 208 and the optical system 112 to make the laser light beam La incident on the optical fiber FB1. The optical system 112 collects the laser light beam La emitted from the light source 208 to make the light incident on the optical fiber FB1.

The light path length adjusting section 204 has the collimator lens 210, the mirror 212, the base 214, and the mirror moving mechanism 216. By moving the mirror 212 and varying the light path length of the reference light beam L2, the light path length adjusting section 204 changes the measurement point in the measurement target S in the depth direction.

The phase modulator 207 gives a slight frequency shift to the reference light beam L2.

After being subjected to the light path length change and frequency shift in the light path length adjusting section 204, the reference light beam L2 is guided to the branching/multiplexing section 14.

The branching/multiplexing section 14 combines the reference light beam L2 with the reflected light beam L3 to create the interference light beam L4 as described above.

The interference light beam detecting section 206 employs, for example, heterodyne detection to detect the light intensity of the interference light beam L4 propagated through the optical fiber FB4 from the branching/multiplexing section 14. The interference light beam detecting section 206 therefore detects beat signals, namely, interference signals, for each measurement point. The light path length adjusting section 204 has a calculating section which calculates the measurement point from the mirror position, and outputs the calculated measurement point to the interference light beam detecting section 206 and the processing section 22.

The contact area detecting means 84 and tomographic image creating means 86 of the processing section 22 calculate a relation between the measurement point (i.e., depth direction) and the intensity. From the calculated depth direction-intensity relation, peak points in the depth direction and the intensity distribution can be obtained as in the optical tomography imaging system 300.

The contact area detecting means 84 detects a contact area in which the circumferential wall of the probe and the measurement target are in contact with each other from the detected peak points in the depth direction and intensity distribution, and the tomographic image creating means 86 obtains a tomographic image.

In this way, although the optical tomography imaging system 320 employs a different method to obtain interference signals from the optical tomography imaging system 300, the same effects as in the optical tomography imaging system 300 can be obtained in the optical tomography imaging system 320 by detecting a contact area in which the circumferential wall of the probe and a measurement target are in contact with each other with the contact area detecting means, and by adjusting the rotation speed and rotation direction of the optical probe based on results of the detection so that a tomographic image of the contact area is obtained with higher precision.

A detailed description has been given on an optical tomography imaging system of the present invention, a contact area detecting method of the present invention and an image processing method using the detecting method, and an optical tomographic image obtaining method of the present invention. However, the present invention is not limited to the above embodiments and is open to various improvements and modifications without departing from the spirit of the present invention.

For example, the above embodiments employ fast Fourier transform (FFT) in SS-OCT and SD-OCT, but various other frequency analysis methods that can calculate a relation between the frequency and the intensity can be employed instead.

In the fourth to seventh aspects of the present invention, contact area detection by the measurement section of the optical probe as employed in the above embodiments is preferable because it does not require a new mechanism, which means that the optical tomography imaging system can be made more compact, and because it is conducted at the measurement point, which-means more accurate contact area detection. However, other contact area detecting methods may be employed and, for example, a sensor separate from the measurement section of the optical probe may be used to detect a contact state.

The present invention is not limited to particular methods in setting an extent of area for the contact range table and in setting a contact area. Lines that are equal to or smaller than a threshold alone may be detected as a contact area, or an area containing successive lines where the optical probe and the measurement target are judged as being in contact with each other may be detected as a contact area. Alternatively, the width of a contact area may be set, in other words, a contact area may be defined by the count of lines.

In the above embodiments, the measurement area has one contact area and the rest is a non-contact area. Alternatively, a plurality of contact areas may be detected. That the plurality of contact areas are detected means that there are a plurality of line number ranges which define the contact areas to be processed, but the above-mentioned processing can be employed in this case, too.

An arbitrary value can be set as the threshold with which whether or not the probe sheath and the measurement target are in contact with each other is judged, and the threshold may be reset by an input from the operator or to suit a condition.

It is preferable that the optical tomography imaging system has an increase instructing section, which expands a contact area by a given extent of area, namely, a given count of lines, when obtaining a tomographic image. The increase instructing section may be newly installed as a specific button, or may be part of the control operation section.

Making a contact area expandable with the use of the increase instructing section enables the operator to check the adjacent are outside of the currently obtained tomographic image, and information that the operator desires can be provided in a favorable manner.

The control operation section is preferably capable of switching and expanding an area of which a tomographic image is to be obtained.

In this way, a tomographic image of an area that the operator desires can be obtained in addition to a contact area detection result.

The above embodiments use the encoder of the rotation driving section to calculate the point of measurement with the measuring light beam, but the present invention is not limited thereto. For example, since one cycle of a laser light beam which is emitted from the light source and has frequency swept in a given cycle corresponds to one line of interference signals, the count of lines may be detected from the laser light cycle to be used in the calculation of a measurement point with respect to a reference point.

In the above embodiments, the position of the surface of the measurement target is detected at every line, but the present invention is not limited thereto, and a contact area may be detected by detecting the position of the surface of the measurement target at each given line, for example, a line having a line number of an even number or of a multiple of 3. By thus conducting measurement target detection at fewer lines, the information processing amount can be reduced and the processing can be sped up. Further, detection at each given line can detect a contact area appropriately because the periphery of lines where the probe and the measurement target are judged as being in contact with each other can be set as a contact area.

In the above embodiments, the processing starts from the line having a line number n=1. However, the start point of the processing is not particularly limited as long as the circumferential wall of the probe can be detected along the entire circumferential length.

The circumferential wall of the probe is calculated from detection results of one line alone in the above embodiments. Alternatively, detection may be conducted at a plurality of lines, and hence the mean value of calculation results is used as the position of the circumferential wall of the probe.

When to detect a contact area in which the probe sheath and the measurement target are in contact with each other is not particularly limited. Contact area detection may be executed whenever the rotation driving section finishes rotating the optical lens and the optical fiber a given number of times, or when a detection instruction is received from the operator.

By conducting contact area detection whenever the optical lens and the optical fiber finish rotating a given number of times, an area where a high-resolution image will be obtained can be recognized automatically, which enables the optical tomography imaging system to quickly deal with a switch from one contact area to another.

In the case where a tomographic image of a contact area alone is obtained and displayed with the display section, the image correcting means may rotate the tomographic image to provide a better view of the displayed tomographic image to the operator, and may also enlarge the tomographic image.

Performing processing of rotating and enlarging a tomographic image before displaying the image with the display section in this manner enables the operator to inspect the tomographic image with ease.

In the fourth to seventh aspects of the present invention, the display section may display a tomographic image with a contact area superimposed on the tomographic image. Further, the display section may display a tomographic image along with the reliability of the tomographic image and the distance from the measurement target which are calculated from information on the contact state and a detected contact area. Detecting a contact area and displaying the detection result enable the operator to readily recognize an area where a high-resolution image will be obtained.

What is claimed is:

1. An optical tomography imaging system comprising:
    a light source;
    a branching section which branches a light beam emitted from said light source into a measuring light beam and a reference light beam;
    an optical probe having an optical fiber which propagates said measuring light beam, a measurement section which is placed at a tip of said optical fiber to irradiate a measurement target with said measuring light beam and to pick up a reflected light beam of said measuring light beam, and a sheath which encloses circumferential walls of said optical fiber and said measurement section and which is partially formed from a transparent material in an area where said measuring light beam exits said measurement section and said reflected light beam enter said measurement section;
    a driving section which rotates said measurement section and said optical fiber;
    a multiplexing section which combines said reflected light beam detected by said measurement section with said reference light beam to create an interference light beam;
    an interference light beam detecting section which detects said interference light beam as interference signals;
    a contact detecting section which detects a contact area in which said optical probe and said measurement target are in contact with each other; and
    a tomographic image obtaining section which obtains a tomographic image from the detected interference signals,
    wherein said contact detecting section calculates from the detected interference signals a distance between said optical probe and said measurement target, and uses the calculated distance to detect a contact area in which said optical probe and said measurement target are in contact with each other.

2. The optical tomography imaging system according to claim 1, wherein said tomographic image obtaining section obtains a tomographic image of only the contact area detected by said contact detecting section.

3. The optical tomography imaging system according to claim 1,
wherein said tomographic image obtaining section obtains a first tomographic image by processing the interference signals of the contact area under a first processing condition, and obtains a second tomographic image by processing the interference signals of other areas than the contact area under a second processing condition, and
wherein the first processing condition is a condition that makes processing accuracy higher than the second processing condition does.

4. The optical tomography imaging system according to claim 3, wherein the first processing condition is a condition that makes a processing amount for one interference signal larger than the second processing condition does.

5. The optical tomography imaging system according to claim 3, wherein the first processing condition is a condition that makes a count of the interference signals processed per unit area larger than the second processing condition does.

6. The optical tomography imaging system according to claim 3, further comprising a condition setting section which sets the first processing condition and the second processing condition.

7. The optical tomography imaging system according to claim 1,
wherein said tomographic image obtaining section processes at least the interference signals of the contact area to obtain the tomographic image, and
wherein said driving section rotates said measurement section at different rotation speeds in the contact area and in other areas than the contact area.

8. The optical tomography imaging system according to claim 7, wherein said driving section rotates said measurement section so that, when picking up the reflected light beam of the measurement target in the contact area, said measurement section rotates at a lower rotation speed than when picking up the reflected light beam of the measurement target in the other areas than the contact area.

9. The optical tomography imaging system according to claim 7,
wherein said driving section varies a direction of rotation of said measurement section as well, and
wherein said measurement section is turned in two opposite directions to pick up a reflected light beam of the measurement target in the contact area.

10. The optical tomography imaging system according to claim 7, further comprising a drive control section which, based on an extent and location of the contact area detected by said contact detecting section, sets a rotation speed and a rotation position of said measurement section rotated by said driving section.

11. The optical tomography imaging system according to claim 10, wherein said drive control section sets the rotation speed and the rotation position of said measurement section based also on a set resolution of the tomographic image.

12. The optical tomography imaging system according to claim 7, wherein said tomographic image obtaining section obtains a tomographic image by processing only the interference signals of the contact area.

13. The optical tomography imaging system according to claim 3, wherein said contact detecting section calculates from the interference signals the distance between said optical probe and said measurement target, and uses the calculated distance to detect the contact area in which said optical probe and said measurement target are in contact with each other.

14. The optical tomography imaging system according to claim 1, wherein said contact detecting section detects an area in which the calculated distance between said optical probe and said measurement target is equal to or smaller than a given value as an area in a contact state and, from a result of the detection, detects the contact area.

15. The optical tomography imaging system according to claim 1, wherein said contact detecting section executes contact state detection whenever said driving section finishes rotating said measurement section and said optical fiber a given number of times.

16. The optical tomography imaging system according to claim 1, further comprising a display section which displays the tomographic image obtained by said tomographic image obtaining section.

17. The optical tomography imaging system according to claim 1, further comprising an operation section which changes the contact area detected by said contact detecting section.

18. The optical tomography imaging system according to claim 1, further comprising a light path length adjusting section which is placed in a light path of the reference light beam and adjusts a light path length of the reference light beam,
wherein said light path length adjusting section varies the light path length of the reference light beam in order to create an interference light beam for each point in a depth direction of said measurement target.

19. The optical tomography imaging system according to claim 1,
wherein said interference light beam detecting section detects the interference signals for each light spectral component,
wherein said contact detecting section performs a frequency analysis on the interference signals and calculates from a result of the frequency analysis the distance between said optical probe and said measurement target, and
wherein said tomographic image obtaining section performs a frequency analysis on the interference signals and obtains the tomographic image from a result of the frequency analysis.

20. A contact area detecting method for detecting a state of contact between a measurement target and an optical probe of an optical tomography imaging system which obtains a tomographic image of said measurement target from an interference light beam created by combining a reference light beam with a reflected light beam which is reflected by said measurement target irradiated with a measuring light beam and which is picked up by a measurement section placed at a tip of said optical probe, said measurement section being rotated while irradiating said measurement target with said measuring light beam, said method comprising:
a probe position obtaining step of detecting a position of a circumferential wall of said optical probe from said reflected light beam of said measuring light beam which is picked up as a result of projecting said measuring light beam from said measurement section;
a measurement target position detecting step of detecting a position of a surface of said measurement target from said reflected light beam which is picked up as a result of projecting said measuring light beam while rotating said measurement section at a measurement point of said measurement target;

a distance detecting step of detecting a distance between said measurement target and the circumferential wall of said optical probe;

a contact point judging step of judging an area in which the distance between the circumferential wall of said optical probe and the surface of said measurement target is equal to or smaller than a given value as an area where said optical probe is in contact with said measurement target; and a contact area detecting step of detecting a contact area in which the circumferential wall of said optical probe and the surface of said measurement target are in contact with each other from a result of said judging in the contact point judging step.

21. The contact area detecting method according to claim 20, wherein, in said measurement target position detecting step, a peak point where intensity of said reflected light beam exceeds a given threshold outside of the circumferential wall of said optical probe is detected as the surface of said measurement target.

22. The contact area detecting method according to claim 20, further comprising a distance setting step of setting a distance for judging that said optical probe is in contact with said measurement target.

23. An image processing method for obtaining a tomographic image of a measurement target, comprising:

a contact area setting step of using a contact area detecting method for detecting a state of contact between said measurement target and an optical probe of an optical tomography imaging system to detect and set a contact area in which said optical probe and said measurement target are in contact with each other, said optical tomography imaging system obtaining a tomographic image of said measurement target from an interference light beam created by combining a reference light beam with a reflected light beam which is reflected by said measurement target irradiated with a measuring light beam and which is picked up by a measurement section placed at a tip of said optical probe, said measurement section being rotated while irradiating said measurement target with said measuring light beam, said contact area detecting method comprising:

a probe position obtaining step of detecting a position of a circumferential wall of said optical probe from said reflected light beam of said measuring light beam which is picked up as a result of projecting said measuring light beam from said measurement section;

a measurement target position detecting step of detecting a position of a surface of said measurement target from said reflected light beam which is picked up as a result of projecting said measuring light beam while rotating said measurement section at a measurement point of said measurement target;

a distance detecting step of detecting a distance between said measurement target and the circumferential wall of said optical probe;

a contact point judging step of judging an area in which the distance between the circumferential wall of said optical probe and the surface of said measurement target is equal to or smaller than a given value as an area where said optical probe is in contact with said measurement target; and a contact area detecting step of detecting a contact area in which the circumferential wall of said optical probe and the surface of said measurement target are in contact with each other from a result of said judging in the contact point judging step;

an interference signal obtaining step of creating the interference light beam from a reflected light beam which is picked up while rotating said measurement section, and obtaining said interference light beam as interference signals; and a tomographic image obtaining step of obtaining said tomographic image by processing only said interference signals of the contact area detected in said contact area detecting step.

24. The image processing method according to claim 23, further comprising a display step of performing one of rotation processing and enlarging processing on said obtained tomographic image and then displaying said processed tomographic image on a screen.

25. An optical tomographic image obtaining method for obtaining a tomographic image of a measurement target from an interference light beam created by combining a reference light beam with a reflected light beam which is reflected by the measurement target irradiated with a measuring light beam and which is picked up by a measurement section placed at a tip of an optical probe, said measurement section being rotated while irradiating said measurement target with said measuring light beam, said method comprising:

a contact area detecting step of detecting a state of contact between a circumferential wall of said optical probe and said measurement target, and detecting a contact area from a result of the detection of said state of contact;

an interference signal obtaining step of creating said interference light beam from said reflected light beam of said measuring light beam which is picked up while rotating said measurement section, and obtaining said interference light beam as interference signals; and a tomographic image obtaining step of obtaining said tomographic image by processing said interference signals under a first processing condition when said interference signals are created from a first reflected light beam that is reflected by said measurement target in the contact area, and under a second processing condition when said interference signals are created from a second reflected light beam that is reflected by said measurement target in other areas than the contact area, wherein said first processing condition is a condition that makes processing accuracy higher than said second processing condition does.

26. The optical tomographic image obtaining method according to claim 25, wherein said first processing condition is a condition that makes a processing amount for one interference signal larger than said second processing condition does.

27. The optical tomographic image obtaining method according to claim 25, wherein said first processing condition is a condition that makes a count of interference signals processed per unit area larger than said second processing condition does.

28. The optical tomographic image obtaining method according to claim 25, further comprising a condition setting step of setting said first processing condition and said second processing condition based on input information.

29. An optical tomographic image obtaining method for obtaining a tomographic image of a measurement target from an interference light beam created by combining a reference light beam with a reflected light beam which is reflected by said measurement target irradiated with a measuring light beam and which is picked up by a measurement section placed at a tip of an optical probe, said measurement section being rotated while irradiating said measurement target with said measuring light beam, said method comprising:

a contact area detecting step of detecting a state of contact between a circumferential wall of said optical probe and said measurement target, and detecting a contact area from a result of the detection of said state of contact;

a rotation setting step of calculating and setting rotation speed of said measurement section based on the contact area detected in said contact area detecting step;

an interference signal obtaining step of creating said interference light beam from said reflected light beam of said measuring light beam, which is picked up while rotating said measurement section in accordance with settings set in said rotation setting step, and obtaining said interference light beam as interference signals; and a tomographic image obtaining step of obtaining said tomographic image by processing at least interference signals created from a first reflected light beam that is reflected by said measurement target in the contact area, wherein, in said rotation setting step, said rotation speed of said measurement section is set at least such that, when picking up said first reflected light beam of said contact area, said measurement section rotates at a different speed than when picking up a second reflected light beam of other areas than said contact area.

30. The optical tomographic image obtaining method according to claim 29, wherein, in said rotation setting step, said rotation speed of said measurement section is set such that, when picking up said first reflected light beam of the contact area, said measurement section rotates at a lower speed than when picking up said second reflected light beam of the other areas than said contact area.

31. The optical tomographic image obtaining method according to claim 29, wherein, in said rotation setting step, a rotation direction of said measurement section is calculated and set in addition to said rotation speed of said measurement section, and hence said measurement section moves back and forth in said contact area.

32. The optical tomographic image obtaining method according to claim 29, wherein the calculating and setting in said rotation setting step is performed based on, in addition to said contact area detected in said contact area detecting step, a set resolution of said tomographic image.

33. The optical tomographic image obtaining method according to claim 29, wherein, in said tomographic image obtaining step, said tomographic image is obtained by processing a plurality of interference signals separately to obtain image signals and then performing noise reduction processing on said image signals.

34. The optical tomographic image obtaining method according to claim 29, wherein, in said tomographic image obtaining step, said tomographic image is obtained by processing only interference signals that are created from said first reflected light beam of said measurement target in said contact area.

35. The optical tomographic image obtaining method according to claim 25, wherein said contact area detecting step includes:
   a probe position obtaining step of detecting a position of the circumferential wall of said optical probe from a reflected light beam which is picked up as a result of projecting a measuring light beam from said measurement section;
   a measurement target position detecting step of detecting a position of a surface of said measurement target from a reflected light beam which is picked up as a result of projecting a measuring light beam while rotating the measurement section at a measurement point of said measurement target;
   a distance detecting step of detecting a distance between said measurement target and the circumferential wall of said optical probe;
   a contact point judging step of judging an area in which the distance between the circumferential wall of said optical probe and the surface of said measurement target is equal to or smaller than a given value as an area where said optical probe is in contact with said measurement target; and
   a contact area detecting step of detecting a contact area in which the circumferential wall of said optical probe and the surface of said measurement target are in contact with each other from a result of the judging in said contact point judging step.

36. The optical tomographic image obtaining method according to claim 35, wherein, in said measurement target position detecting step, a peak point where intensity of said reflected light beam exceeds a given threshold outside of the circumferential wall of said optical probe is detected as the surface of said measurement target.

37. The optical tomographic image obtaining method according to claim 35, further comprising a distance setting step of setting a distance for judging that said optical probe is in contact with said measurement target.

38. The optical tomographic image obtaining method according to claim 25, further comprising a display step of performing one of rotation processing and enlarging processing on the obtained tomographic image and then displaying the processed tomographic image on a screen.

* * * * *